(12) United States Patent
Nabatova-Gabain et al.

(10) Patent No.: US 8,013,997 B2
(45) Date of Patent: Sep. 6, 2011

(54) SAMPLE ANALYZING METHOD, SAMPLE ANALYZING APPARATUS, MANUFACTURING METHOD OF ORGANIC EL ELEMENT, MANUFACTURING EQUIPMENT, AND RECORDING MEDIUM

(75) Inventors: Nataliya Nabatova-Gabain, Kyoto (JP); Yoko Wasai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 12/697,079

(22) Filed: Jan. 29, 2010

(65) Prior Publication Data
US 2010/0136217 A1   Jun. 3, 2010

Related U.S. Application Data

(62) Division of application No. 11/605,535, filed on Nov. 28, 2006, now Pat. No. 7,688,446.

(30) Foreign Application Priority Data

Nov. 29, 2005 (JP) ................. 2005-344457
Mar. 31, 2006 (JP) ................. 2006-099445
Aug. 23, 2006 (JP) ................. 2006-226952

(51) Int. Cl.
G01J 4/00 (2006.01)
(52) U.S. Cl. ...................................................... 356/369
(58) Field of Classification Search .................. 356/369, 356/630, 632
See application file for complete search history.

(56) References Cited

U.S. PATENT DOCUMENTS

| | | | |
|---|---|---|---|
| 5,793,480 A * | 8/1998 | Lacey et al. ........................ 356/73 |
| 6,292,265 B1 * | 9/2001 | Finarov et al. ................. 356/630 |
| 6,762,838 B2 * | 7/2004 | Du-Nour ........................ 356/632 |
| 6,801,326 B2 * | 10/2004 | Finarov et al. ................. 356/630 |
| 7,209,233 B2 * | 4/2007 | Soga et al. ..................... 356/369 |
| 7,327,455 B2 * | 2/2008 | Sakai et al. .................... 356/364 |
| 2001/0024277 A1 | 9/2001 | Hirosawa et al. |
| 2002/0005957 A1 * | 1/2002 | Finarov et al. ................. 356/630 |
| 2003/0193672 A1 | 10/2003 | Okada et al. |

(Continued)

FOREIGN PATENT DOCUMENTS

DE    41 08 329    9/1992

(Continued)

OTHER PUBLICATIONS

Jellison, Jr., G.E. et al. "Spectroscopic Ellipsometry Characterization of Thin-Film Silicon Nitride", 1998 Elsevier Science S.A.; pp. 193-197.

(Continued)

*Primary Examiner* — Roy Punnoose

(57) ABSTRACT

Light is irradiated onto a glass substrate of an organic EL element, and the characteristics of an organic film are analyzed. In the sample analyzing apparatus, in such a way that the glass substrate is located on the upper side, the organic EL element is placed on a stage. The light is irradiated towards the glass substrate, and an amplitude ratio and a phase difference which are related to the organic EL element are measured. Also, the sample analyzing apparatus selects a model of a structure corresponding to reflected lights K1 to K3 of the irradiated light and calculates the amplitude ratio and the phase difference. The sample analyzing apparatus compares the measured result and the result calculated from the model, and properly executes the fitting, and determines the best model among the several models and then analyzes the characteristics related to the organic EL element.

20 Claims, 49 Drawing Sheets

U.S. PATENT DOCUMENTS

| | | | |
|---|---|---|---|
| 2005/0195395 A1* | 9/2005 | Soga et al. | 356/369 |
| 2005/0200845 A1 | 9/2005 | Nabatova-Gabain et al. | |
| 2005/0208698 A1 | 9/2005 | Winters et al. | |
| 2005/0227385 A1 | 10/2005 | Tan | |
| 2005/0244570 A1 | 11/2005 | Tanase et al. | |
| 2006/0023213 A1 | 2/2006 | Funakubo et al. | |
| 2006/0185588 A1 | 8/2006 | Nozawa et al. | |

FOREIGN PATENT DOCUMENTS

| | | |
|---|---|---|
| EP | 1 357 200 | 10/2003 |
| JP | 63-307654 | 12/1988 |
| JP | H02-083438 | 6/1990 |
| JP | 03-246448 | 11/1991 |
| JP | 06-034523 | 2/1994 |
| JP | 2000-294372 | 10/2000 |
| JP | 2000-352506 | 12/2000 |
| JP | 2001-126324 | 5/2001 |
| JP | 2002-340528 | 11/2002 |
| JP | 2002-340789 | 11/2002 |
| JP | 2003-243467 | 8/2003 |
| JP | 2004-069401 | 3/2004 |
| JP | 2005-055407 | 3/2005 |
| JP | 2005-216582 | 8/2005 |
| JP | 2005-241282 | 9/2005 |
| JP | 2005-257475 | 9/2005 |
| JP | 2005-283502 | 10/2005 |
| JP | 2005-322612 | 11/2005 |
| JP | 2005-344168 | 12/2005 |
| JP | 2006-47015 | 2/2006 |
| JP | 2006-511823 | 4/2006 |
| JP | 2006-176831 | 7/2006 |
| KR | 1020010091030 | 10/2001 |
| KR | 20020005314 | 1/2002 |
| KR | 20020005839 | 1/2002 |
| KR | 1020020060155 | 7/2002 |
| KR | 1020050096847 | 10/2005 |
| KR | 1020060021210 | 3/2006 |
| WO | WO 01/11310 | 2/2001 |
| WO | 2004/059266 | 7/2004 |
| WO | 2005-093875 | 10/2005 |

OTHER PUBLICATIONS

Terai, A. et al., "Analysis of Organic Electroluminescent Film by Spectroscopic Ellipsometer 1", Extended Abstracts (The 66$^{th}$ Autumn Meeting 2005): The Japan Society of Applied Physics No. 3, *The Japan Society of Applied Physics*, Japan, Sep. 7, 2005, p. 1144; with English translation.

Hartmann, E. et al.; "UV-VIS and mid-IR ellipsometer characterization of layers used on OLED devices"; Journal of Luminescence 110 (2004) pp. 407-412.

Tsuboi, Taiju et al.; "Spectroscopic Ellipsometry Study of Organic Light Emitting Diode Based on Phosphorescent PtOEP"; IEICE Trans Electron vol. E87-C, No. 12, Dec. 2004; pp. 2039-2044.

Tsuboi, Taiju et al.; "Optical Constants of Platinum Octaethyl Porphyrin in Single-Layer Organic Light Emitting Diode Studied by Spectroscopic Ellipsometry"; Thin Solid Films 496 (2006) pp. 674-678.

Nabatova-Gabain, Nataliya et al.; "Spectroscopic Ellipsometry Study of Ir(ppy)3 Organic Light Emitting Diode"; Current Applied Physics 6 (2006) pp. 833-838.

* cited by examiner

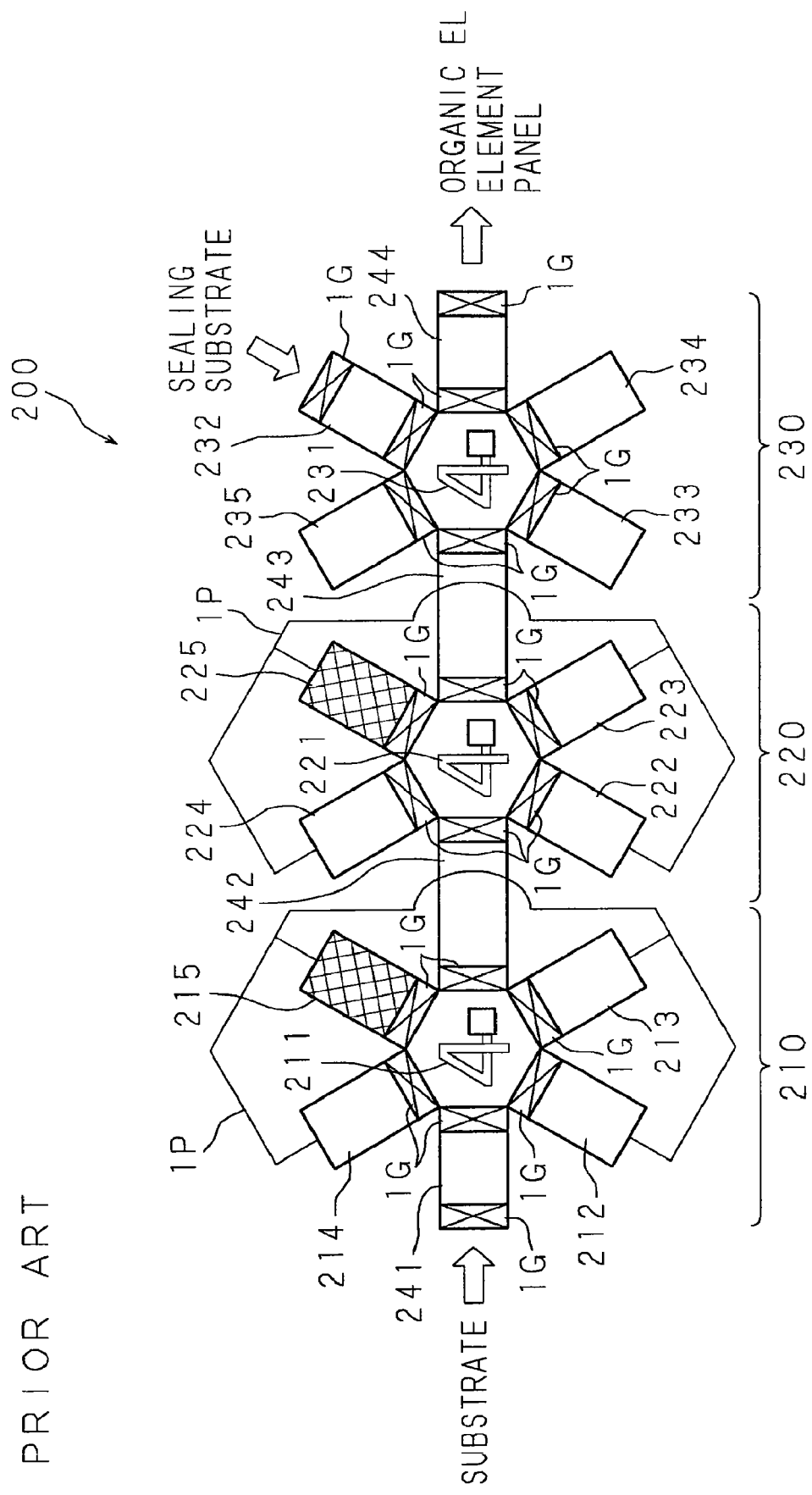

FIG. 7

| | | | Standard Value |
|---|---|---|---|
| 21 → | THICKNESS OF GAP | VOID | μm (21a) | μm (21b) |
| 22 → | FILM | FILM THICKNESS (Å) | |
| 23 → | SUBSTRATE | | |

20

F I G. 34A
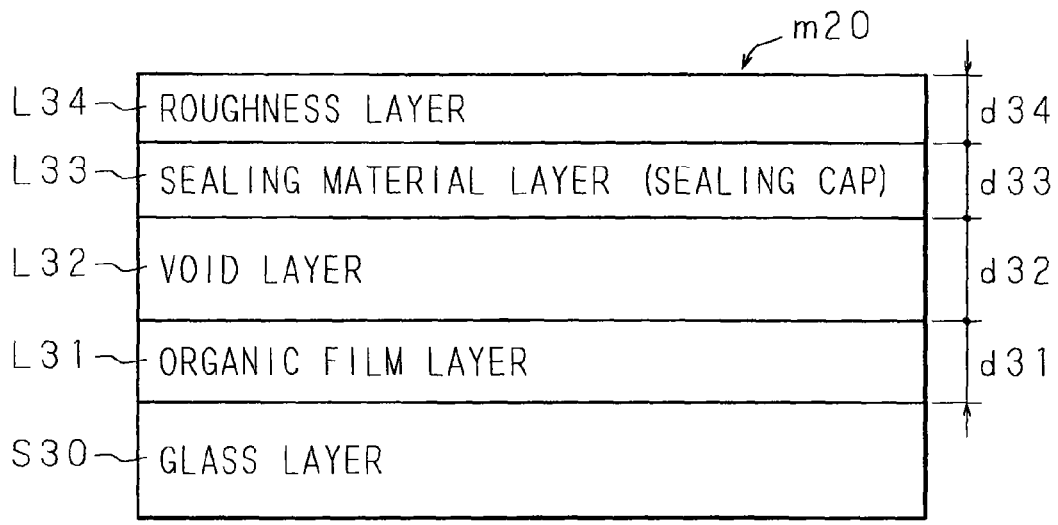
F I G. 34B
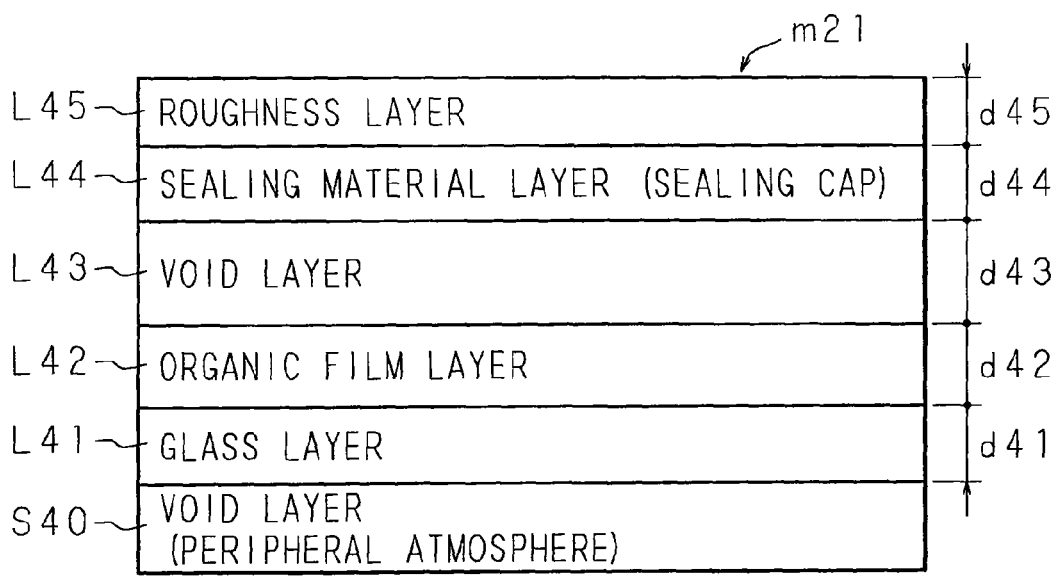

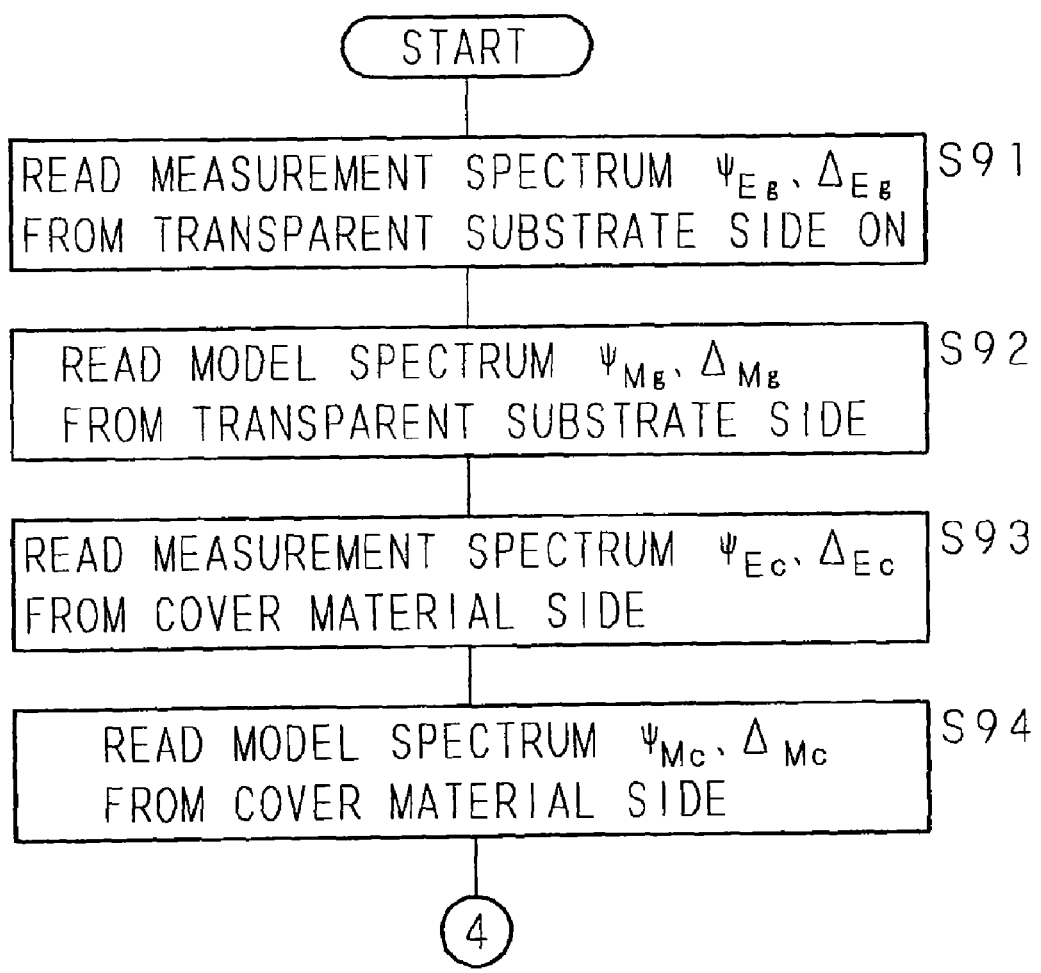

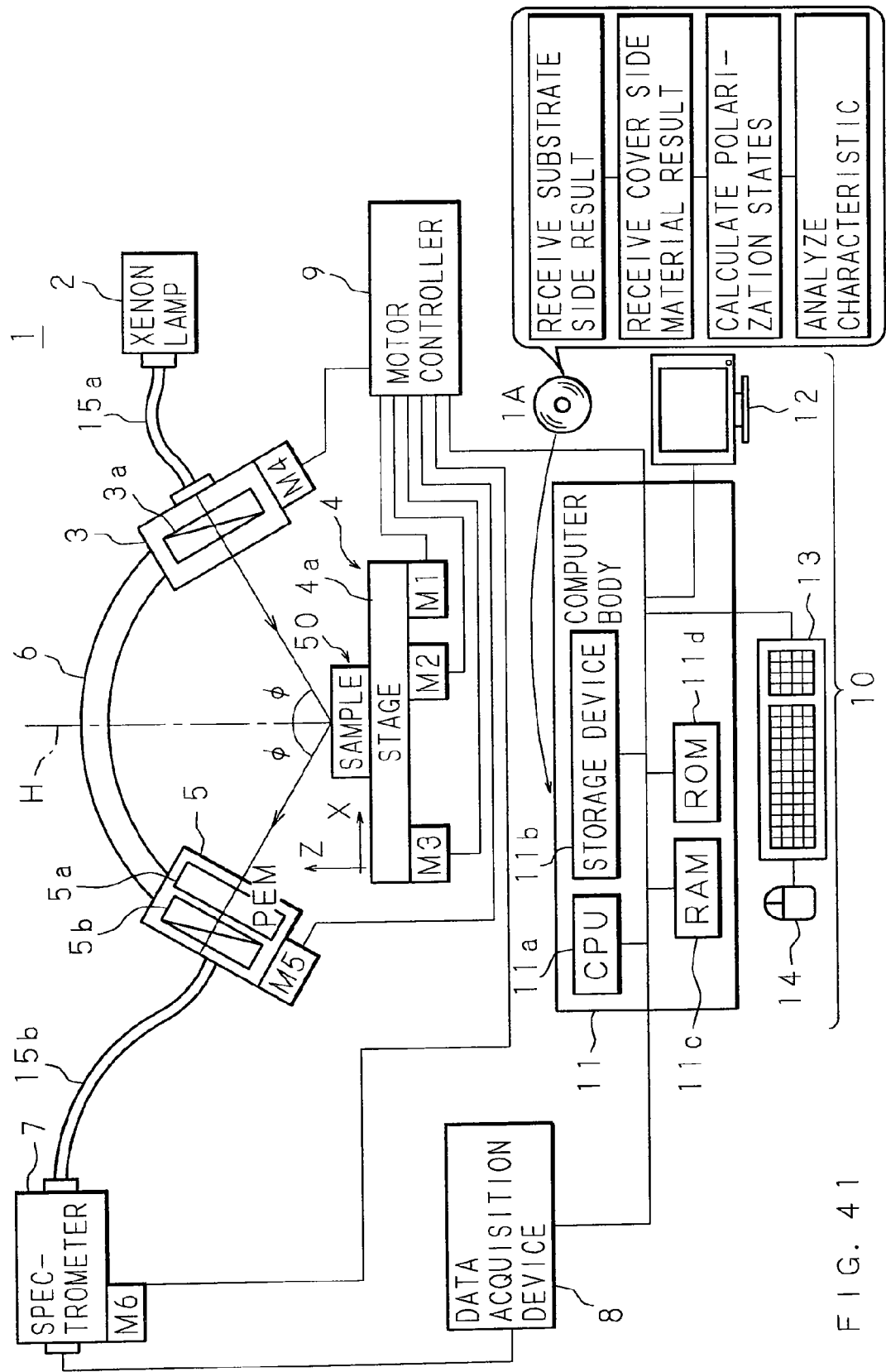
F I G. 41

F I G. 4 2 B
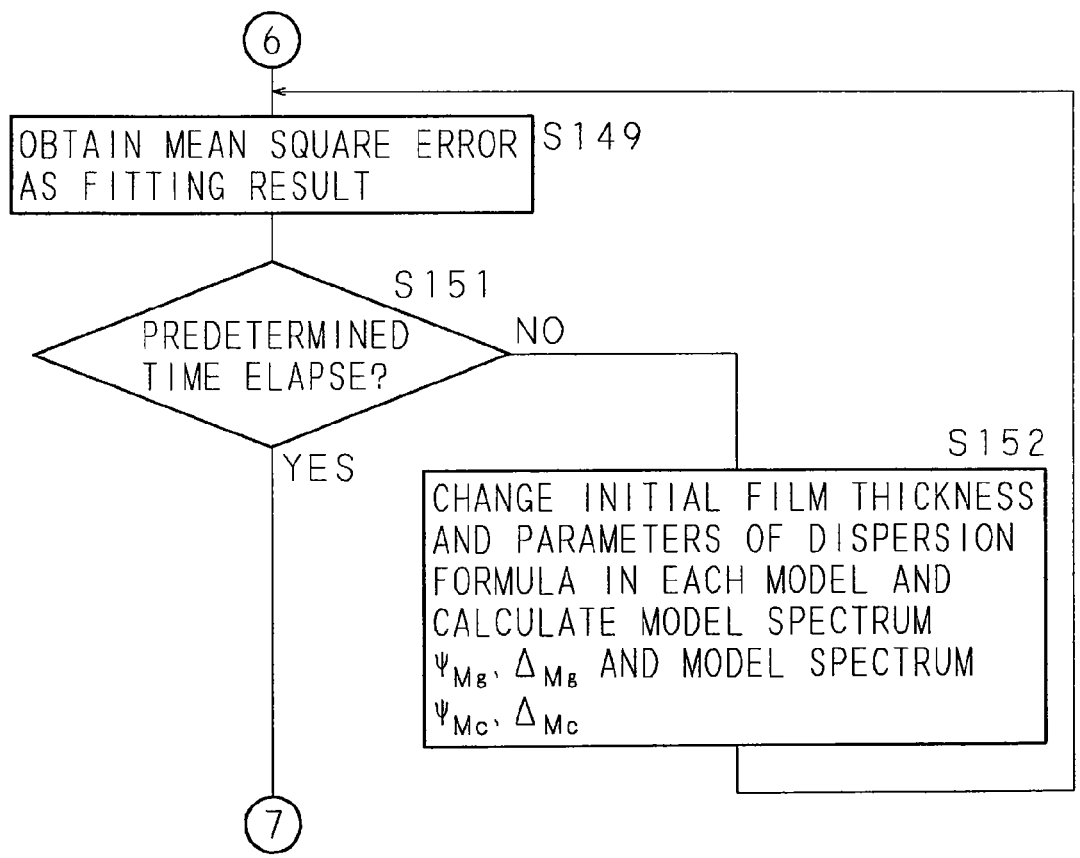

SAMPLE ANALYZING METHOD, SAMPLE ANALYZING APPARATUS, MANUFACTURING METHOD OF ORGANIC EL ELEMENT, MANUFACTURING EQUIPMENT, AND RECORDING MEDIUM

CROSS REFERENCE TO RELATED APPLICATIONS

This application is a divisional application from U.S. Ser. No. 11/605,535 filed on Nov. 28, 2006, now U.S. Pat. No. 7,688,446 which claims priority from Japanese Patent Application No. 2005-344457 filed on Nov. 29, 2005, Japanese Patent Application No. 2006-099445 filed on Mar. 31, 2006, and Japanese Patent Application No. 2006-226952 filed on Aug. 23, 2006, the entire contents of which are hereby incorporated by reference.

BACKGROUND OF THE INVENTION

1. Field of the Invention

The present invention relates to a sample analyzing method and a sample analyzing apparatus that measure optical characteristics of a sample, in which a multi-layer structure deposited on a transparent substrate is covered with a cover material at a distance, by using a measuring unit for irradiating a polarized light and then analyze the characteristics of the respective deposited layers of the sample, in accordance with the model corresponding to the sample and the measured result of the measuring unit.

Also, the present invention relates to a manufacturing method of an organic EL element, which is formed from a plurality of layers, step by step, in a plurality of film deposition chambers, and manufacturing equipment used in the method.

Also, the present invention relates to a sample analyzing method and a sample analyzing apparatus that measure the optical characteristics of a sample, in which multi-layer structure is deposited on a transparent substrate are covered with a cover material, by using a measuring unit for irradiating a polarized light and then analyze the characteristics of the respective deposited layers of the sample, in accordance with the model corresponding to the sample and the measured result of the measuring unit using a computer-readable recording medium, to enable the sample analyzing apparatus function.

2. Description of the Prior Art

Conventionally, in order to analyze the characteristics (a refractive index of a film, an extinction coefficient, a film thickness and the like) of a sample having a film, a measuring unit for measuring by irradiating a polarized light such as a polarimeter and an ellipsometer was used. For example, in the ellipsometer, the polarized light is inputted to the sample, and the changes in the polarization states of an incident light and reflected light are measured, thereby calculating an amplitude ratio ($\Psi$ psi) and a phase difference ($\Delta$ delta) as shown in FIG. 1A. It is impossible to determine unique combination of a film thickness (d), a refractive index (n), an extinction coefficient (k) of the film from the amplitude ratio and phase difference obtained by the ellipsometer. Therefore, in accordance with the assumption content (substrate type, a film thickness and the like) for the items of an analysis target sample inputted by a user, a model based on the sample structure is established, and the model and the measurement results of the ellipsometer are used to analyze the sample.

The specific analyzing procedure is as follows. At first, the amplitude ratio and the phase difference that are calculated from the model by a theoretical calculation and the amplitude ratio and the phase difference the measured by the ellipsometer are compared. Then, in such a way that the difference between them becomes minimal, a process for changing parameters of a dispersion formula related to the model and the film thickness in the model and the like is carried out (referred to as a fitting). The difference between them is usually calculated by the calculation that uses a least squares method. When the result obtained by the least squares method through the fitting is judged to become small to a certain degree, the refractive index and the extinction coefficient of the film are calculated from the values of the parameters in the dispersion formula at that time, and the film thickness at that time is selected as the film thickness of the respective layer of the sample.

Note that the construction of the model, the calculation based on the least squares method, the fitting and the like are typically carried out manually or automatically in accordance with a necessary program installed into a computer (refer to patent documents 1, 2).

[Patent Document 1] Japanese Laid Open Patent Application (JP-P 2002-340789)

[Patent Document 2] Japanese Laid Open Patent Application (JP-P 2002-340528)

An organic EL (Electroluminescence) element is a self light emitting device which has a basic multi-layer structure containing a lower electrode, several organic films, including an organic light emitting layer, and an upper electrode deposited on a substrate. Since a voltage is applied between the upper electrode and the lower electrodes, electrons are injected from a cathode side, formed on one of the electrodes into the organic layer. Holes are injected from an anode side formed on the other of electrode into the organic layer. Holes and electrodes are recombined in the organic light emitting layer, and the light is consequently emitted.

A manufacturing equipment of an organic EL element of a cluster type is known (for example, a patent document 3), as a manufacturing equipment of such an organic EL element. FIG. 2 is a schematic plan view showing the configuration of a conventional cluster type manufacturing equipment. In the drawing, 200 is the cluster type manufacturing equipment and is provided with two series of film forming cluster (apparatuses) 210, 220 and a sealing cluster 230. A substrate feeding chamber 241 is installed and linked to the film forming apparatus 210 on the feeding side, and receiving/sending chambers 242, 243 are installed and linked between the film forming apparatuses 210, 220 and the sealing cluster 230, respectively, and a discharging chamber 244 is installed and linked to the sending side of the sealing cluster 230. Feeding robots 211, 221 are placed inside the film forming apparatuses 210, 220, and a plurality of evaporating chambers 212, 213, 214, 222, 223 and 224 are installed around them. Then, inspecting chambers (for measuring the film thicknesses) 215, 225 are installed in the respective film forming apparatuses 210, 220, respectively.

A feeding robot 231 is placed also at the center of the sealing cluster 230. In the periphery thereof, a sealing substrate feeding chamber 232, an inspection chamber (for measuring a light emission characteristic) 233, a sealing chamber 234 and a spare vacuum chamber 235 are installed. Then, vacuum gates 1G are installed in the input ports of the respective evaporation chambers 212, 213, 214, 222, 223 and 224, and the output/input ports of the substrate feeding chamber 241, the receiving/sending chambers 242, 243, the sealing substrate feeding chamber 232 and the discharging chamber 244.

Here, in the film forming apparatuses 210, 220, the evaporating chambers 212, 213, 214, 222, 223 and 224 are intended to form the organic films (hole transport layers, light emitting layers (R, G and B) and electron feeding layers) and the upper electrodes, respectively. Vacuum evaporation apparatuses such as resistance heating types and the like are installed, and each of them has an evaporation source for heating and evaporating the evaporation material of each layer. An optical film thickness measuring units for actually measuring the deposited film thicknesses are installed in the inspection chambers 215, 225. Then, so as to enable the film thickness setup adjustment in the evaporating chambers in accordance with the inspection results in the inspection chambers 215, 225, the inspection chamber 215 and the respective evaporation chambers 212 to 214 or the inspection chamber 225 and the respective evaporation chambers 222 to 224 are connected through a data transmitting device (including transmission lines and transmitting/receiving apparatuses) 1P.

According to the foregoing manufacturing equipment, the substrate (ITO substrate), on which a pre-processing step and a washing operation are already performed, is fed into the substrate feeding chamber 241 and passed to the feeding robot 211 of the film forming apparatus 210. With the operation of the feeding robot 211, the evaporation is sequentially executed in the evaporating chambers 212, 213 and 214, and the film thicknesses of the deposited layers are measured in the inspecting chamber 215. The receiving/sending operation from the feeding robot 211 on the side of the film forming apparatus 210 to the feeding robot 221 on the side of the film deposition side 220 is carried out in the receiving/sending chamber 242. Then, in the film forming chamber 220, with the operation of the feeding robot 221, the evaporation is sequentially executed in the evaporating chambers 222, 223 and 224, and the film thicknesses of the deposited layers are measured in the inspecting chamber 225.

Concrete the example of the film forming step of this manufacturing equipment is disclosed, for example, the film deposition of a first color is carried out in the film forming apparatus 210, the hole transport layer that is common for each color is evaporated in the evaporating chamber 212, the light emission layer (B) is evaporated in the evaporating chamber 213, and the electron feeding layer (B) is evaporated in the evaporating chamber 214, respectively. Then, the film forming adjustment for a chromaticity compensation layer is carried out in accordance with the simulation of the light emission characteristic based on the measurement result (the measurement result in the inspecting chamber 215 is transmitted to the evaporating chamber 214, and the film thickness setting is carried out in the evaporating chamber 214). After that, the substrate is again fed into the evaporating chamber 214 or the different evaporating chamber (not shown), and in accordance with the adjusted setting film thickness, the chromaticity compensation layer composed of the electron feeding layers is formed.

After that, it is passed to the film forming apparatus 220, and the film deposition of a second color is carried out. The light emitting layer (G) is evaporated in the evaporation chamber 222. Next, the electron feeding layer (G) is evaporated in the evaporation chamber 223. After that, it is fed to the inspection chamber 225, and the deposited film thickness is measured. Then, the film forming adjustment for the chromaticity compensation layer is carried out in accordance with the simulation of the light emission characteristic based on the measurement result. After that, it is again fed into the evaporating chamber 223 or the different evaporating chamber (not shown), and the chromaticity compensation layer composed of the electron feeding layers is formed in accordance with the adjusted setting film thickness.

Then, after the upper electrode is finally evaporated in the evaporating chamber 224, the substrate is fed through the receiving/sending chamber 243 to the sealing cluster 230. In the sealing cluster 230, at first, it is fed to the inspection chamber 233, and the light emission characteristic is measured therein, and the fact that there is no chromaticity shift is checked. Then, the substrate, on which the organic films and the upper electrode are formed, and the sealing substrate fed from the sealing substrate feeding chamber 232 are both fed to the sealing chamber 234, and both of them are stuck to each other using adhesive material. An organic EL panel after the completion of the sealing is fed out through the discharging chamber 244 outside the apparatus. In addition to the manufacturing equipment of the cluster type as mentioned above, a manufacturing equipment of an in-line type where the film forming apparatus to which the evaporating chamber is linked and the sealing cluster are arranged in parallel is known.

[Patent Document 3] Japanese Laid Open Patent Application (JP-P 2005-322612)

Conventionally, in order to analyze the characteristics (the refractive index of the film, the extinction coefficient, the film thickness and the like) of the sample having the film, the polarimeter, the ellipsometer and the like have been used. For example, in the ellipsometer, the polarized light is inputted to the sample, and the changes in the polarization states of the incident light and reflected light are measured, thereby calculating the amplitude ratio ($\Psi$ psi) and the phase difference ($\Delta$ delta). Also, only by using the amplitude ratio and phase difference calculated by the ellipsometer, from only one set for the sample, it is impossible to calculate the refractive index (n) of the film, the extinction coefficient (k) and the film thickness (d). So, in accordance with the assumption content (the kind of the substrate, the film thickness and the like) for the items of the sample of the analysis target inputted by the user, the model based on the structure of the sample is established, and the model and the measurement results of the ellipsometer are used to analyze the sample.

The specific analyzing procedure is as follows. At first, the amplitude ratio and the phase difference that are calculated from the model by the theoretical calculation and the amplitude ratio and the phase difference that are calculated by the measurement of the ellipsometer are compared. Then, in such a way that the difference between them becomes minimal, the process for changing the parameter of the dispersion formula related to the model and the film thickness of the model and the like is carried out (referred to as the fitting). The difference between them is usually calculated by the calculation that uses the least squares method. When the result obtained by the least squares method through the fitting is judged to become small to a certain degree, the refractive index of the film and the extinction coefficient are calculated from the value of the parameter in the dispersion formula at that time, and the film thickness at that time is selected as the film thickness of the film of the sample.

Note that the preparation for the model, the calculation based on the least squares method, the fitting and the like are typically manually or automatically carried out in accordance with the necessary program by using the computer (refer to patent documents 4, 5).

A technique for using the foregoing ellipsometer for measuring the film thickness of the organic EL (Electro-Luminescence) element and the like is disclosed (for example, a patent document 6). The organic EL element has the basic structure where the lower electrode, the organic layer including the organic light emission function layer, and the upper electrode are deposited on the transparent substrate.

Since the voltage is applied between the upper electrode and the lower electrode of the organic EL element, the electrons are injected from the cathode side formed on one of the upper electrode and the lower electrode into the organic layer. The holes are injected from the anode side formed on the other of the upper electrode and the lower electrode into the organic layer, and they are again coupled in the organic light emission function layer in the organic layer, and the light is consequently emitted. After the organic films and the like are formed on the transparent substrate, the cover material for covering the organic layer and the like is stuck on the transparent substrate, and the organic EL element panel is completed and shipped as a product.

[Patent Document 4] Japanese Laid Open Patent Application (JP-P 2002-340789)

[Patent Document 5] Japanese Laid Open Patent Application (JP-P 2002-340528)

[Patent Document 6] Japanese Laid Open Patent Application (JP-P 2005-322612)

In the analysis that uses the ellipsometer as mentioned above, the kinds of the samples targeted for the analysis are various, which leads to the request desired to analyze the sample having the film that is not exposed to outside, in recent years. For example, in order to research and develop materials of an organic EL (OLED: Organic Light Emitting Diode) element, to which attention is paid as a next generation display, and in order to inspect a product, it is expected to analyze the organic films of the organic EL element in accordance with the analyzing method of using the foregoing ellipsometer. In particular, it is desired to be able to check whether or not the prototype organic EL element or the manufactured organic EL element has the structure according to a design, or if the structure is not based on the design, it is desired to be able to determine which of the points are defective. Also, it is desired to be able to check how the organic EL element is chronologically changed (deteriorated).

However, the organic EL element has the structure which contains an anode, the plurality of films (organic films) and the cathode deposited on the transparent substrate such as a glass substrate, and the films are covered with a sealing cap, and the inside is vacuum-sealed, or the rare gas and the like are filled inside the sealed space. For this reason, there is a problem that the method of irradiating the light towards the multi-layer film structure existing in the sealed space and properly obtaining the reflected light and then measuring the optical characteristics of the film using the ellipsometer becomes very difficult. Thus, there is a problem that in the present situation, it is impossible to check properly whether or not the manufactured organic EL element has the structure according to the design, which of the point is defective, and the chronological change and the like.

Also, even if the light can be irradiated onto the deposited film arranged inside the sealing cap, space (gap) exists between the sealing cap and the film. For this reason, depending on the gap dimension, the irradiation of the light causes an interference pattern. If the interference pattern is generated, there are problems that it takes a very long time to measure and that the values of the amplitude ratio ($\Psi$) and the phase difference ($\Delta$) which are calculated in accordance with the model have the minute amplitudes in the upper and lower directions as shown in FIG. 1B and the excellent analysis cannot be attained.

Moreover, because of the structure of the organic EL element, a plurality of reflection manners with regard to the light irradiated towards the film of the organic EL element are assumed, which results in a problem that the accurate analysis cannot be attained unless a plurality of the kinds with regard to the models to be used for the analysis are also prepared and the model corresponding to the reflection manner is suitably selected.

For example, in the case under the assumption that the light can be irradiated towards the film from the glass substrate side of the organic EL element, when the irradiated light is reflected on the boundary between the film and the gap, the plurality of reflection manners may be induced when the light is passed through the gap and reflected on the inner surface of the sealing cap. However, in such a case, the reflection manner among the foregoing plurality of reflection manners, to which the reflected light from the sample actually obtained by the ellipsometer belong, cannot be typically judged, which disables the selection of the kind of the model to be used for the analysis. For this reason, the actual analysis is required to carry out the vast amount of calculations by using all the kinds of the models so as to be able to consider all of the reflection manners and select the best calculation result from them as the analysis result. Thus, even if the organic EL element can be measured, there is a problem that the burden on the analyzing process is severe and the long time is needed until the analysis result is obtained. Note that the foregoing respective problems may occur in the case of analyzing the sample having the structure similar to the organic EL element, but other than the organic EL element. Also, even if the polarimeter is used as the measuring unit, the foregoing problems are similarly induced.

However, in the conventional manufacturing equipment, each time after the film deposition of each layer in corresponding evaporating chamber, a deposited multi-layer product is fed into the inspecting chamber, and the optical film thickness is measured, which requires the long time for the evaporation and inspection steps. Also, the deposited multi-layer product is required to be moved between the evaporating chamber and the inspecting chamber. Thus, there is a problem that the management burden of the vacuum state inside the apparatus becomes great. The optical film thickness measurement is executed in the inspecting chamber after the film deposition of each layer, thus, if an error in the film thickness exists, the film thickness adjustment for the chromaticity compensation layer is required to be carried out in the evaporating chamber in a next stage. Hence, there is a problem that the number of the steps is increased.

However, the technique noted in the patent document 6 only measures the film thickness after the film deposition of each film. Thus, there is a problem that the optical characteristic of the organic EL element panel at the shipping stage where the cover material is stuck on the transparent substrate cannot be measured. In particular, if the manufactured organic EL element panel has the structure according to the design or does not have the structure according to the design, it is desired to be able to determine which of the layers is defective. Moreover, it is required to consider the precise problem of deterioration with time of the optical characteristics of the organic EL element panel. Note that the patent document 4 and the patent document 5 do not disclose the means to solve the foregoing problems.

BRIEF SUMMARY OF THE INVENTION

The present invention has been made with the aim of solving the above-mentioned problems. It is therefore an object of the present invention to provide a sample analyzing method and a sample analyzing apparatus, which even for a sample structure such as an organic EL element, can surely obtain a light irradiation to and a reflected light from the film and consequently analyze the characteristics of the film that is not exposed to the outside ambient.

Another object of the present invention is to provide a sample analyzing method and a sample analyzing apparatus, which can remove an influence of an interference pattern and consequently execute an excellent analysis.

A further object of the present invention is to provide a sample analyzing method and a sample analyzing apparatus, which depending on a thickness dimension of a sample, can select a kind of a model to be used for an analysis and consequently attain an efficient process related to the analysis.

In order to solve the above-mentioned problems, a sample analyzing method according to the present invention is a sample analyzing method that measures optical characteristics of a sample, in which a multi-layer structure deposited on a transparent substrate are covered with a cover material with a certain gap, by using a measuring unit for irradiating a polarized light and analyzes the characteristics of respective deposited layers of the sample in accordance with a model corresponding to the sample and a measurement result of the measuring unit, and the sample analyzing method is characterized by containing: a step of irradiating the polarized light to the transparent substrate of the sample; a step of obtaining the light reflected on the sample; and a step of measuring a polarization state of the obtained light.

The sample analyzing method according to the present invention is characterized by containing: a step of preparing a first model where a gap layer and the deposited layer are stacked on each other and a second model where the layer related to the cover material, the gap layer and the deposited layer are stacked on each other; a step of receiving a thickness dimension of the sample that is measured by the measuring unit; and a step of selecting the first model and/or the second model as the model to be used for the analysis, in accordance with the received thickness dimension.

The sample analyzing method according to the present invention is characterized by containing: a step of preparing a first model where a gap layer and the deposited layer are stacked on each other, a second model where the layer related to the cover material, the gap layer and the deposited layer are stacked on each other, and a third model where the layer related to a peripheral atmosphere of the cover material, the layer related to the cover material, the gap layer and the deposited layer are stacked on each other, and then receiving a thickness dimension of the sample that is measured by the measuring unit; and a step of selecting at least one of the first model, the second model and the third model as the model to be used for the analysis, in accordance with the received thickness dimension, if the sample measured by the measuring unit has the transparent cover material.

A sample analyzing method according to the present invention is a sample analyzing method that measures optical characteristics of a sample, in which a multi-layer structure deposited on a substrate are covered with a cover material with a certain gap, by using a measuring unit for irradiating a polarized light and analyzes the characteristics of respective deposited layers of the sample in accordance with a model corresponding to the sample and a measurement result of the measuring unit, and the sample analyzing method is characterized by containing: a step of irradiating the polarized light to the cover material of the sample; a step of obtaining the light reflected on the sample; and a step of measuring a polarization state of the obtained light.

The sample analyzing method according to the present invention is characterized by containing: a step of preparing a first model where the layer related to the substrate and the deposited layer are stacked on each other and a second model where the layer related to a peripheral atmosphere of the substrate, the layer related to the substrate and the deposited layer are stacked on each other and then receiving a thickness dimension of the sample that is measured by the measuring unit; and a step of selecting the first model and/or the second model as the model to be used for the analysis, in accordance with the received thickness dimension, if the sample measured by the measuring unit has the transparent substrate.

The sample analyzing method according to the present invention is characterized by containing: a step of performing a fitting on each model, if a plurality of models to be used for the analysis are selected, and calculating a mean square error; and a model selection step of selecting a model related to a value of the minimal mean square error, or a model in which a value of the mean square error belonging to a range between a maximum value and a minimal value of a preset film thickness is minimal, from the plurality of models, wherein the value related to the model selected at the model selection step is used as an analysis result.

The sample analyzing method according to the present invention is characterized by containing a step of calculating an item equal to an item measured by the measuring unit, in accordance with the model to be used for the analysis, wherein the step carries out any of a first calculation process corresponding to an interference pattern appearing in the sample that is caused by the irradiation of the light and a second calculation process that does not correspond to the interference pattern, and analyzes the characteristics of the film by using a calculated result.

The sample analyzing method according to the present invention is characterized by containing: a step of comparing the magnitude between a standard distance and an gap distance from the film of the sample to the cover material, wherein if the gap distance is longer than the standard distance, the second calculation process is carried out.

The sample analyzing method according to the ninth invention is characterized by containing a step of changing the value of the standard distance.

A sample analyzing apparatus according to the present invention is a sample analyzing apparatus containing: a measuring unit that has irradiating means for irradiating a polarized light to a sample, in which films deposited on a transparent substrate are covered with a cover material with a certain gap, and means for obtaining the light reflected on the sample and measuring a polarization state of the light; and means for analyzing characteristics of the sample in accordance with a model corresponding to the sample and a measurement result of the measuring unit, and the sample analyzing apparatus is characterized by containing: means for storing a plurality of models whose structures are different from each other; means for receiving a thickness dimension of the sample to be measured; and means for selecting the model to be used for the analysis from the plurality of models, in accordance with the received thickness dimension.

A sample analyzing apparatus according to the present invention is a sample analyzing apparatus containing: a measuring unit that has irradiating means for irradiating a polarized light to a sample, in which films deposited on a transparent substrate are covered with a cover material with a certain gap, and means for obtaining the light reflected on the sample and measuring a polarization state of the light; and analyzing means for analyzing characteristics of the sample in accordance with a model corresponding to the sample and a measurement result of the measuring unit, and the sample analyzing apparatus is characterized by containing calculating means for calculating an item equal to an item measured by the measuring unit, in accordance with the model to be used for the analysis, wherein the calculating means is configured so as to carry out any of a first calculation process corresponding to an interference pattern appearing in the sample that is caused by the irradiation of the light and a second calculation process that does not correspond to the interference pattern, and the calculating means analyzes the characteristics of the film by using the result calculated by the calculating means.

The sample analyzing apparatus according to the present invention is characterized by containing: means for receiving an gap distance between the film of the sample and the cover material; and means for carrying out the magnitude comparison between the received gap distance and a standard distance, wherein if the gap distance is longer than the standard distance, the calculating means carries out the second calculation process.

In the present invention, since the light is irradiated towards the transparent substrate of the sample, the light transmitted through the transparent substrate can be surely applied to the deposited film, and the optical characteristics of the film can be measured by the measuring unit. For this reason, for the completed sample such as the organic EL element, whether or not it has the structure based on the design, which of the point is defective, whether or not the chronological change is generated and the like can be checked. It is noted that in order to irradiate the light towards the transparent substrate of the sample, it may be considered to place the sample on the stage of the measuring unit so that the transparent substrate is located on the upper side, or place the sample on the stage where the hole is made so that the transparent substrate is located on the lower side, or irradiate the light through the hole of the stage towards the transparent substrate. Also, the ellipsometer, the polarimeter and the like can be applied to the measuring unit.

In the present invention, in accordance with the thickness dimension of the sample of a measurement target, one or both of the first model and the second model which are prepared in advance are included in the model to be used for the analysis. Thus, the efficient analyzing process can be carried out without any use of the model diverged from the actual reflection manner in the sample. That is, the inventor of the present invention notes that the reflection manner related to the light which can be obtained by the measuring unit is limited to a certain degree, depending on the entire thickness of the sample. Consequently, at least one of the first model and the second model is included as the model corresponding to the reflection manner that can be assumed from the thickness dimension of the sample of the analysis target which is received as the setting target required to execute the analysis. As this result, the number of the models required to analyze can be throttled, and the calculation can be executed, thereby attaining the efficient analyzing process.

In the present invention, even if the cover material of the sample is transparent, the reflection manner related to the light that can be obtained by the measuring unit is limited depending on the entire thickness of the sample. Thus, as the model belonging to this limited range, at least any of the first to third models is included, and the analysis is executed, thereby enabling the efficient analyzing process to be attained.

In the present invention, if the cover material covering the film of the sample is transparent, by irradiating the light towards the cover material, the light transmitted through the cover material can be applied to the inner film, and the optical characteristics of the film can be measured by the measuring unit such as the ellipsometer. Thus, for the sample such as the organic EL element the following questions could be answered, whether or not it has the structure according to the design, which of the point is defective, whether or not the chronological change is generated and the like can be checked. It is noted that when the light is irradiated onto the cover material, the sample can be placed on the stage of the measuring unit so that the substrate is located on the lower side. Hence, the placement manner of the sample is stabilized.

In the present invention, when the substrate of the sample is transparent, even if the light is irradiated towards the cover material, the reflection manner related to the light that can be obtained by the measuring unit is limited depending on the entire thickness of the sample. Thus, as the model corresponding to the limited reflection manner, at least one of the first model and the second model is included and the analysis is executed. Hence, the analyzing process related to the model can be efficiently advanced.

In the present invention, when the plurality of models to be used for the analysis are selected, the fitting is performed on all of those models, and the mean square error related to the least squares method is calculated, and the value related to the model whose mean square error is minimal or the model having the lowest mean square error among the models that are reasonable for the structure is used for the analysis result. Thus, even if the plurality of models are used, the optimal analysis result can be obtained.

In the present invention, when the model corresponding to the sample where the interference pattern is generated by the irradiation of the light, the amplitude ratio ($\Psi$) and the phase difference ($\Delta$), which are calculated by the calculation from the model, have the upper and lower amplitudes. Thus, at such a time, depending on the situation, the calculation is executed by using any of the first calculation process corresponding to the interference pattern and the second calculation process that does not correspond to the interference pattern. Hence, the analysis result can be obtained correspondingly to the need of the user. For example, when the analysis result corresponding to the actual situation is obtained, the usual first calculation process corresponding to the interference pattern is executed, and when the reduction in the time necessary for the analyzing process is requested, the second calculation process that does not correspond to the interference pattern is executed.

In the present invention, the standard distance and the distance (gap distance) of the gap (gap) existing between the film and the cover material are compared with regard to the magnitude. If the gap distance is longer than the standard distance, the calculation based on the second calculation process is executed, therefore the automation for the calculation process selection based on the gap distance could be introduced. That is, which of the first calculation process and the second calculation process is used for the calculation is considered to be selected by an operator who considers the characteristics of the sample of the analysis target, the time that can be used for the analysis and the like. However, depending on the value of the gap distance, it is known that even if the light is irradiated onto the sample, the interference is not generated. Thus, it is possible to judge which of the calculation processes enables the process to be properly advanced, in accordance with the relation between the gap distance and the standard distance serving as the generation boundary of the interference. It is noted that as the value of the gap distance, it is preferable to use of the dimension defined by the specification of the sample targeted for the analysis. As the standard distance, the use of the value of about 100 μm that is the typical dimension where the interference pattern does not exist is preferable.

In the present invention, the value of the standard distance serving as the comparison standard with respect to the gap distance is changed. Thus, the judgment condition to determine which one of the first calculation process and the second calculation process will be used for the calculation can be properly changed after considering the sample characteristics of the various kinds, and the flexible condition setting can be executed correspondingly to the sample. That is, depending on a request level for the analysis, the second calculation process corresponding to the non-existence of the interference may be used instead of the first calculation process corresponding to the existence of the interference. Hence, the condition (standard distance) related to the selection of each process is designed to be able to be properly changed, which enables the analysis to be smoothly executed correspondingly to the situation.

In the present invention, when the analysis is started, the plurality of kinds of models corresponding to the sample having the transparent substrate are prepared (stored), and the model suitable for the analysis is selected from the plurality of models prepared on the basis of the thickness dimension of the received sample. Thus, the efficient analyzing process can be executed. That is, when the light is irradiated through the transparent substrate, the reflection manner corresponding to one model among the prepared models is induced, which enables the calculation based on the proper model without any use of the model diverged from the actual reflection manner in the sample.

In the present invention, the calculation process that is used in the model can use any of the first calculation process corresponding to the interference pattern or the second calculation process that does not correspond to the interference pattern. Thus, even if the sample of the analysis target has the characteristic that causes the interference pattern to be generated by the irradiation of the light, the analysis can be executed correspondingly to the requested analysis level. For example, when preference is given to the request that the analysis should be completed in a short time, the fine measurement is not required, which can reduce the time necessary for the measurement. Also, since the calculation is executed under the second calculation process, the reduction in the analysis time is attained.

In the present invention, if the received gap distance is longer than the standard distance, the second calculation process is executed. Thus, the operator is not required to indicate the first calculation process or second calculation process under which the calculation is executed, to the sample analyzing apparatus. Hence, the operational burden of the operator on the sample having the complex configuration can be decreased, thereby attaining the efficient analyzing process.

In the present invention, since the light is irradiated towards the transparent substrate of the sample, the light can be applied to the film located inside the cover material. Thus, the characteristics of the film can be surely measured.

In the present invention, at least one of the first model and the second model can be applied as the model to be used for the analysis. Thus, the model corresponding to the actual reflection manner can be used to carry out the efficient analysis.

In the present invention, when the cover material of the sample is transparent, at least one of the first to third models are included, and the analysis is carried out, which can attain the efficient analyzing process without any calculation using the model that does not correspond to the actual reflection manner.

In the present invention, when the cover material covering the film of the sample is transparent, since the light is irradiated towards the cover material, the light can be applied through the cover material into the film. Thus, the characteristics of the film can be surely measured.

In the present invention, for the light that is irradiated towards the cover material, the model corresponding to the assumed reflection manner is used to carry out the analysis. Thus, the useless calculation can be omitted as much as possible, which attains the efficient analyzing process.

In the present invention, even if the plurality of models to be used for the analysis are selected, the most suitable model can be pointed out in accordance with the calculated mean square error, and the excellent analysis result can be obtained.

In the present invention, any of the first calculation process corresponding to the interference pattern and the second calculation process that does not correspond to the interference pattern is used to carry out the calculation. Thus, even in the case of analyzing the sample in which the interference pattern appears, the analyzing means corresponding to the need of the user can be selected, thereby improving the convenience of the user.

In the present invention, if the gap distance between the film of the sample and the cover material is longer than the standard distance, the second calculation process is executed, which can automate the process selection related to the calculation and can decrease the measurement time and the analysis time.

In the present invention, since the value of the standard distance is changed, the judgment standard of the calculation process can be changed correspondingly to the request level for the analysis, and the setting specification can be provided finely correspondingly to the need of the user.

In the present invention, in accordance with the thickness dimension of the received sample, the model suitable for the analysis is selected from the plurality of kinds of models. Thus, the efficient analyzing process can be executed. In the present invention, the calculation process that uses the model uses any of the first calculation process corresponding to the interference pattern and the second calculation process that does not correspond to the interference pattern. Thus, even if the sample of the analysis target has the property that the interference pattern is generated by the irradiation of the light, the analyzing process corresponding to the requested analysis level can be advanced. In particular, when the second calculation process is selected, the time necessary for the calculation can be decreased.

In the present invention, if the received gap distance is longer than the standard distance, the second calculation process is automatically executed, which can reduce the operational burden of the operator and can smoothly advance the analyzing process.

The present invention has been made with the aim of solving the above-mentioned problems. It is therefore an object of the present invention to provide a manufacturing method that can manufacture an organic EL element having a higher performance in less steps by installing an optical film thickness measuring apparatus outside each film forming chamber and carrying out a film thickness control of each layer, and a manufacturing equipment which is used in the manufacturing method.

Another object of the present invention is to provide a manufacturing equipment that can measure the film thickness of the film deposition product without any physical disturbance, such as the film forming unit and the like, from outside the film forming chamber in which the film forming unit is placed, by installing the optical film thickness measuring apparatus on the side opposite to the deposition direction of the film deposition product and can make the design of the entire apparatus easy.

The manufacturing method of the organic EL element according to the present invention is the manufacturing method of the organic EL element in which the film depositions of the plurality of layers are gradually executed in the plurality of film forming chambers, and the manufacturing method is characterized in that the film thickness of the film deposition product is measured by the optical film thickness measuring apparatus installed outside each film forming chamber, and if the film thickness measured by the optical film thickness measuring apparatus achieves the preset film thickness, the film deposition product is fed to the film forming chamber installed in the next stage.

The manufacturing equipment of the organic EL element according to the present invention is the manufacturing equipment of the organic EL element in which the film depositions of the plurality of layers are gradually executed in the plurality of film forming chambers, and the manufacturing equipment is characterized in containing: the optical film thickness measuring apparatus that is installed outside each film forming chamber and measures the film thickness of the film deposition product; and the means for feeding the film deposition product to the film forming chamber installed in the next stage, if the film thickness measured by the optical film thickness measuring apparatus becomes the preset film thickness.

The manufacturing equipment of the organic EL element according to the present invention is characterized by further containing the film forming unit that is installed on the deposition direction side of the film deposition product and supplies a film deposition material, wherein the optical film thickness measuring apparatus is installed on the side opposite to the deposition direction of the film deposition product. The manufacturing equipment of the organic EL element according to the present invention is characterized by further containing the control means for controlling the film forming unit.

The manufacturing equipment of the organic EL element according to the present invention is characterized in that the optical film thickness measuring apparatus further contains: the means for calculating the film thickness deposition rate of the film deposition product; and the means for outputting the deviation between the calculated film thickness deposition rate and the preset film thickness deposition rate to the controller, wherein the control means is configured so as to control the film forming unit so that the output deviation becomes approximately zero.

The manufacturing equipment of the organic EL element according to the present invention is characterized in that the optical film thickness measuring apparatus is an ellipsometer, and the optical film thickness measuring apparatus contains; the means for calculating the optical constant of the film deposition product; and the means for outputting the deviation between the calculated optical constant and the preset optical constant to the control means, wherein the control means is configured so as to control the film forming unit so that the output deviation becomes approximately zero.

The manufacturing equipment of the organic EL element according to the present invention is characterized by further containing a transmission window that is obliquely installed on the side opposite to the deposition direction of the film deposition product in the film forming chamber and transmits an incident light from the optical film thickness measuring apparatus and a reflected light to the optical film thickness measuring apparatus. The manufacturing equipment of the organic EL element according to the present invention is characterized in that the optical film thickness measuring apparatus is the ellipsometer that uses a photo elastic modulator.

In the present invention, the manufacturing equipment of the organic EL element contains the plurality of film forming chambers for carrying out the film depositions of the plurality of layers. The optical film thickness measuring apparatus for measuring the film thickness of the film deposition product is installed outside of each film forming chamber. If the film thickness measured by this optical film thickness measuring apparatus becomes the preset film thickness, the feeding means feeds the film deposition product to the film forming chamber installed in the next stage. With such configuration, the inspection chamber dedicated to differently measure the film thickness is not required, which improves the manufacture speed. Also, since the film thickness is sequentially measured and controlled in the film forming chamber of each layer, the organic EL element having the higher property can be manufactured.

In the present invention, the film forming unit that is installed on the deposition direction side of the film deposition product and supplies the film deposition material is used. Then, the control means controls the film forming unit. On the other hand, the optical film thickness measuring apparatus is installed on the side opposite to the deposition direction of the film deposition product. In this way, the optical film thickness measuring apparatus is arranged on the side opposite to the deposition direction, and the film thickness is measured from the rear of the substrate.

In the present invention, the optical film thickness measuring apparatus calculates the film thickness deposition rate. Then, the deviation between the calculated film thickness deposition rate and the preset film thickness deposition rate is outputted to the control means. The control means controls the film forming unit so that the output deviation becomes approximately zero. Thus, it is possible to attain the film deposition based on the design, to manufacture the organic EL element having the higher performance, and to increase the yield.

In the present invention, the ellipsometer is used as the optical film thickness measuring apparatus. The ellipsometer calculates the optical constant of the film deposition product. Then, the deviation between the calculated optical constant and the preset optical constant is outputted to the control means. The control means is configured so as to control the film forming unit so that the output deviation becomes approximately zero. Thus, it is possible to attain the film deposition based on the design and also possible to manufacture the organic EL element having the higher performance and to increase the yield.

In the present invention, the transmission window to transmit the incident light from the optical film thickness measuring apparatus and the reflected light to the optical film thickness measuring apparatus is obliquely installed on the side opposite to the deposition direction of the film deposition product in the film forming chamber. Thus, the incident light can be inputted to the film deposition product through the transmission window, at the optimal angle in the film forming chamber. Also, the reflected light from the film deposition product can be obtained through the transmission window to the optical film thickness measuring apparatus.

In the present invention, the optical film thickness measuring apparatus is installed outside each film forming chamber, and the film thickness control of each layer is carried out, which can improve the manufacture speed with less steps. Also, the film thickness is sequentially measured and controlled in the film forming chamber of each layer. Thus, the organic EL element having the higher performance can be manufactured.

In the present invention, the optical film thickness measuring apparatus is installed on the side opposite to the deposition direction, and the film thickness is measured from the rear of the substrate. Also, since the film forming unit and the like are installed in the deposition direction of the film deposition product in the film forming chamber, it is difficult to reserve the space for the film thickness measurement. However, the measurement is carried out from the side opposite to the deposition direction. Thus, the arrangement layout of the film forming unit in the deposition direction and the like can be freely designed.

In the present invention, the optical film thickness measuring apparatus is used to calculate the film thickness deposition rate of the film deposition product, and the control means controls the film forming unit so that the output deviation becomes approximately zero. Thus, it is possible to attain the film deposition based on the design, to manufacture the organic EL element having the higher performance and to increase the yield.

In the present invention, it is configured that the optical constant of the film deposition product is calculated and the control means controls the film forming unit so as to make the output deviation approximately zero. Thus, it is possible to attain the film deposition based on the design, to manufacture the organic EL element having the higher performance and to increase the yield.

In the present invention, the transmission window to transmit the incident light from the optical film thickness measuring apparatus and the reflected light to the optical film thickness measuring apparatus is obliquely installed on the side opposite to the deposition direction. Thus, the incident light can be inputted to the film deposition product through the transmission window, at the optimal angle in the film forming chamber. Also, the reflected light from the film deposition product can be obtained through the transmission window to the optical film thickness measuring apparatus. Hence, the present invention provides the excellent effects.

The present invention has been proposed in view of the above-mentioned situations. It is therefore an object of the present invention to provide a sample analyzing method and a sample analyzing apparatus, which measure the polarization state of the light from the transparent substrate side and measure the polarization state of the light from the cover material side and analyze the characteristics of the respective deposited layers, in accordance with the measurement results and the polarization states obtained from the substrate side model and the cover side model, and can consequently analyze the sample at the higher precision, as compared with the measurement from one direction, and a computer-readable recording medium to make the manufacturing equipment function.

Another object of the present invention is to provide a sample analyzing apparatus, in which from each of a route hole direction of a sample stage penetrated by a route hole and an upper direction of the sample stage, light is irradiated towards the transparent substrate side or cover material side by a measuring unit, and the polarization state of the reflected light is measured and analyzed by the measuring unit, and the sample can be consequently analyzed in a shorter time and in a simpler manner.

A sample analyzing method according to the present invention is a sample analyzing method that measures optical characteristics of a sample, in which films deposited on a transparent substrate are covered with a cover material, by using a measuring unit for irradiating a polarized light and analyzes the characteristics of respective deposited layers of the sample in accordance with a model corresponding to the sample and a measurement result of the measuring unit, and the sample analyzing method is characterized by containing: a substrate side measuring step of irradiating the light from the transparent substrate side by means of the measuring unit and measuring a polarization state of the light reflected on the sample; a cover side measuring step of irradiating the light from the cover material side by means of the measuring unit and measuring the polarization state of the light reflected on the sample; a calculating step of reading a substrate side model in a case of a measurement from a transparent substrate side and a cover side model in a case of a measurement from the cover material side, which are stored in advance, and calculating the polarization state of the light based on the substrate side model and the polarization state of the light based on the cover side model, respectively; and an analyzing step of analyzing the characteristics of the respective deposited layers, on the basis of the polarization state of the light based on the substrate side model and the polarization state of the light based on the cover side model, which are calculated by the calculating step, and the polarization state measured by the substrate side measuring step and the polarization state measured by the cover side measuring step.

The sample analyzing method according to the present invention is characterized in that the analyzing step calculates the film thicknesses and the optical constant of the respective deposited layers by carrying out the fitting, on the basis of the polarization state of the light based on the substrate side model and the polarization state of the light based on the cover side model, which are calculated by the calculating step, and the polarization state measured by the substrate side measuring step and the polarization state measured by the cover side measuring step.

The sample analyzing method according to the present invention is characterized in that the analyzing step contains: an error calculating step of calculating a mean square error, on the basis of the polarization state of the light based on the substrate side model calculated by the calculating step and the polarization state measured by the substrate side measuring step, and the polarization state of the light based on the cover side model calculated by the calculating step and the polarization state measured by the cover side measuring step; a changing step of changing parameters of the cover side model and the substrate side model until the mean square error calculated by the error calculating step becomes a predetermined value or less or a minimal value; and an optimal value calculating step of calculating the film thicknesses and the optical constant of the respective deposited layers if the mean square error becomes the predetermined value or less or the minimal value, through the changing step.

The sample analyzing method according to the present invention is characterized in that the cover side model and the substrate side model are represented by using a plurality of kinds of dispersion formulas indicating a wavelength dependence of a dielectric constant; and the changing step changes the parameters of the cover side model and the substrate side model with regard to each of the plurality of kinds of dispersion formulas, until the mean square error calculated by the error calculating step becomes the predetermined value or less or the minimal value.

A sample analyzing apparatus according to the present invention is a sample analyzing apparatus that contains: a measuring unit for irradiating a polarized light and measuring optical characteristics of a sample in which films deposited on a transparent substrate are covered with a cover material; and an analyzer for analyzing characteristics of the respective deposited layers of the sample in accordance with a model corresponding to the sample and a measurement result of the measuring unit, and the sample analyzing apparatus is characterized by containing: a sample stage where the sample is placed and a part thereof is penetrated by a route hole serving as a route of the light; substrate side measuring means for irradiating the light from the route hole direction of the sample stage or from an upper direction of the sample stage towards the transparent substrate side by means of the measuring unit and measuring the polarization state of the light reflected on the sample by means of the measuring unit; cover side measuring means for irradiating the light from the upper direction of the sample stage or from the route hole direction towards the cover material side by means of the measuring unit and measuring the polarization state of the light reflected on the sample by means of the measuring unit; calculating means for reading a substrate side model in a case of a measurement from a transparent substrate side and a cover side model in a case of a measurement from the cover material side, which are stored in advance in a storage device, through the analyzer and calculating the polarization state of the light based on the substrate side model and the polarization state of the light based on the cover side model, respectively; and analyzing means for analyzing the characteristics of the respective deposited layers through the analyzer, on the basis of the polarization state of the light based on the substrate side model and the polarization state of the light based on the cover side model, which are calculated by the calculating step, and the polarization state measured by the substrate side measuring means and the polarization state measured by the cover side measuring means.

The sample analyzing apparatus according to the present invention is characterized in that the analyzing means is configured so as to calculate the film thicknesses and the optical constant of the respective deposited layers by carrying out the fitting, on the basis of the polarization state of the light based on the substrate side model and the polarization state of the light based on the cover side model, which are calculated by the calculating means, and the polarization state measured by the substrate side measuring means and the polarization state measured by the cover side measuring means.

The sample analyzing apparatus according to the present invention is characterized in that the analyzing means contains: error calculating means for calculating a mean square error, on the basis of the polarization state of the light based on the substrate side model calculated by the calculating means and the polarization state measured by the substrate side measuring means, and the polarization state of the light based on the cover side model calculated by the calculating means and the polarization state measured by the cover side measuring means; changing means for changing parameters of the cover side model and the substrate side model, until the mean square error calculated by the error calculating means becomes a predetermined value or less or a minimal value; and optimal value calculating means for calculating the film thicknesses and the optical constant of the respective deposited layers if the mean square error becomes the predetermined value or less or the minimal value, through the changing means.

The sample analyzing apparatus according to the present invention is characterized in that the storage device stores a plurality of kinds of dispersion formulas indicating wavelength dependences of dielectric constants with regard to the cover side model and the substrate side model, and the changing means is configured so as to read the plurality of kinds of dispersion formulas stored in the storage device, until the mean square error calculated by the error calculating means becomes the predetermined value or less or the minimal value, and change the parameters of the cover side model and the substrate side model with regard to each of the dispersion formulas.

The sample analyzing apparatus according to the present invention is characterized in that the measuring unit is installed on each of the upper side and the lower side through the sample stage.

The sample analyzing apparatus according to the present invention is characterized by further containing moving means for moving the measuring unit to the upper side or lower side of the sample stage.

A computer-readable recording medium according to the present invention is a recording medium wherein optical characteristics of a sample in which films deposited on a transparent substrate is covered with a cover material is measured by a measuring unit for irradiating a polarized light, and the characteristics of the respective deposited layers of the sample is analyzed by a computer, in accordance with a model corresponding to the sample and a measurement result of the measuring unit, and the recording medium is characterized in that the computer is instructed to execute: a substrate side measuring step of receiving a result when the polarization state of the light reflected on the sample is measured, in a case that the light is irradiated by the measuring unit from the transparent substrate side; a cover side measuring step of receiving a result when the polarization state of the light reflected on the sample is measured, in a case that the light is irradiated by the measuring unit from the cover material side; a calculating step of reading a substrate side model in the case of the measurement from the transparent substrate side and a cover side model in the case of the measurement from the cover material side, which are stored in advance, and calculating the polarization state of the light based on the substrate side model and the polarization state of the light based on the cover side model, respectively; and an analyzing step of analyzing the characteristics of the respective deposited layers, on the basis of the polarization state of the light based on the substrate side model and the polarization state of the light based on the cover side model, which are calculated by the calculating step, and the polarization state received by the substrate side measuring step and the polarization state received by the cover side measuring step.

In the present invention, at first, the light is irradiated from the transparent substrate side by the measuring unit, and the polarization state of the light reflected on the sample is measured. On the other hand, the light is irradiated from the cover material side located oppositely to the transparent substrate by the measuring unit, and the polarization state of the light reflected on the sample is measured. In response to the measurements from both of the directions, the analyzer reads the substrate side model in the case of the measurement from the transparent substrate side that is stored in advance, and reads the cover side model in the case of the measurement from the cover material side. The analyzer calculates the theoretical polarization state of the light based on the substrate side model and the theoretical polarization state of the light based on the cover side model, respectively.

Then, the analyzer carries out the fitting, on the basis of the polarization state of the light based on the calculated substrate side model, the polarization state of the light based on the calculated cover side model, the polarization state measured from the substrate side, and the polarization state measured from the cover side, and consequently analyzes the sample, for example, calculates the film thicknesses and the optical constant of the respective deposited layers and the like. With such configuration, the consideration of both data from the cover side and the substrate side enables the sample to be analyzed at the higher precision, as compared with the case of using only the data from one direction.

In the present invention, the analyzer calculates the mean square error by using the least squares method, on the basis of the polarization state of the light based on the calculated substrate side model and the polarization state measured from the substrate side, and the polarization state of the light based on the calculated cover side model and the polarization state measured from the cover side. Next, the analyzer changes the parameters of the cover side model and the substrate side model, until the calculated mean square error on the substrate side becomes the predetermined value or less or the minimal value. Then, the analyzer is configured so as to calculate the film thicknesses and the optical constant of the respective deposited layers when the mean square error becomes the predetermined value or less or the minimal value. Thus, the fitting based on both of the data from the cover side and the substrate side can be executed, thereby obtaining the result of the higher reliability.

In the present invention, the cover side model and the substrate side model are represented by using the dispersion formula indicating the wavelength dependence of the dielectric constant, and the plurality of dispersion formulas are stored. Then, until the calculated mean square error becomes the predetermined value or less or the minimal value, the plurality of kinds of dispersion formulas are sequentially read, and the parameters of the cover side model and the substrate side model are changed for each of the dispersion formulas. In this way, in view of the existence of the plurality of kinds of dispersion formulas, the parameters are changed for each dispersion formula, and the mean square error that becomes the predetermined value or less or the minimal value is calculated, which can obtain the result of the higher reliability based on the more optimal dispersion formula.

In the present invention, the sample analyzing apparatus that contains the measuring unit and the analyzer has the sample stage on which the sample is placed. In this sample stage, the part thereof is penetrated by the route hole serving as the route of the light, in order to enable the measurement from both of the cover side and the substrate side. Then, from the route hole direction of the sample stage or the upper direction of the sample stage, the light is irradiated towards the transparent substrate side by the measuring unit, and the polarization state of the light reflected on the sample is measured by the measuring unit. Reversely, from the upper direction of the sample stage or the route hole direction, the light is irradiated towards the cover material side by the measuring unit, and the polarization state of the light reflected on the sample is measured by the measuring unit. That is, from the upper direction of the sample stage, or from the route hole direction below the sample stage, both surfaces of the substrate side and the cover side are measured.

Here, the measuring unit is installed through the sample stage on each of the upper side and the lower side. In addition, the moving means moves the measuring unit to the upper side or lower side of the sample stage. Then, the analyzer analyzes the sample by carrying out the fitting, on the basis of the polarization state of the light based on the calculated substrate side model, the polarization state of the light based on the calculated cover side model, the polarization state measured from the substrate side, and the polarization state measured from the cover side. Thus, the work for turning over the sample can be omitted, and earlier obtain the analysis result.

In the present invention, the polarization state is measured from the transparent substrate side, and the polarization state is measured from the cover material side. Then, the fitting is carried out by calculating the polarization states obtained from the respective models on the cover side and the substrate side and then using the measurement and calculation data from both of the directions. Thus, the sample can be analyzed at the higher precision, as compared with the case of using only the data from one direction.

In the present invention, the analyzer calculates the mean square error, on the basis of the polarization state of the light based on the calculated substrate side model, the polarization state measured from the substrate side, and the polarization state of the light based on the calculated cover side model and the polarization state measured from the cover side. Then, until the calculated mean square error on the substrate side becomes the predetermined value or less or the minimal value, the parameters of the cover side model and the substrate side model are changed. Then, when the mean square error becomes the predetermined value or less or the minimal value, the film thicknesses and the optical constant of the respective deposited layers are calculated. Thus, the fitting based on both of the data on the cover side and the substrate side can be executed, which can obtain the result of the higher reliability.

In the present invention, in view of the existence of the plurality of dispersion formulas, the parameters are changed for each of the dispersion formulas, and the mean square error that becomes the predetermined value or less or the minimal value is calculated, which can obtain the result of the high reliability based on the more optimal dispersion formula.

In the present invention, in order to enable the measurements from both of the cover side and the substrate side, the sample stage whose part is penetrated by the route hole serving as the route of the light is placed. Then, on the basis of the polarization states of the lights based on the cover side model and the substrate side model, and the polarization states measured from the both of the directions, the fitting is carried out, and the sample is consequently analyzed, which can omit the work for turning over the sample and earlier obtain the analysis result. As this result, the larger number of samples can be analyzed in a short time. Also, when the measuring unit is moved by the moving means, it is not necessary to install a pair of measuring units in the upper and lower directions, and only one measuring unit is adequate. Thus, the cost of the sample analyzing apparatus can be reduced. Hence, the present invention provides the excellent effects.

The above and further objects and features of the invention will more fully be apparent from the following detailed description with accompanying drawings.

BRIEF DESCRIPTION OF THE SEVERAL VIEWS OF THE DRAWINGS

FIG. 2 is a schematic plan view showing a configuration of a conventional cluster type manufacturing equipment.

FIG. 7 is a schematic view showing an example of a setting menu.

FIGS. 34A and B are explanation views showing a model at a time of a measurement from a cover material side.

FIG. 41 is a block diagram showing a configuration of a sample analyzing apparatus according to an eleventh embodiment.

FIGS. 42A to 42C are flowcharts showing a procedure for calculating a mean squares error by using a plurality of dispersion formulas.

DESCRIPTION OF THE PREFERRED EMBODIMENTS

First Embodiment

Figure 1A:
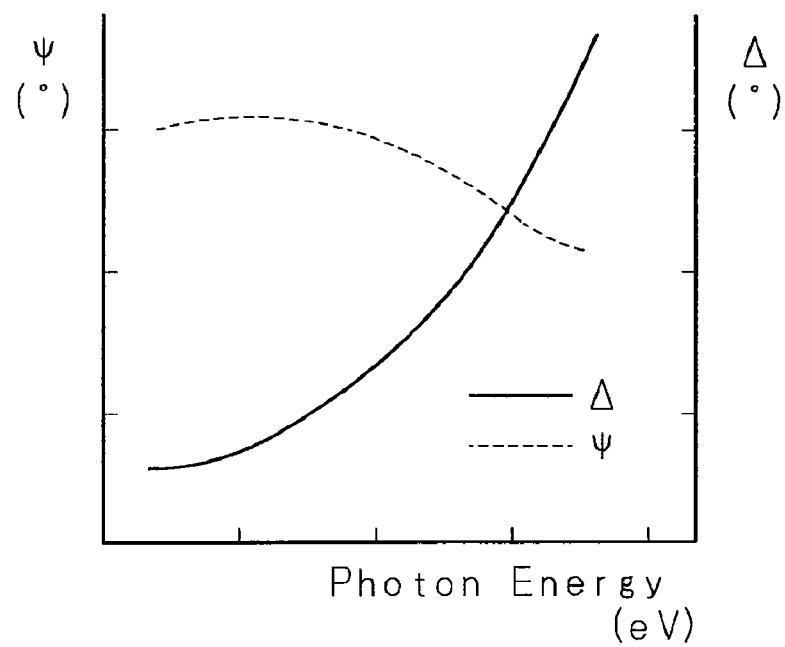
FIG. 1A is a graph showing an example of measurement results of an amplitude ratio and a phase difference.
Figure 1B:
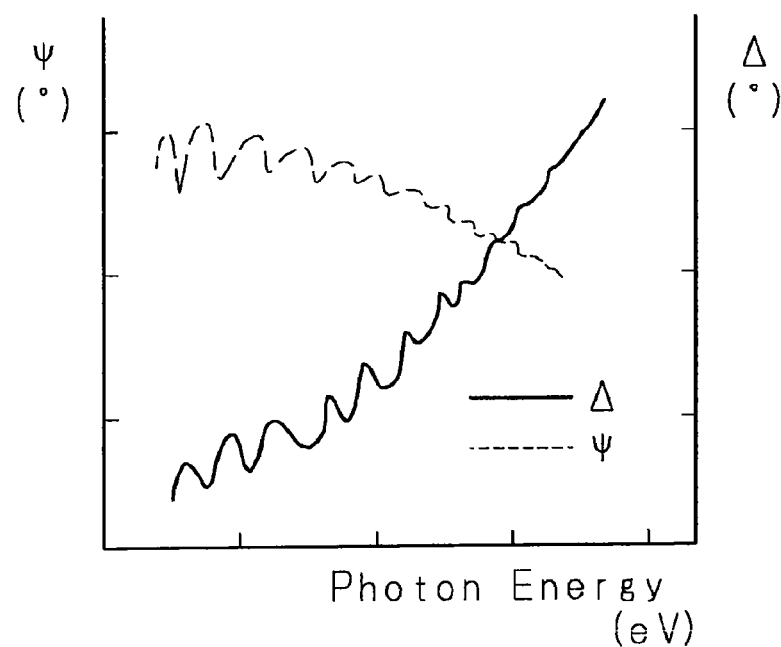
FIG. 1B is a graph showing values of minute amplitudes caused by an interference pattern.
Figure 3:
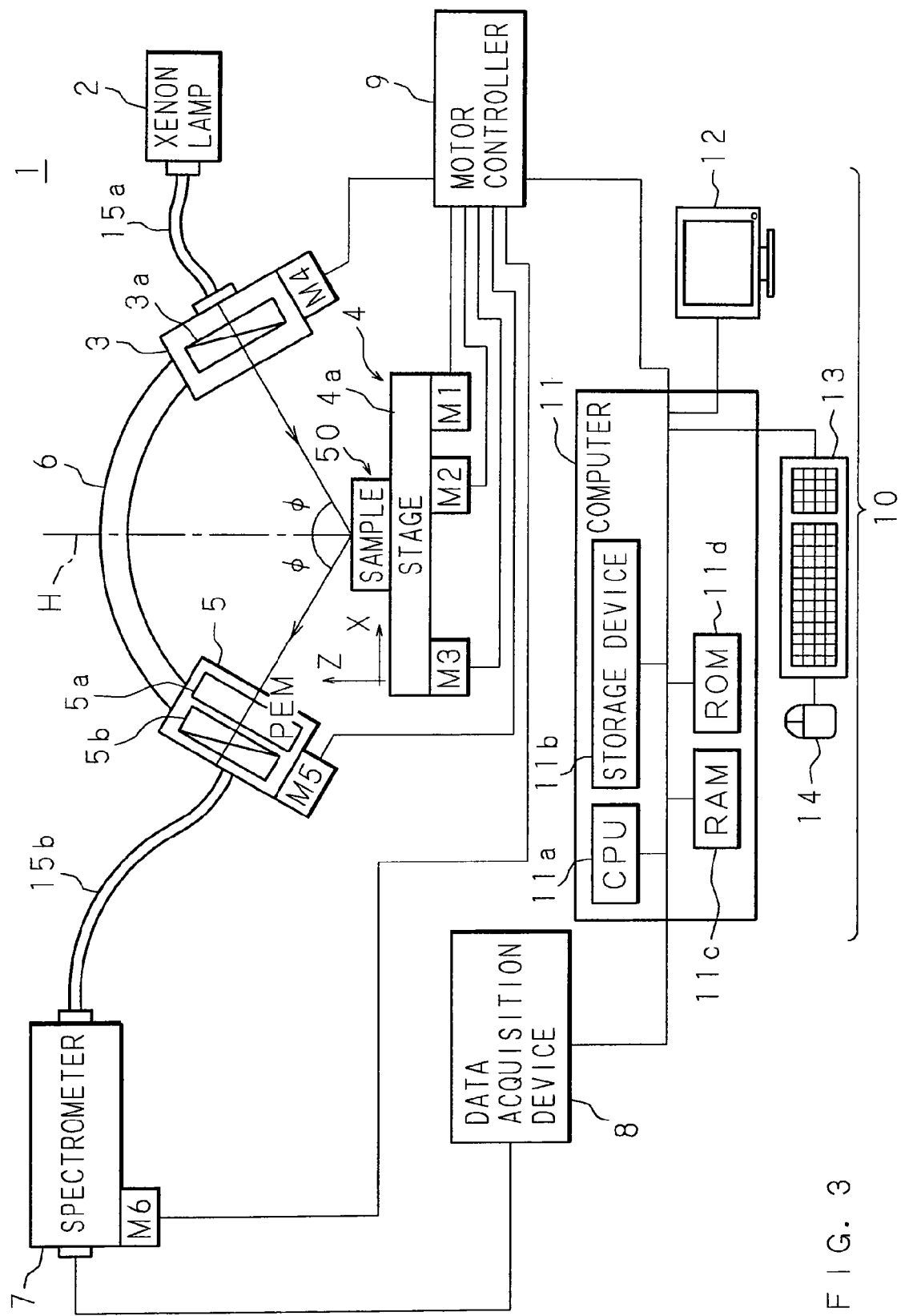
FIG. 3 is an entire configuration view of a sample analyzing apparatus according to an embodiment of the present invention.

FIG. 3 is a schematic view showing an entire configuration of a sample analyzing apparatus 1 including an ellipsometer (corresponding to a measuring unit) according to the embodiment of the present invention. The sample analyzing apparatus 1 irradiates a polarized light to a sample in which a multi-layer structure (plurality of films) are deposited, and obtains the light reflected on the sample, and then measures the polarization state of the reflected light and consequently analyzes the characteristics of the respective deposited layers (hereafter, film layers) in accordance with this measurement result and the model based on the sample structure. In this embodiment, a case where an organic EL element 50 as the sample is analyzed by the sample analyzing apparatus 1 is explained. Note that in the sample analyzing apparatus 1, a polarimeter can be used instead of the ellipsometer, as the measuring unit.

Figure 4A:
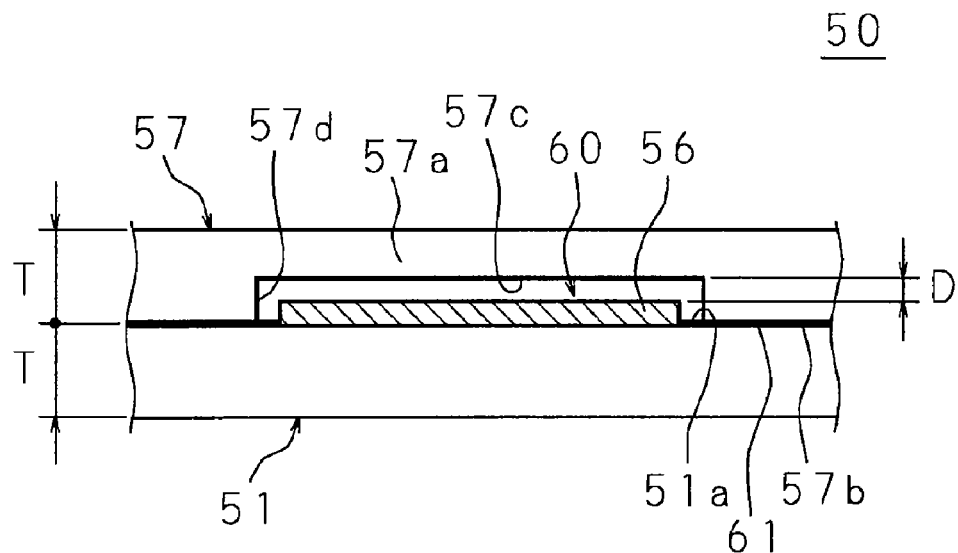
FIG. 4A is a schematic sectional view showing a structure of an organic EL element (production type) serving as a sample.

FIG. 4A shows an example of the organic EL element 50 that is an analysis target. This organic EL element 50 belongs to a production type, and this has the appearance where two glass substrates plates are stuck to each other. In the structure of the organic EL element 50, an organic film 56 is formed on one surface 51a of a glass substrate 51 (corresponding to a transparent substrate) serving as one glass plate material. On the other hand, a concave portion 57d for accommodating the organic film 56 is formed on a cover glass 57 (corresponding to a cover material) serving as the other glass plate material, and a surface 57b containing the concave portion 57d is adhered through an adhesive 61 to the one surface 51a of the glass substrate 51, and both of them are integrated. Note that the inside of the concave portion 57d sealed by the sticking between the glass substrate 51 and the cover glass 57 vacuum is made in order to protect the organic film 56, or rare gas (for example, nitrogen gas) is sealed therein.

Figure 4B:
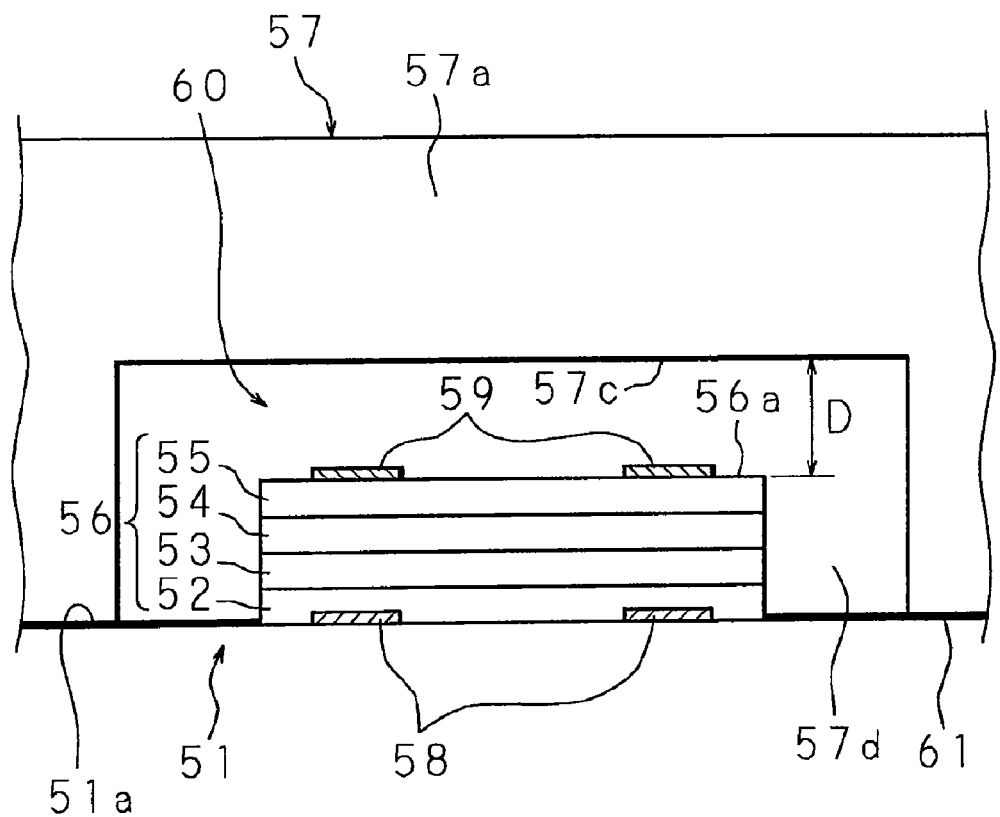
FIG. 4B is a sectional view in which a main portion of the organic EL element (production type) is enlarged.

FIG. 4B shows the detailed structure of the organic film 56 accommodated in the concave portion 57d. In the organic film 56, on an anode (ITO) 58 that is a transparent electrode arranged on the one surface 51a of the glass substrate 51 having the transparent property, a total of 4 layers composed of: a hole transport layer 52, an emitting layer 53, a hole blocking layer 54 and an electron transport layer 55 are sequentially stacked (piled). Also, in the organic film 56, a cathode 59 is arranged on a surface 56a opposite to the cover glass 57.

The organic film 56 is accommodated in the concave portion 57d at an gap (interval), and there is a space 60 from a cover portion 57a of the cover glass 57 for covering the surface 56a of the organic film 56. A thickness dimension D of the space 60 (a vertical dimension to an inner surface 57c of the cover portion 57a from the surface 56a of the organic film 56, and this corresponds to an gap distance) is various depending on the specification of the organic EL element 50. Typically, the thickness dimension D is set in a range between 10 μm and 400 μm, in most cases. Note that in the glass substrate 51 and the cover glass 57, the thickness T of 0.5 mm, 0.7 mm or 1.1 mm is used in many cases (0.7 mm is the most typical thickness). Thus, the entire thickness (2T) of the organic EL element 50 typically has the dimension in the range between 1.0 mm and 2.2 mm.

The sample analyzing apparatus 1 for analyzing the organic film 56 of the organic EL element 50 of the foregoing structure is configured as shown in FIG. 3, and it is roughly classified into a portion of a measurement analysis group and a drive group portion. The sample analyzing apparatus 1 is configured such that as the portion of the measurement analysis group, a xenon lamp 2 and a light irradiator 3 are connected through a first optical fiber cable 15a, and the light of a polarization state is irradiated onto the sample (organic EL element 50) placed on a stage 4 (sample table), and the light is inputted to the sample, and the light reflected from the sample is acquired by a light obtainer 5. The light obtainer 5 is connected through a second optical fiber cable 15b to a spectrometer 7. The spectrometer 7 carries out a measurement for each wavelength and transmits the measurement result as an analog signal to a data acquisition device 8. The data acquisition device 8 converts the analog signal into a necessary value and transmits to a computer 10, and the analysis is carried out by the computer 10.

Also, in the sample analyzing apparatus 1, as the drive group portion, a first motor M1 to a sixth motor M6 are installed in the stage 4, the light irradiator 3, the light obtainer 5 and the spectrometer 7, respectively. Since the drives of the respective motors M1 to M6 are controlled by a motor controller 9 connected to the computer 10, the stage 4, the light irradiator 3, the light obtainer 5 and the spectrometer 7 are changed to the suitable positions and poses corresponding to the measurements. The motor controller 9 performs the drive control on the respective motors M1 to M6 in accordance with an indication outputted by the computer 10. Note that in the sample analyzing apparatus 1, the portion corresponding to the ellipsometer is the range mainly constituted by the xenon lamp 2, the light irradiator 3, the stage 4, the light obtainer 5, the spectrometer 7, the data acquisition device 8, the motor controller 9 and the motors M1 to M6.

The foregoing respective portions of the sample analyzing apparatus 1 will be detailed below in turn. At first, the xenon lamp 2 serves as the light source, and generates a white light including a plurality of wavelength components and then sends the generated white light through the first optical fiber cable 15a to the light irradiator 3.

The light irradiator 3 is arranged on a rail 6 having a shape of a half circular arc and has a polarizer 3a therein. Then, the white light is polarized by the polarizer 3a, and the light of the polarization state is irradiated onto the sample. Also, the light irradiator 3 is moved along the rail 6 because the fourth motor M4 is driven, and an angle (incident angle φ) for a vertical line H of a stage surface 4a of the stage 4 with respect to the irradiated light is made adjustable.

The stage 4 is slidably arranged on a movement rail portion (not shown), and the drives of the first motor M1 to the third motor M3 enable the stage 4 to be moved in an X-direction and a Y-direction in FIG. 3 (directions orthogonal to the paper surface of FIG. 3) and a Z-direction serving as a height direction, respectively. The movement of the stage 4 enables the portion, at which the light is inputted to the sample, to be suitably changed, and the surface analysis of the sample is made possible. Note that the stage surface 4a on which the sample of the stage 4 is placed is blacked in order to protect the reflection of the light.

Figure 5:
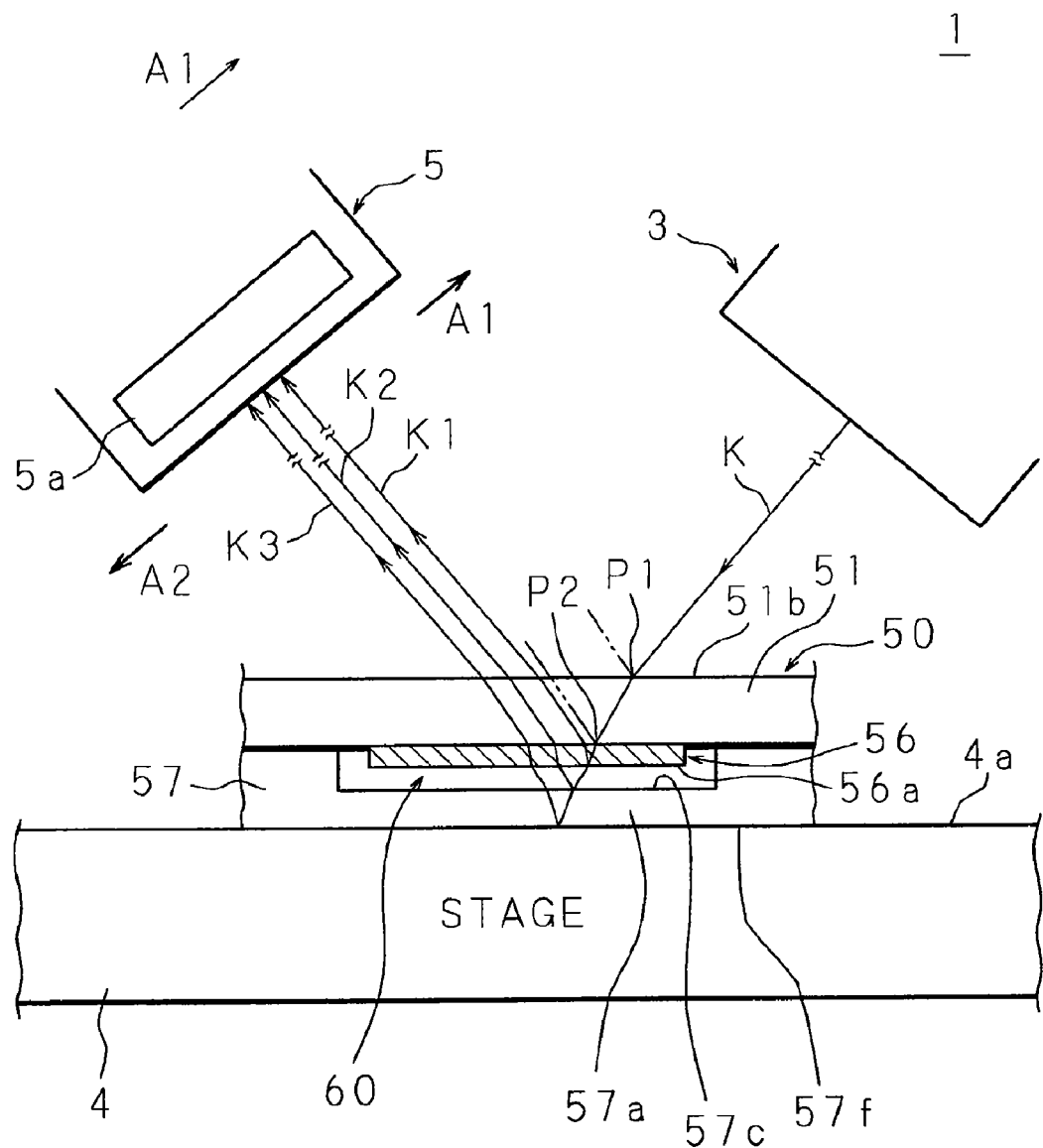
FIG. 5 is a schematic view showing an arrangement when an irradiation is applied to a glass substrate of the organic EL element.

In this embodiment, in order to emit the light to the organic film 56 covered with the cover glass 57 of the organic EL element 50, as shown in FIG. 5, in such a way that an outer surface 57f of the cover portion 57a of the cover glass 57 is brought into contact with the stage surface 4a of the stage 4, the upper portion and the lower portion are turned over, and the organic EL element 50 is placed on the stage 4. Since in this situation, the light irradiator 3 irradiates the light, the light is inputted from a rear 51b of the glass substrate 51 of the organic EL element 50, and passed through the transparent glass substrate 51 and sent to the organic film 56. Note that in FIG. 5, the illustrations of an anode 58 and the cathode 59 of the organic EL element 50 are omitted (FIG. 2A and FIG. 12 which will be illustrated later are similar).

Also, the light obtainer 5 obtains the light reflected from the sample (organic EL element 50) and measures the polarization state of the obtained light. The light obtainer 5 is arranged on the rail 6 similarly to the light irradiator 3, and a PEM (Photo Elastic Modulator) 5a and an analyzer (analyzing unit) 5b are built therein, and the light reflected from the sample is guided through the PEM 5a to the analyzer 5b. Also, the light obtainer 5 can be moved in arrows A1, A2 directions in FIG. 5 along the rail 6 in accordance with the drive of the fifth motor M5. Basically, it is controlled by the motor controller 9 so that in linkage with the movement of the light irradiator 3, a reflection angle φ and an incident angle φ become equal. Note that the PEM 5a built in the light obtainer 5 obtains an elliptical polarization from a straight polarization because the acquired light is phase-modulated at a certain frequency (for example, 50 kHz). Also, the analyzer 5b selectively obtains and measures the polarization from the various polarizations which are phase-modulated by the PEM 5a.

A reflection mirror, a diffraction grating, a photo multiplier (PMT: Photo Multiplier Tube), a control unit and the like are built in the spectrometer 7. Then, the light sent through the second optical fiber cable 15b from the light obtainer 5 is reflected by the reflection mirror and guided to the refractive grating. The refractive grating changes the angle through the sixth motor M6 and varies the wavelength of the output light. The light advanced to the inside of the spectrometer 7 is amplified by PMT, and even if the light amount is small, the measured signal (light) is made stable. Also, the control unit carries out the process for generating an analog signal corresponding to the measured wavelength and sending to the data acquisition device 8. Note that if the polarimeter is used in the measuring unit, the configuration of the combination of photo diode arrays (PDA) is also possible.

The data acquisition device 8 calculates the amplitude ratio $\Psi$ and the phase difference $\Delta$ with regard to the polarization state (a p-polarization and an s-polarization) of the reflected light in accordance with the signal from the spectrometer 7 and sends the calculated result to the computer 10. Note that as for the amplitude ratio $\Psi$ and the phase difference $\Delta$, the relation of the following equation (1) is established for an complex reflection coefficient Rp of the p-polarization and an complex reflection coefficient Rs of the s-polarization.

$$Rp/Rs = \tan\Psi \cdot \exp(i \cdot \Delta) \tag{1}$$

However, i is an imaginary unit (hereafter, similarly). Also, Rp/Rs is referred to as a ratio of the complex reflection coefficients $\rho$.

Also, the computer 10 of the sample analyzing apparatus 1 analyzes the sample in accordance with the amplitude ratio $\Psi$ and the phase difference $\Delta$ of the polarization state, which are obtained by the data acquisition device 8, and the model corresponding to the sample, and also controls the movement of the stage 4 and the like.

The computer 10 itself is provided with a computer body 11, a display 12, a keyboard 13 and a mouse 14 (input apparatus) and the like. In the computer body 11, a CPU 11a, a storing apparatus (hereafter, a storage device) 11b, a RAM 11c and a ROM 11d are connected through an inner bus. The CPU 11a carries out the various processes with regard to the computer 10, which will be described later, in accordance with various computer programs stored in the storage unit 11b. The RAM 11c transiently stores the various data and the like with regard to the processes, and the ROM 11d stores the content related to the functions of the computer 10 and the like.

Note that the storage unit 11b of the computer 10 stores in advance the various programs, such as a computer program for a sample analysis, a computer program for a movement control of the stage 4, and the like. Also, the storage unit 11b stores: data of various menu images to be displayed on the display 12; a known data related to the samples; model patterns of structures different from each other; a plurality of dispersion formulas used to prepare the models; prepared models; reference data corresponding to various samples; standard values to be used in a comparing process related to interference patterns; and the like.

With regard to the analysis of the sample (organic EL element 50), the computer 10 analyzes the refractive indexes and the extinction coefficients as the optical characteristics of the respective film layers (52 to 55) constituting the organic film 56 of the organic EL element 50 and also analyzes the film thicknesses of the respective film layers (52 to 55) and the like.

Specifically, the computer 10 uses a modeling program that is stored in advance in the storage unit 11b, if a complex refractive index of a peripheral atmosphere composed of the glass substrate 51, the cover glass 57 and the organic EL element 50 and the like is already known from the measured amplitude ratio and phase difference $\Delta$. Then, the model corresponding to the items of the sample set by a user and the material structure of the organic EL element 50 is prepared and stored in the storage unit 11b, and the model stored at the analysis stage is used to calculate the film thicknesses and the complex refractive indexes of the respective film layers 52 to 55 of the organic film 56. As for a complex refractive index N, when the film layer to be analyzed is assumed to have a refractive index n and an extinction coefficient k, the relation of the equation (2) represented by the following optical equation is established.

$$N = n - ik \tag{2}$$

Also, when an incident angle is assumed to be $\phi$ and a wavelength of a light irradiated by the light irradiator 3 is assumed to be $\lambda$, as for the amplitude ratio $\Psi$ and the phase difference $\Delta$ that are outputted by the data acquisition device 8 and measured by the ellipsometer, with regard to the film thicknesses d, the refractive indexes n and the extinction coefficients k of the film layers 52 to 55 to be analyzed, the relation of the following equation (3) is established.

$$(d, n, k) = F(\rho) = F(\Psi(\lambda, \phi), \Delta(\lambda, \phi)) \tag{3}$$

Note that the computer 10 uses the film thicknesses of the film layers 52 to 55 to be analyzed and the dispersion formula indicating the wavelength dependence of a complex dielectric constant having a plurality of parameters and carries out the process (fitting) for changing the film thicknesses, the parameters of the dispersion formula and the like, so as to minimize the difference between a model spectrum ($\Psi_M(\lambda_i)$, $\Delta_M(\lambda_i)$) obtained by a theoretical calculation from the stored model and a measurement spectrum ($\Psi_E(\lambda_i)$, $\Delta_E(\lambda_i)$) related to the measurement result outputted by the data acquisition device 8. Note that one example of an application dispersion formula is indicated by the following equation (4).

$$\varepsilon = \varepsilon_\infty + \frac{(\varepsilon_s - \varepsilon_\infty)\varpi_t^2}{\varpi_t^2 - \varpi^2 + i\Gamma_0\varpi} + \frac{\varpi_p^2}{-\varpi^2 + i\Gamma_D\varpi} + \sum_{j=1}^{2} \frac{f_j \varpi_{oj}^2}{\varpi_{oj}^2 - \varpi^2 + i\gamma_j\varpi} \tag{4}$$

In the equation (4), $\in$ on the left side represents a complex dielectric constant, and $\in_\infty$, $\in_s$ represent dielectric constants, and $\Gamma_0$, $\Gamma_D$, $\gamma_j$ represent damping factors, and $\omega_{oj}$, $\omega_t$, $\omega_p$ represent angular frequencies (an oscillator frequency, a transverse frequency, and a plasma frequency). Note that $\in_\infty$ is a high frequency dielectric constant, and $\in_s$ is a static dielectric constant. Also, as for the complex dielectric constant $\in$ (corresponding to $\in(\lambda)$) and the complex refractive index N (corresponding to N($\lambda$), the relation of the following equation (5) is established.

$$\in(\lambda) = N^2(\lambda) \tag{5}$$

Note that, when the fitting is simply explained, in the case that the organic EL element 50 is measured, let us suppose that T measurement data pairs are Exp (i=1, 2 ..., T) and T model calculation data pairs are Mod (i=1, 2 ..., T). Then, when the measurement error is considered to have a normal distribution and when a standard deviation is assumed to be $\sigma_i$, a mean square error $\chi^2$ obtained from the least squares method is calculated from the following equation (6). Note that P is the numeral of the parameters. When the value of the mean square error $\chi^2$ is small, this implies that the coincidence degree between the measurement result and the prepared model is high. Thus, when a plurality of models are compared, the model having the smallest value of the mean square error $\chi^2$ corresponds to the best model.

$$\chi^2 = [1/(2T - P)] \sum_{i=1}^{T} (\text{Exp}_i - \text{Mod}_i)^2 / \sigma_i^2 \qquad (6)$$

The series of the processes related to the sample analysis executed by the computer 10 as mentioned above are defined by the computer program for the sample analysis which is stored in the storage unit 11b. This computer program includes a process for displaying a menu to set the film thickness and the like as the condition items of the model prepared correspondingly to the physical characteristics of the sample on a screen of the display 12, and the like.

Also, in the sample analyzing apparatus 1 according to this embodiment, the model types (the structures of the models) preliminarily prepared so as to be able to cope with the plurality of reflection manners in the sample are stored in the storage unit 11b. The structures of those model types are read out and used for the analysis, in accordance with the process defined by the computer program (modeling program) stored in the storage unit 11b.

That is, in this embodiment, in order to measure the organic EL element 50 in the manner as shown in FIG. 5, as the manner that a light (beam) K irradiated onto the organic EL element 50 is reflected, 3 kinds are typically assumed. The first manner is the case that the beam K inputted to the organic EL element 50 is reflected on the boundary (the portion corresponding to the surface 56a of the organic film 56) between the organic film 56 and the space 60 (an optical path of a reflected beam K1 in FIG. 5). The second manner is the case that the beam K is transmitted through the organic film 56 and the space 60 and reflected on the inner surface 57c of the cover glass 57 (an optical path of a reflected beam K2 in FIG. 5). The third manner is the case that it is transmitted through the transparent cover glass 57 and reflected on the boundary (the portion where the outer surface 57f of the cover glass 57 and the stage surface 4a of the stage 4 are in contact with each other) between the cover glass 57 and the stage 4 (an optical path of a reflected beam K3 in FIG. 5).

Actually, as shown in FIG. 5, Note that, although the reflection at a point P1 on the glass substrate surface, the reflection at a point P2 serving as the boundary between the glass substrate 51 and the organic film 56, and the multiple reflection are included, since the reflections at the points P1, P2 are not directly related to the selection of the model to be used in the analysis, their treatments are omitted in this embodiment. Also, the beam K and the reflected lights K1 to K3 and the like are refracted at the time of the input to the glass substrate 51, the organic film 56 and the like and also refracted at the time of the output. However, at this time, the angles of the input case and the output case are equal. Moreover, whether or not all of the reflected lights K1 to K3 including the multiple reflection are measured depends on the thickness dimension of the sample. Thus, the sample analyzing apparatus 1 selects even the kind of the model to be used for the analysis, in accordance with the thickness dimension of the sample.

Figure 6A:
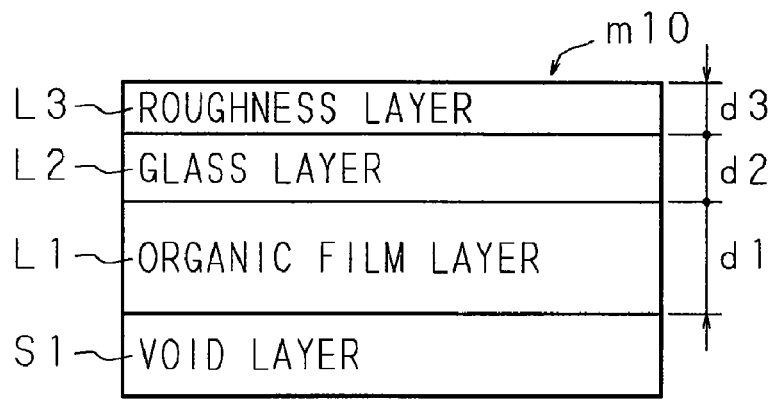
FIG. 6A is a schematic view showing a model of a structure corresponding to a reflected beam K1 of FIG. 5.

In the reflection manners of the 3 kinds as mentioned above, the layers through which the lights are transmitted are different from each other. Thus, as for the model to be used for the analysis, the model having the structure corresponding to the reflection manner in the actual measurement is required to be selected. FIG. 6A shows a model m10 of the structure corresponding to the reflected beam K1 in FIG. 5. The model m10, since corresponding to the reflection on the organic film 56, is configured such that the space 60 located below the organic film 56 is defined as a void layer (gap layer), and an organic film layer L1 (corresponding to the organic film 56), a glass layer L2 (corresponding to a portion without any surface roughness of the glass substrate 51) and a roughness layer L3 (a portion corresponding to the surface roughness of the glass substrate 51) are stacked on a void layer S1 (to be regarded as a substrate).

Figure 6B:
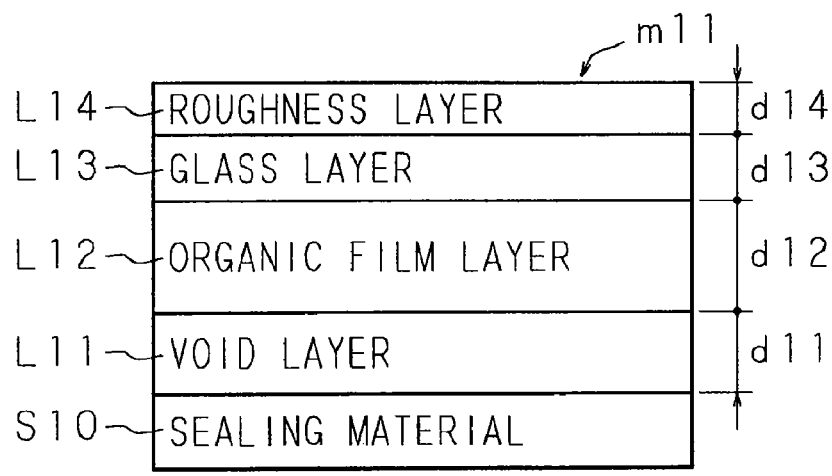
FIG. 6B is a schematic view showing a model of a structure corresponding to a reflected beam K2 of FIG. 5.

FIG. 6B shows a model m11 of the structure corresponding to the reflected beam K2 in FIG. 5. The model m11, since corresponding to the reflection on the inner surface 57c of the cover glass 57, is configured such that the material (sealing material) constituting the cover glass 57 is regarded as the substrate, and a void layer L11 (corresponding to the gap layer of the space 60), an organic film layer L12 (corresponding to the organic film 56), a glass layer L13 (corresponding to the portion without any surface roughness of the glass substrate 51) and a roughness layer L14 (the portion corresponding to the surface roughness of the glass substrate 51) are stacked on its sealing material S10 (corresponding to the layer related to the cover material).

Figure 6C:
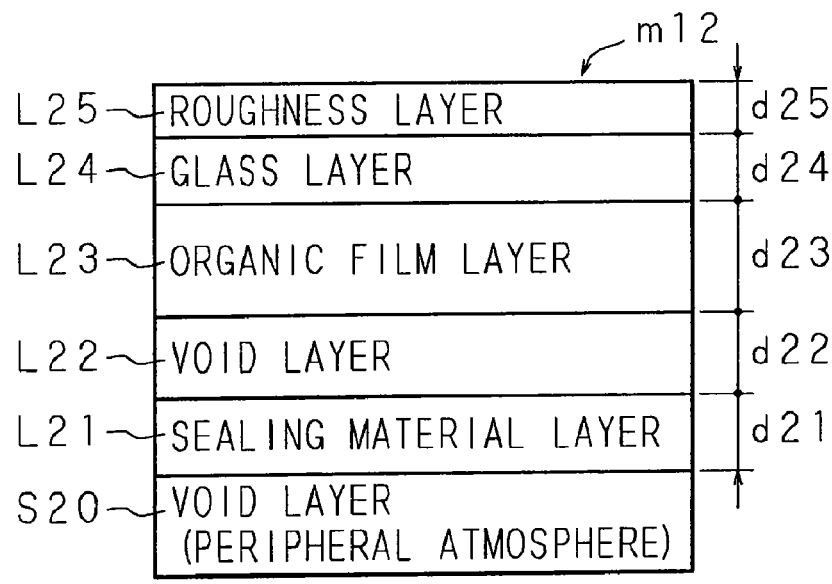
FIG. 6C is a schematic view showing a model of a structure corresponding to a reflected beam K3 of FIG. 5.

Moreover, FIG. 6C shows a model m12 of the structure corresponding to the reflected beam K3 in FIG. 5. The model m12, since corresponding to the reflection on the boundary surface between the cover glass 57 and the stage 4, is configured such that the medium (corresponding to the void layer in the space existing between the cover glass 57 and the stage 4, in FIG. 5) constituting the peripheral atmosphere below the cover glass 57 is regarded as the substrate, and a void layer L21 (corresponding to the layer of the material constituting the cover glass 57), a void layer L22 (corresponding to the gap layer of the space 60), an organic film layer L23 (corresponding to the organic film 56), a glass layer L24 (corresponding to the portion without any surface roughness of the glass substrate 51) and a roughness layer L25 (the portion corresponding to the surface roughness of the glass substrate 51) are stacked on its void layer (peripheral atmosphere) S20 (substrate).

Note that in the foregoing respective models m10, m11 and m12, the organic film layers L1, L12 and L23 are simply represented as one film layer in which the respective film layers 52 to 55 shown in FIG. 4B are combined. The organic film layers L1, L12 and L23 in the actual modeling are assumed such that the hole transport layer 52, the emitting layer 53, the hole blocking layer 54 and the electron transport layer 55 are deposited (laminated) similarly to the organic film 56 of the organic EL element 50, and the film thicknesses corresponding to the respective film layers 52 to 55 are set. In this way, the modeling corresponding to the respective film layers 52 to 55 enables the analysis of the characteristics of the respective film layers 52 to 55 included in the organic film 56.

In the sample analyzing apparatus 1, in order to select the model of the structure to be used for the analysis from the foregoing respective models m10, m11 and m12, the thickness dimension of the sample is included in the setting items received from the user for the sample of the analysis target in the preparation stage at the time of the sample measurement. In the sample analyzing apparatus 1, as the setting items for the sample of the analysis target in the preparation stage, the thickness dimension of the sample together with the kind of the substrate, the film thickness and the like is received by the input of the user, and the model to be used in the analysis is selected from the m10, m11 and m12, in accordance with the thickness dimension.

The relation between the thickness dimension of the sample and the measurable reflected light will be described below. If the thickness dimension of the sample of the analysis target is 2.2 mm or more, the reflection direction of the reflected beam K3 is dislocated and deviated from the measurement range of the light obtainer 5. For this reason, in the sample analyzing apparatus 1, if the thickness dimension of the sample is 2.2 mm or more, the reflected beam K3 cannot be measured by the light obtainer 5. Thus, as the structure of the model to be used for the analysis, the model m10 and the model m11 in FIG. 6A are selected.

Also, if the thickness dimension of the sample is between 1.0 mm and 2.2 mm, there is a possibility that all of the reflected lights K1 to K3 belong to the measurement range of the light obtainer 5. For this reason, in the sample analyzing apparatus 1, if the thickness dimension of the sample is between 1.0 mm and 2.2 mm, as the structure of the model to be used for the analysis, all of the models m10, m11 and m12 corresponding to the reflected lights K1 to K3 are selected.

Moreover, even if the thickness dimension of the sample is 1.0 mm or less, there is a possibility that all of the reflected lights K1 to K3 belong to the measurement range of the light obtainer 5. For this reason, the sample analyzing apparatus 1 selects all of the models m10, m11 and m12 corresponding to the reflected lights K1 to K3, as the structure of the model to be used for the analysis, if the thickness dimension of the sample is 1.0 mm or less. Note that depending on the material quality of the sample, there is a case where only the reflected beam K1 or only the two reflected lights K1, K2 belong to the measurement range. In this case, only the model m10, or the two models m10, m11 may be selected by the sample analyzing apparatus 1. Note that after the selection of the model kind, the sample analyzing apparatus 1 establishes the specific model to be used for the analysis under the model structure selected in accordance with the input items from the user.

Also, as another one feature of the process content defined by the computer program stored by the sample analyzing apparatus 1 according to this embodiment, the fact that the calculation process for calculating the amplitude ratio ($\Psi$) and the phase difference ($\Delta$) could be executed by two calculation methods for the model to be used in the analysis is listed. The first calculation process is to faithfully perform the calculation from the model used in the analysis and then obtain the calculation result (the amplitude ratio ($\Psi$) and the phase difference ($\Delta$)) corresponding to the measurement range of the sample. Also, the second calculation process is to perform the calculation on the amplitude in accordance with the model used in the analysis and then quickly obtain the calculation result. The sample analyzing apparatus 1 compares the thickness dimension D (corresponding to the gap distance) of the space 60 of the organic EL element 50 shown in FIGS. 4A and B serving as the analysis target with the standard value (corresponding to the standard distance) stored in the storage unit 11b of the computer 10 with regard to the distance value (magnitude) and determines the first calculation process or second calculation process under which the calculation is executed.

In the sample analyzing apparatus 1, with regard to the organic EL element 50 of the analysis target in the measurement preparation stage, the setting items received from the user include the thickness dimension D (the value based on the specification of the organic EL element 50) of the space 60 and the standard value. Then, if the thickness dimension D is greater than the standard value, the second calculation process is executed, and if the thickness dimension D is the standard value or less, the first calculation process is executed. Also, the second calculation process suitably averages the values, which are theoretically obtained from the model selected in accordance with the items inputted in the measurement preparation stage, by using the known calculation method. Thus, the graph related to the amplitude ratio ($\Psi$) and the phase difference ($\Delta$) which are obtained from the model exhibits the smooth curve. Even if the model serving as the analysis target is based on the sample in which the irradiation of the light results in the generation of the interference pattern, the calculation is executed without any precise correspondence to the interference pattern. For this reason, the time related to the calculation process can be made shorter than that of the first calculation process, and the time necessary for the measurement becomes short. On the other hand, since the first calculation process carries out the calculation faithful to the model, similarly to the conventional case, if the model serving as the analysis target corresponds to the sample in which the irradiation of the light results in the generation of the interference pattern, the calculation is executed correspondingly to the interference pattern. Hence, the analysis time becomes long, and the measurement time becomes also long.

In the sample analyzing apparatus 1 having the foregoing configuration, the series of the process procedures according to the method (sample analyzing method) for analyzing the organic EL element 50 shown in FIGS. 4A and B will be described below in accordance with flowcharts of FIGS. 8A and B. At first, the organic EL element 50 is placed on the stage 4 of the sample analyzing apparatus 1, as shown in FIG. 5 (S1).

Next, the sample analyzing apparatus 1 receives the input of the item necessary for the analysis through the keyboard 13 or mouse 14 from the user, in order to set the condition (S2). In receiving the item, in the sample analyzing apparatus 1, a setting menu 20 shown in FIG. 7 is displayed on the display 12. On the setting menu 20, correspondingly to the structure of the organic EL element 50 in FIGS. 4A and B, a thickness input column 21 of the space 60, an input column 22 of the film thickness related to the organic film 56, and an input column 23 related to the substrate (the cover glass 57) are installed. In particular, with regard to the input column 21 of the thickness of the space (gap), an input column 21a of the value (void) based on the specification of the organic EL element 50 and an input column 21b of the standard value related to the judgment of the first calculation process or second calculation process is installed. Note that although in the setting menu 20 of FIG. 7, the input of the film thickness is simplified to indicate only the input column 22, the input column is actually installed for each layer on the basis of the kind of the organic film layer.

In the organic EL element 50, the fact that if the thickness dimension D of the space 60 was smaller than 100 μm, the interference pattern was expected to occur was known from the previous research. For this reason, as the standard value, 100 μm is preferably set. Note that the setting menu 20 receives other items (a measurement point, an incident angle φ, a thickness of the glass substrate 51, a thickness of the cover glass 57, and the like) which are not shown in FIG. 7.

Then, the sample analyzing apparatus 1 judges whether the thickness dimension (2T) of the organic EL element 50 (sample) is 1.0 mm or less, or in a range between 1.0 mm and 2.2 mm, or 2.2 mm or more, on the basis of the thickness (T) of the glass substrate 51 in the input items and the thickness (T) of the cover glass 57 (refer to FIG. 4A) (S3).

If the thickness dimension (2T) is judged to be 1.0 mm or less (S3: 1.0 mm or less), the sample analyzing apparatus 1 selects the models m10 to m12 as the model structure to be used for the analysis (S4). Also, if the thickness dimension (2T) is judged to be in the range between 1.0 mm and 2.2 mm (S3: between 1.0 mm and 2.2 mm), the sample analyzing apparatus 1 selects the models m10 to m12 of FIGS. 6A to C as the model structure to be used for the analysis. Moreover, if the thickness dimension (2T) is judged to be 2.2 mm or more (S3: 2.2 mm or more), the sample analyzing apparatus 1 selects the models m10, m11 of FIGS. 6A and B as the model structure to be used for the analysis (S6).

Note that after the model selection, the sample analyzing apparatus 1 sets the model for the analysis corresponding to the item inputted under the structure of the selected model. The structure of the model to be used for the analysis in the foregoing judgment process is based on the reflection manner (refer to FIG. 5) of the analysis target sample. Thus, this contributes to the decrease in the process burden such as the stages (S10 to S12) of the later analysis processes and the like.

In the sample analyzing apparatus 1, so as to properly emit the light to the sample (organic EL element 50) placed on the stage 4 and enable the obtainment of the reflected light having the value adequate for the measurement, a tentative irradiation is executed to carry out a height adjustment of the stage 4 and the like (S7). After the height adjustment of the stage 4, in the sample analyzing apparatus 1, as the normal irradiation to measure the organic EL element 50 (sample), the light of the polarization state is irradiated onto the organic EL element 50 (S8), and the reflected lights (K1 to K3) reflected from the glass substrate 51 are obtained to measure the polarization state of the light (the amplitude ratio $\Psi_E$, the phase difference $\Delta_E$) (S9). Note that the $\Psi_E$ indicates the measured amplitude ratio, and the $\Delta_E$ indicates the measured phase difference.

Also, the sample analyzing apparatus 1 calculates the amplitude ratio $\Psi_M$ and the phase difference $\Delta_M$ in the range corresponding to the measurement range in accordance with the model set under the selected structure (S10). At this time, the sample analyzing apparatus 1 compares the input thickness dimension D of the space 60 with the standard value and calculates the amplitude ratio $\Psi_M$ and the phase difference $\Psi_M$ in the first calculation process or second calculation process. Here, the $\Psi_M$ indicates the amplitude ratio calculated from the model, and the $\Delta_M$ indicates the phase difference calculated from the model. Note that the sample analyzing apparatus 1 performs the foregoing calculation on all of the models, if there are the plurality of selected models.

Figure 10:
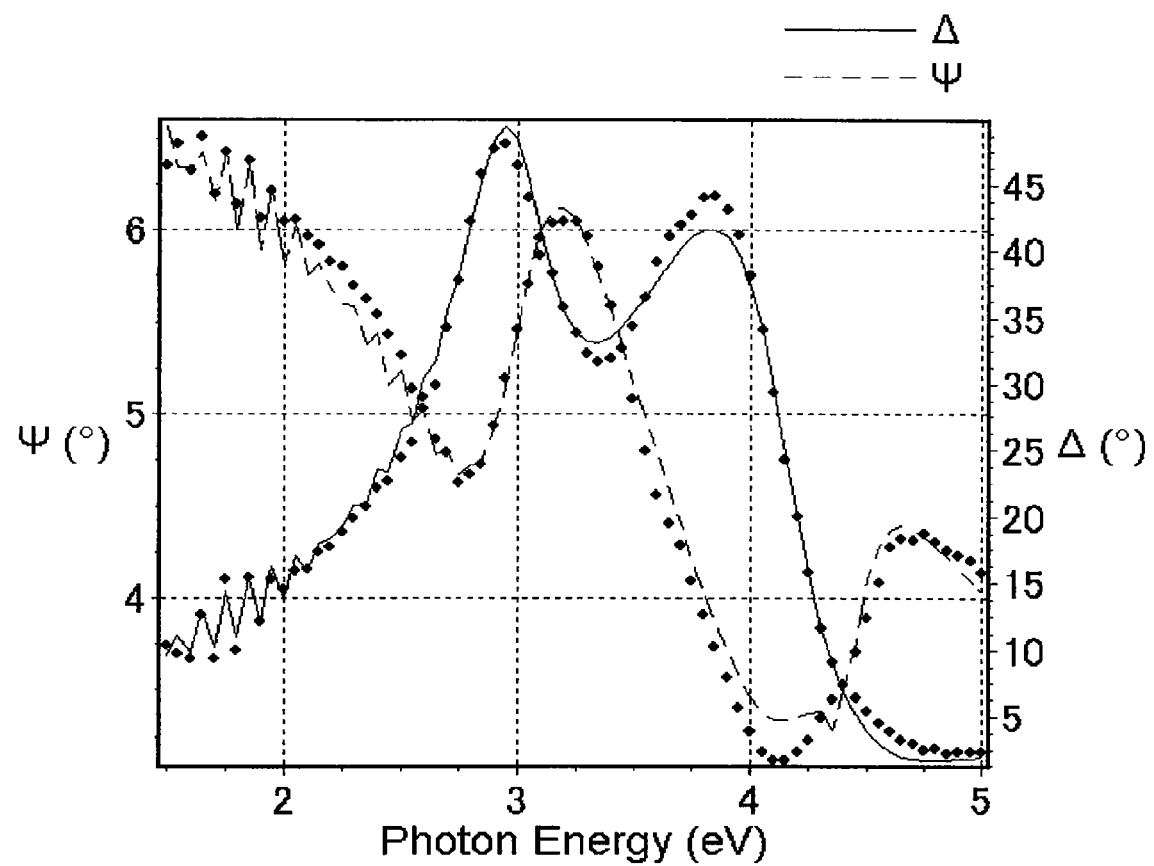
FIG. 10 is a graph showing a measurement result when a light is irradiated from a glass substrate to a sample (organic EL element) in which a thickness of a space is 60 μm and a calculation result of a first calculating process.

The graph of FIG. 10 shows the content that indicates the amplitude ratio $\Psi_E$ and the phase difference $\Delta_E$ which are measured from the organic EL element 50 where the thickness dimension D of the space 60 is 60 μm and the amplitude ratio $\Psi_M$ and the phase difference $\Delta_M$ which are calculated from the model. The measured amplitude ratio $\Psi_E$ and phase difference $\Delta_E$ are represented by dots, and the amplitude ratio $\Psi_M$ and the phase difference $\Delta_M$ that are calculated from the model are represented by curves (the phase difference is represented by a solid line, and the amplitude ratio is represented by a dashed line). In the organic EL element 50 related to the graph of FIG. 10, the thickness dimension D is 60 μm. Thus, the sample analyzing apparatus 1 calculates the amplitude ratio $\Psi_M$ and the phase difference $\Delta_M$ through the first calculation process, and the amplitude ratio $\Psi_M$ and the phase difference $\Delta_M$ are faithfully calculated in accordance with the model. For this reason, in the range (for example, the range in which a photon energy is 2.2 eV or less) where the dots of measurement points have the amplitudes correspondingly to the resolution of the spectrometer, the curves indicating the amplitude ratio $\Psi_M$ and the phase difference $\Delta_M$ also have the amplitudes in the upper and lower directions and have the contents corresponding to the occurrence of the interference pattern. Also, the first calculation process, since calculating even the content having the foregoing amplitudes in detail, can calculate the thickness of the space, and the process time becomes long as compared with the second calculation process.

Figure 9:
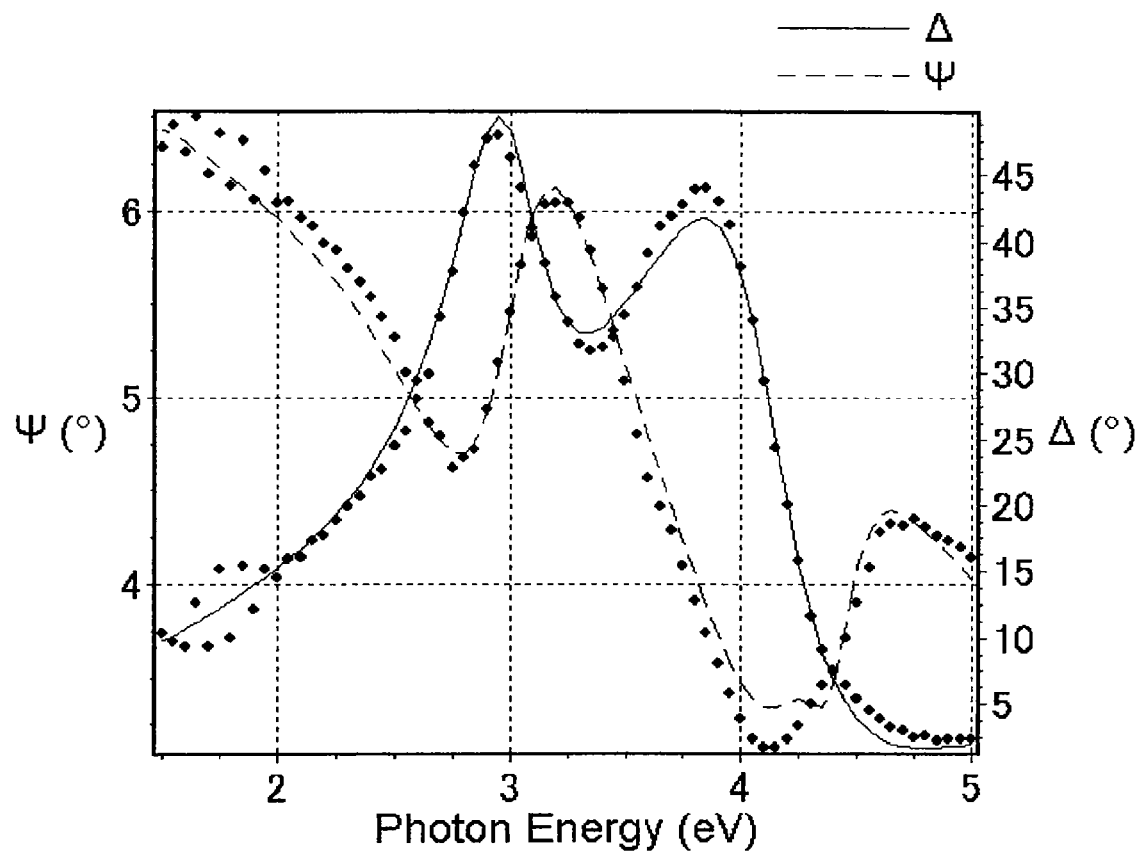
FIG. 9 is a graph showing a measurement result when a light is irradiated from a glass substrate to a sample (organic EL element) in which a thickness of a space is 60 μm and a calculation result of a second calculating process.

On the other hand, the graph of FIG. 9 shows the result after the second calculation process is performed on the model of the organic EL element 50 related to the graph of FIG. 10 for the sake of a comparison. Since the amplitude ratio $\Psi_M$ and the phase difference $\Delta_M$ are calculated through the second calculation process, the amplitude ratio $\Psi_M$ and the phase difference $\Delta_M$ have the smoothed shapes so as to be passed through the middle of the dots that are the measurement points.

Figure 11:
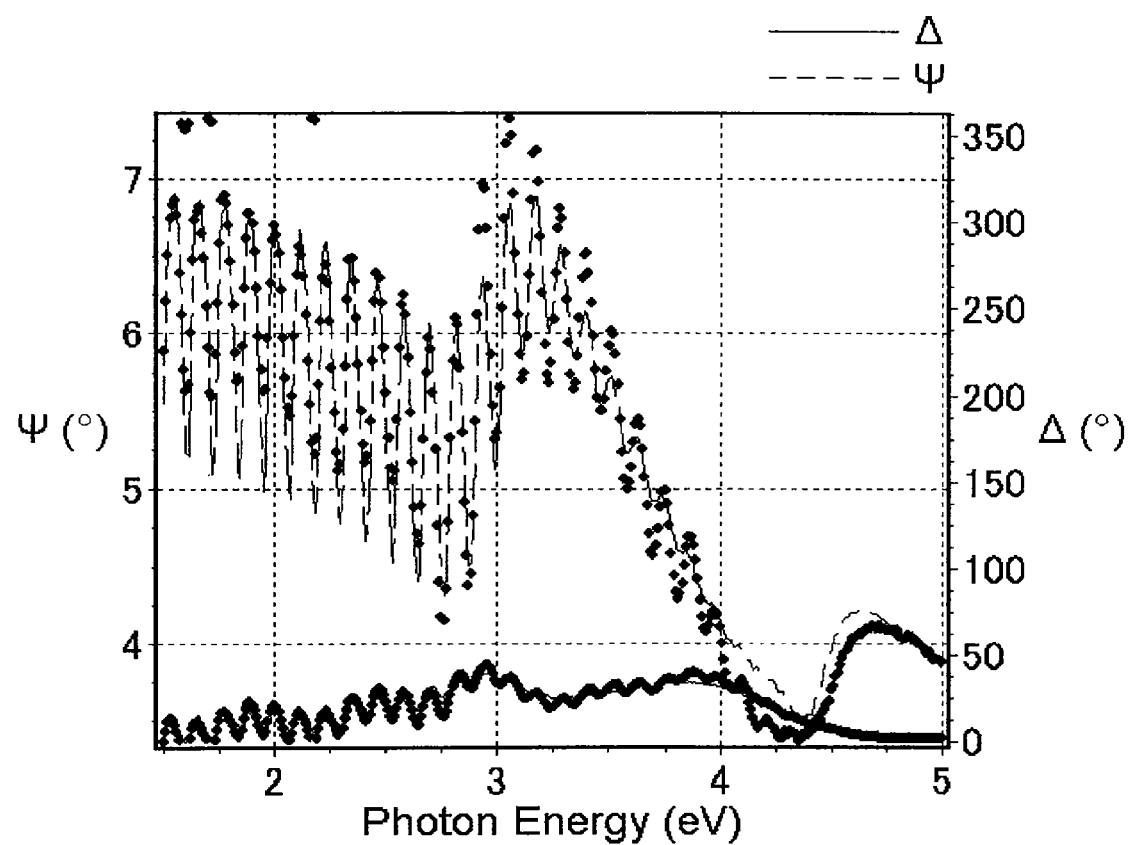
FIG. 11 is a graph showing a measurement result when a light is irradiated from a glass substrate to a sample (organic EL element) in which a thickness of a space is 10 μm and a calculation result of a first calculating process.

Note that the graph of FIG. 11 shows the result after the first calculation process is performed on the model of the organic EL element 50 in which the thickness dimension D of the space 60 is 10 μm. Similarly to the dots of the measurement points having the amplitudes in the upper and lower directions, the curves indicating the amplitude ratio $\Psi_M$ and the phase difference $\Delta_M$ which are calculated from the model have the great amplitudes in the upper and lower directions (in particular, the amplitude of the amplitude ratio indicated by the dashed line is great).

Figure 8A:
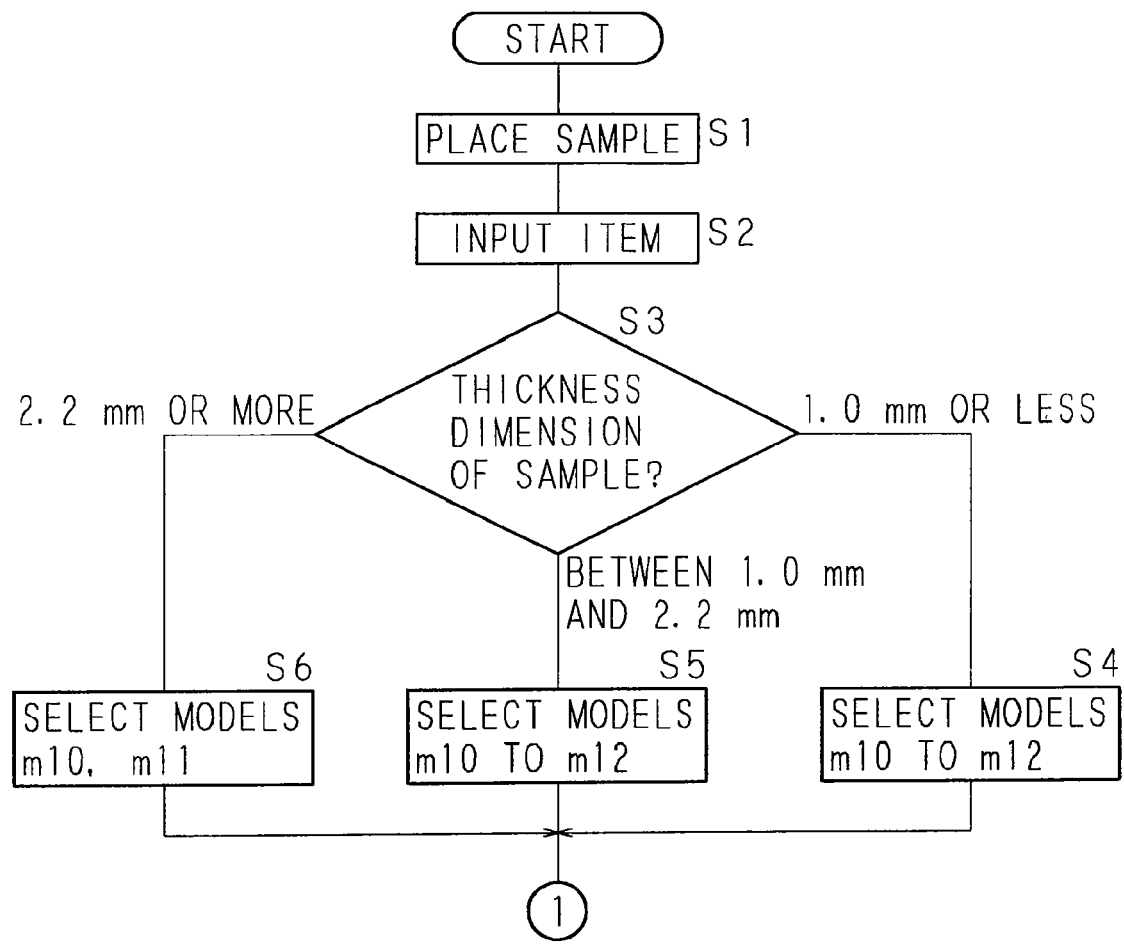
FIGS. 8A and B are flowcharts showing a series of process procedures of a sample analyzing method.
Figure 8B:
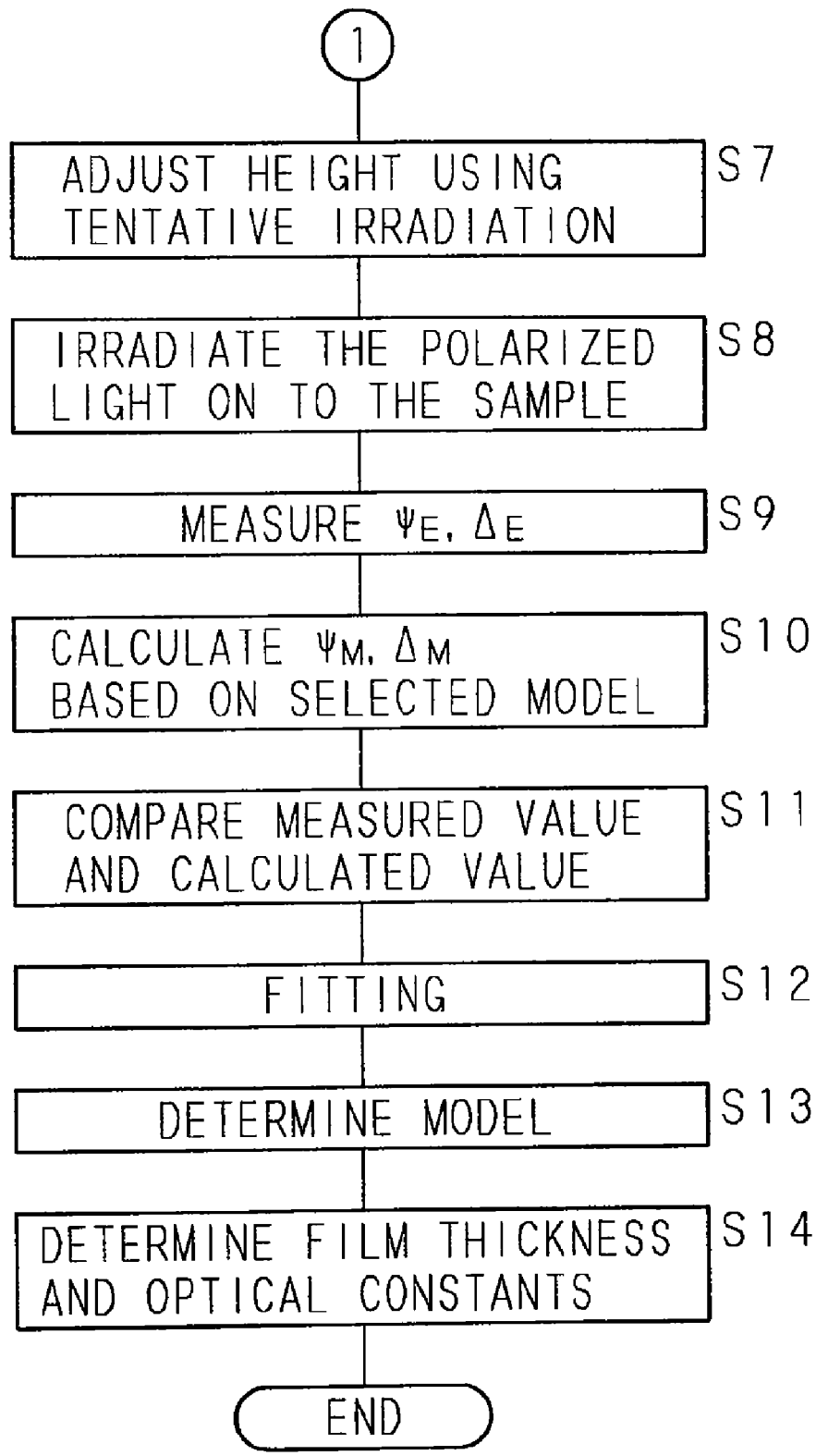

Again in the flowcharts of FIGS. 8A and B, the explanation of the process procedure of the sample analyzing method is continued. The measured value (measured result) by the ellipsometer and the calculation value obtained from the model are compared (S11), and the computer 10 carries out the fittings of the thickness of each layer in the model and the like and the parameter of the dispersion formula, so as to make the difference between the compared respective values smaller (S12).

Note that for the plurality of models to be used for the analysis, in the foregoing stages (S10 to S12), all of the models are fitted to calculate the mean square error obtained from the least squares method. The model related to the value of the lowest mean square error, or the model having the lowest value of the mean square error within the range between the maximum value and the minimal value of the film thickness preset in the computer 10 is selected.

In the thus-selected model, if with the final fitting, the difference calculated from the least squares method reaches to the necessary value (becomes sufficiently small), it is checked that the film thicknesses of the respective film layers 52 to 55 related to the model used at that time and the like do not have the physically impossible values, and the model at that time is then determined to be the best model (S13). Finally, the sample analyzing apparatus 1 refers to the film thicknesses of the respective film layers 52 to 55 related to the best model, the parameters of the dispersion formula, the voids and the like. Thus, as the characteristics of the respective film layers 52 to 55 of the organic film 56 in the organic EL element 50, the film thicknesses and the optical constants (the refractive index n and the extinction coefficient k) and the like are determined in the respective film layers (S14). Note that if, although the difference calculated from the least squares method reaches to the necessary value, the film thicknesses of the respective film layers 52 to 55 related to the model at that time and the like have the physically impossible values, the values related to the configurations of all of the models and the like are changed to again carry out the fitting (the processes after S10).

In this way, in the present invention, even in the case that the film serving as the analysis target of the organic EL element 50 is covered, the light is irradiated towards the glass substrate 51, and the light is applied to the organic film 56. Thus, the respective film layers of the organic film 56 can be measured by the ellipsometer. Also, in the sample analyzing apparatus 1, in accordance with the foregoing condition, the first calculation process and the second calculation process are differently used for different purposes. Thus, the calculation process related to the model is efficiently advanced, and the structure kind of the model is throttled in accordance with the thickness of the sample serving as the analysis target. Hence, the burden on the analysis process can be reduced.

Note that the sample analyzing apparatus 1 and sample analyzing method according to the present invention are not limited to the above-mentioned embodiment, and they can be applied to various variations. For example, when the cover glass 57 of the organic EL element 50 is made of nontransparent material (metal, synthetic resin and the like), the reflection manner such as the reflected beam K3 shown in FIG. 3 is not induced. Thus, the computer 10 selects one or both of the model m10 of FIG. 6A and the model m11 of FIG. 6B which correspond to the reflected beam K1 or the reflected beam K2, respectively, as the structure of the model to be used for the analysis in accordance with the comparison of the thickness dimension of the sample.

Also, in the foregoing explanation, the setting menu 20 shown in FIG. 7 is explained such that 100 μm is set for the input column 21b of the standard value. Of course, the other values can be set on the basis of the sample and the measurement situation and the like. Under the condition that the value is set, when a new value is inputted, the sample analyzing apparatus 1 carries out a step of changing the standard value. Hereafter, this changed new value is used to carry out the comparison with the thickness dimension D of the space 60. Since the standard value can be designed to be changed in this way, the process can be smoothly executed for the case of measuring the sample where the influence of the measurement situation and the condition of the occurrence of the interference pattern are slightly different. Note that an idea where the proper value (for example, 100 μm for the standard value) as a default value is set for the predetermined item including the standard value is desirable from the viewpoint of the drop in the input burden on the user.

Moreover, instead of the configuration that in accordance with the comparison with the thickness dimension D of the space 60, which of the first calculation process and the second calculation process is executed is judged by the sample analyzing apparatus 1, an idea that the user can optionally select may be employed. In this case, a selection button to indicate the first calculation process or second calculation process under which the process is executed is installed in the setting menu prior to the measurement or the like, and the sample analyzing apparatus 1 carries out the process under any of the first calculation process and the second calculation process, in accordance with the indication received from the user.

Figure 12:
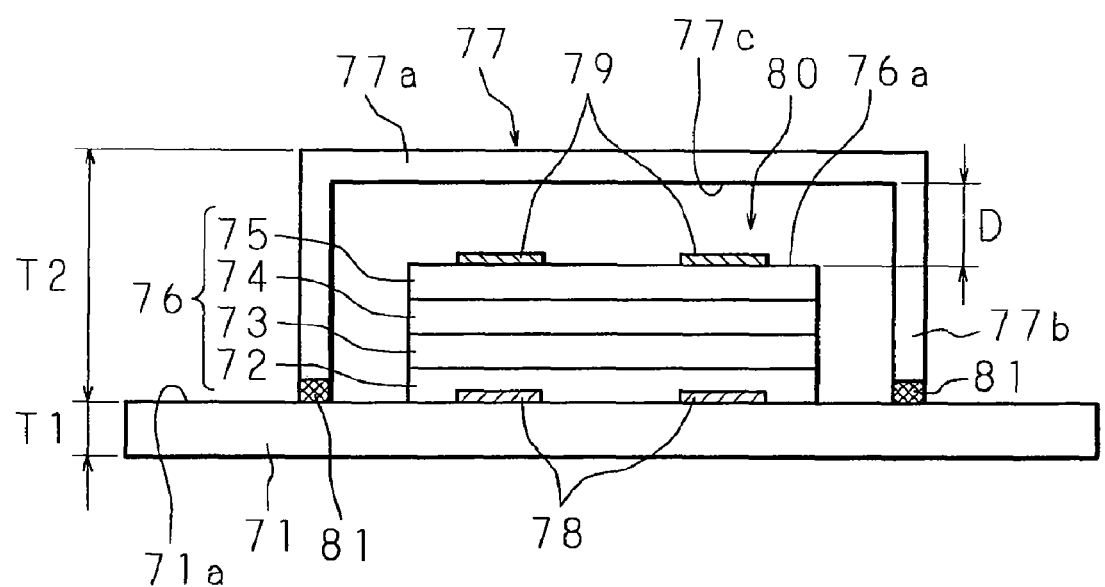
FIG. 12 is a schematic view showing a structure of an organic EL element of a research development type.

Moreover, the sample analyzing apparatus 1 in this embodiment can similarly perform the analysis on even an organic EL element 70 of a research development type shown in FIG. 12, other than the organic EL element 50 of the production type shown in FIGS. 4A and B. The difference between the organic EL element 70 of the research development type and the organic EL element 50 of the production type lies in a structure that in the organic EL element 70, a sealing cap 77 (height T2) having a shape of a cap is attached through an adhesive 81 to a glass substrate 71 having a transparent performance of a thickness T1.

The sealing cap 77 contains: an organic film 76 (a plurality of layers 72 to 75) formed on one surface 51a of the glass substrate 71; and a cover portion 77a and a side wall portion 77b so as to cover electrodes 58, 59, and has the entirely concave shape. Also, in the sealing cap 77, a space 80 of a thickness dimension D is formed at an gap (gap) from the uppermost surface 76a of the organic film 76 to an inner surface 57c of the cover portion 77a. When the organic EL element 70 of FIG. 12 is analyzed by the sample analyzing apparatus 1, if the value to which a thickness T1 of the glass substrate 71 and the height T2 of the sealing cap 77 are added is inputted as the thickness dimension of the sample, the analysis can be executed by treating the other points similarly to the organic EL element 50 shown in FIGS. 4A and B.

Figure 13:
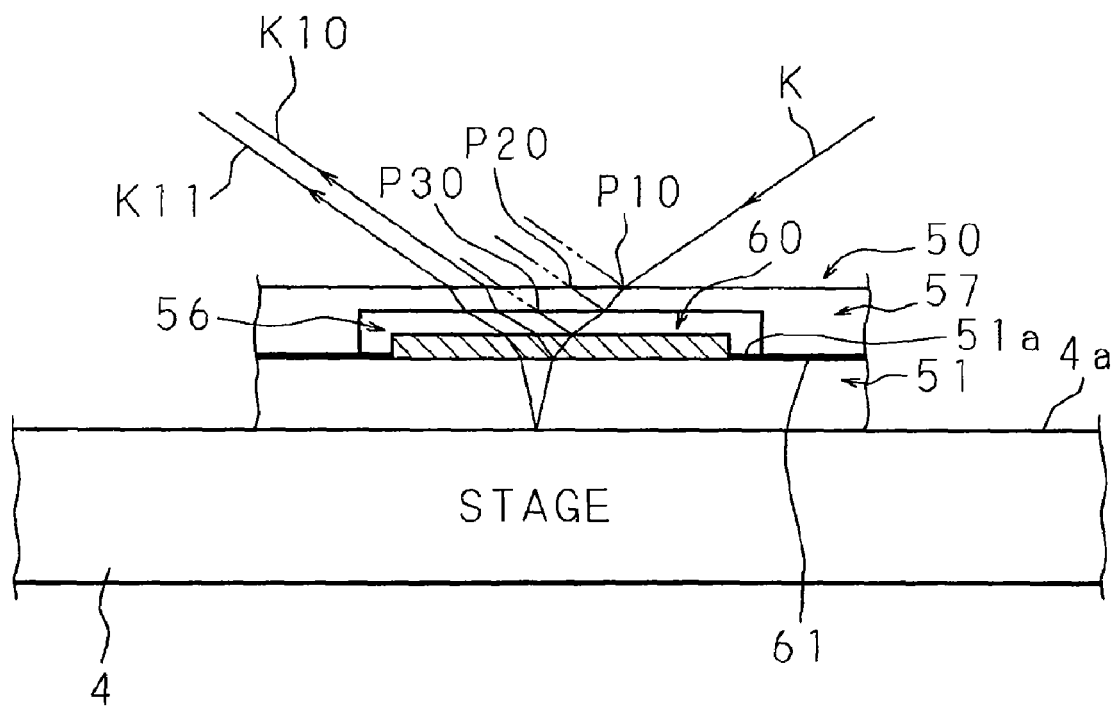
FIG. 13 is a schematic view showing an arrangement when an irradiation is applied to a cover glass of an organic EL element.

Furthermore, if the cover glass 57 of the organic EL element 50 has the transparent property, other than the manner that the organic EL element 50 is placed on the stage 4 in the situation shown in FIG. 5, as shown in FIG. 13, in such a way that the glass substrate 51 is brought into contact with the stage surface 4a of the stage 4, the organic EL element 50 may be placed under a situation that the glass substrate 51 is located on the lower side. In this case, in the sample analyzing apparatus 1, the beam K of the polarization state is irradiated towards the cover glass 57, and the beam K passed through the cover glass 57 and the space 60 arrives at the organic film 56 composed of the plurality of film layers 52 to 55 (refer to FIG. 4B). Moreover, there is a case that after the beam K is passed through the organic film 56, it is reflected on the boundary between the organic film 56 and the glass substrate 51 as shown in FIG. 13 (the case of a reflected beam K10) and a case that it is passed through even the glass substrate 51 and then reflected on the boundary between the glass substrate 51 and the stage 4 (the case of a reflected beam K11). Note that any of the reflected lights K10, K11 is outputted from the cover glass 57 and obtained by the light obtainer 5, and the polarization state is measured.

Note that even in FIG. 13, although the reflection (P10) from the cover glass surface, the reflection (P20) from the cover glass inner surface, the reflection (P30) from the organic film surface and the multiple reflection are actually included, those reflections (P10, P20 and P30) are not directly related to the selection of the model to be used in the analysis. Thus, their treatments are omitted.

Figure 14A:
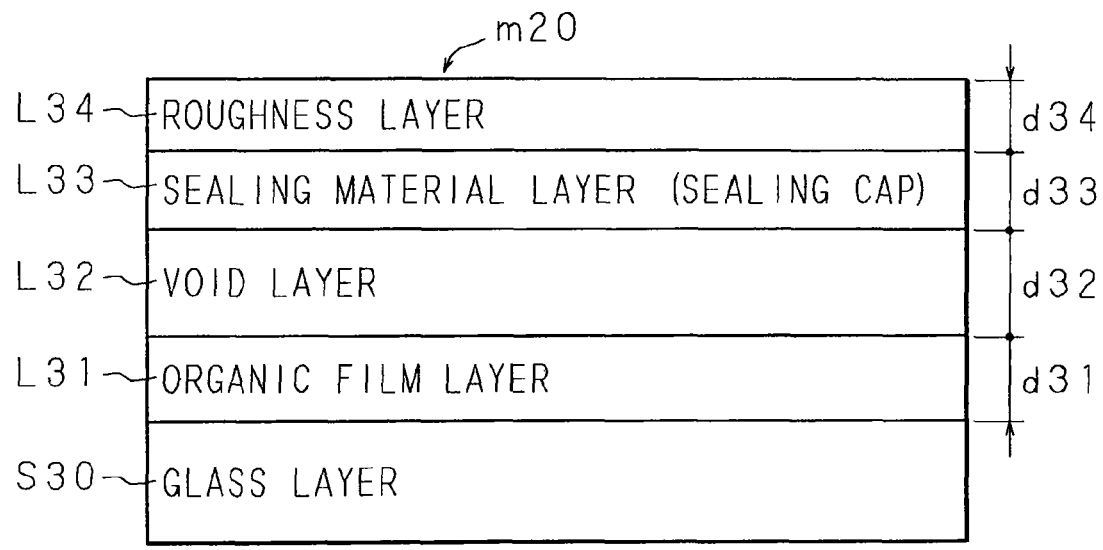
FIG. 14A is a schematic view showing a model of a structure corresponding to a reflected beam K10 of FIG. 13.

Also, when the sample is analyzed in the placement manner of the organic EL element 50 shown in FIG. 13, the model to be used for the analysis is required to use the structure corresponding to the reflected lights K10, K11. FIG. 14A shows a model m20 of the structure corresponding to the reflected beam K10. The model m20 has the structure where the lowest glass substrate 51 is defined as a substrate (S30), and an organic film layer L31 (corresponding to the organic film 56), a void layer L32 (corresponding to the space 60), a sealing material layer L33 (corresponding to the portion without any surface roughness of the cover glass 57) and a roughness layer L34 (the portion corresponding to the surface roughness of the cover glass 57) are stacked thereon. Note that thicknesses d31 to d34 of the respective layers of a model m30 are set in accordance with the value inputted by the user in the preparation stage.

Figure 14B:
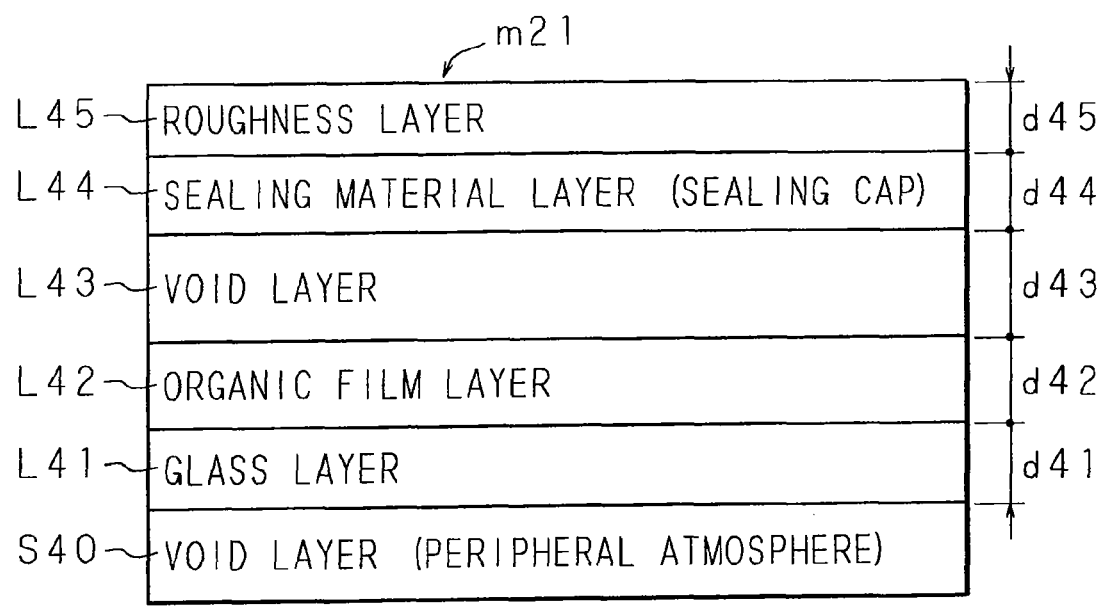
FIG. 14B is a schematic view showing a model of a structure corresponding to a reflected beam K11 of FIG. 13.

On the other hand, FIG. 14B shows a model m21 of the structure corresponding to the reflected beam K11. The model m21 has the structure where the medium (corresponding to the void layer of the space existing between the glass substrate 51 and the stage 4 in FIG. 13) constituting the peripheral atmosphere below the glass substrate 51 is regarded as the substrate, and a glass layer L41 (corresponding to the glass substrate 51), an organic film layer L42 (corresponding to the organic film 56), a void layer L43 (corresponding to the space 60), a sealing material layer L44 (corresponding to the portion without any surface roughness of the cover glass 57) and a roughness layer L45 (the portion corresponding to the surface roughness of the cover glass 57) are stacked on its void layer S40 (substrate). Note that thicknesses d41 to d45 of the respective layers of the model m21 are set in accordance with the value inputted by the user in the preparation stage.

In the placement manner shown in FIG. 13, there is a possibility that only one (only K10 in view of a theory) or both of the reflected lights K10, K11 are measured depending on the thickness dimension of the organic EL element 50. Thus, in the sample measurement apparatus 1, as the process stages (S3 to S6) of the flowcharts in FIGS. 8A and B, one (the model m20 in view of the theory) or both of the models m20, m21 are selected as the structure of the model to be used for the analysis, depending on the thickness dimension of the sample. Note that after the model selection, the process similar to the flowcharts of FIGS. 8A and B are carried out to carry out the analysis.

Figure 15:
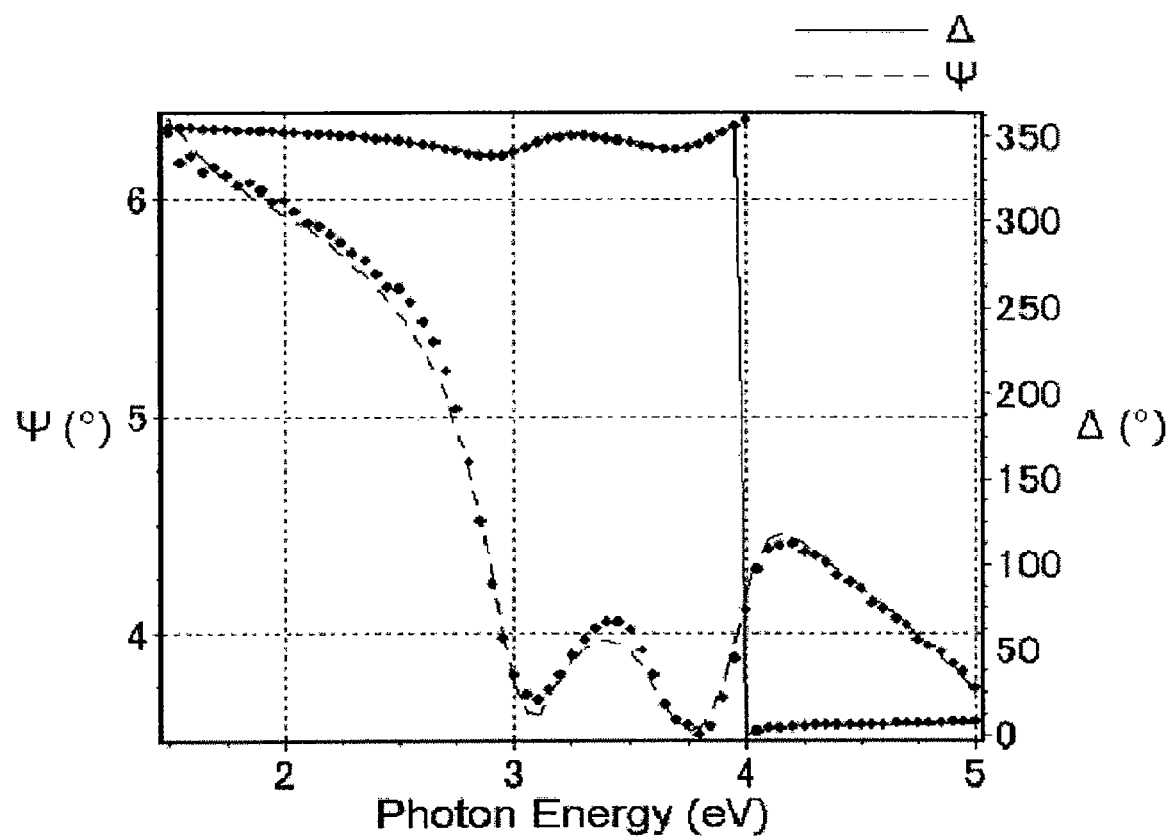
FIG. 15 is a graph showing a measurement result when a light is irradiated from a glass cover to a sample (organic EL element) in which a thickness of a space is 60 μm and a calculation result of a second calculating process.

Also, even in the placement manner of the organic EL element 50 shown in FIG. 13, when the values (the amplitude ratio and the phase difference) related to the model is calculated, the first calculation process or second calculation process is carried out on the basis of the comparison between the thickness dimension D of the space 60 and the standard value or the indication of the user. A graph shown in FIG. 15 shows: the dots of the amplitude ratio $\Psi_E$ and the phase difference $\Delta_E$ when the organic EL element 50 having the thickness dimension D of the space 60 are measured under the placement manner shown in FIG. 13; and the curves of the amplitude ratio $\Psi_M$ and the phase difference $\Delta_M$ which are calculated in the second calculation process from the model of the structure based on this placement manner. The calculated curves have the shapes substantially along the measurement points (dots). Note that even under the placement manner shown in FIG. 13, the organic EL element 70 of the research development type in FIG. 12 can be measured and analyzed. In that case, a model in which the cover glass 57 is considered to be the sealing cap 77 is prepared (refer to FIGS. 14A and B).

Also, in the sample analyzing apparatus 1 and the sample analyzing method according to the present invention, with regard to the organic EL element 50, any type of a so-called big polymer organic EL element and small molecular organic EL element can be targeted for the analysis. Also, as for a sample other than the organic EL elements, the sample where the film is deposited on the substrate, and it is configured to be covered with the cover material (cover member) at an gap from the film, and at least one of the substrate and the cover material has the transparent property can be analyzed under the situation similar to the organic EL element 50 as mentioned above.

Second Embodiment

Figure 16:
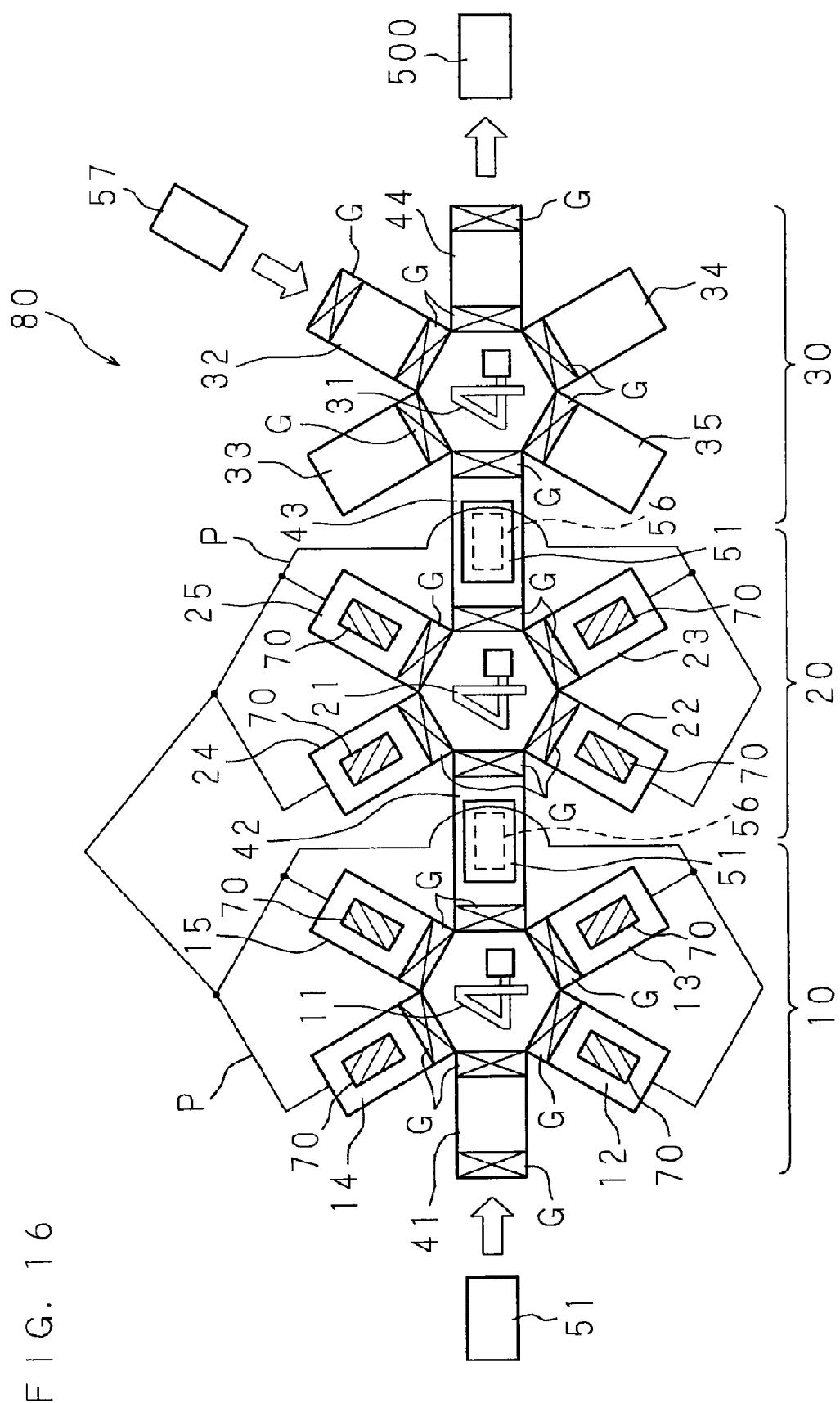
FIG. 16 is a schematic plan view showing a schema of a manufacturing equipment according to the present invention.

The embodiment of the present invention will be described below with reference to the drawings. FIG. 16 is a schematic plan view showing the schema of a manufacturing equipment 80 according to the present invention. The manufacturing equipment 80 is provided with: two series of a first film forming cluster (apparatus) 10 and a second film forming cluster (apparatus) 20 for forming film deposition (formation) products 56 on the glass substrates 51; and a sealing cluster (apparatus) 30 where a sealing substrate 57 is stuck to the glass substrate 51 on which the film deposition product 56 is formed and an organic EL element panel 500 is discharged. The glass substrate 51 is fed to the first film forming apparatus 10 and the second film forming apparatus 20 and fed to the sealing cluster 30 after the film deposition product 56 is formed. In the sealing cluster 30, after the sealing substrate 57 is stuck to the glass substrate 51 on which the film deposition product 56 is formed, the organic EL element panel 500 as the completion product is discharged to outside.

The first film forming apparatus 10 is provided with a feeding robot (vacuum feeding robot) 11 serving as a feeding device (feeding apparatus), a substrate feeding chamber (room) 41, film forming chambers 12, 13, 14 and 15, an optical film thickness measurement apparatus 70, a vacuum gate G, a receiving/passing chamber 42 and a data transmission device P. The feeding robot 11 is installed at the substantial center of the first film forming apparatus 10. So as to surround it, the substrate feeding chamber 41, the film forming chambers 12, 13, 14 and 15 and the receiving/passing chamber 42 are connected though the vacuum gate G having a sealing property. The glass substrate 51 (ITO substrate) on which a pre-process step and a washing operation are already performed is fed to the substrate feeding chamber 41 where the vacuum gates G, G are installed at an inlet and an outlet. The glass substrate 51 fed to the substrate feeding chamber 41 is fed to the film forming chamber 12 by the feeding robot 11.

The film forming chambers 12, 13, 14 and 15 and film forming chambers 22, 23, 24 and 25 of the second film forming apparatus 20 are intended to gradually generate the film deposition product 56 that includes the hole transport layer, the light emission layer, the hole blocking layer, the electron feeding layer and the cathode, respectively. The optical film thickness measurement apparatuses 70, 70, 70—to measure the film thicknesses of the respective layers of the film deposition product 56 are installed on the upper side of the respective film forming chambers 12, 13, 14, 15, 22, 23, 24 and 25. Note that the hereafter, the film depositions executed in the film forming chambers 12 to 15 and 22 to 25 are explained as the evaporation through a CVD (Chemical Vapor Deposition) method. However, depending on the film deposition target, the film deposition through a PVD (Physical Vapor Deposition) method of a sputtering method or the like may be properly used. Hereafter, this is explained under assumption that the film forming chambers 12 to 15 and 22 to 25 are the evaporating chambers 12 to 15 and 22 to 25 and the film deposition product 56 is an evaporation product 56. As the optical film thickness measurement apparatus 70, for example, the polarimeter, the ellipsometer and the like can be used. Hereafter, this is explained under assumption that the optical film thickness measurement apparatus 70 is an ellipsometer 70. Also, hereafter, a case where the ellipsometer 70 using a phase modulation method is applied is explained. However, it is naturally allowable to apply the ellipsometer 70 using a rotation analyzer method.

When the glass substrate 51 is fed to the evaporating chamber 12, the evaporation is started, and the film thickness measurement is simultaneously started by the ellipsometer 70. The evaporation product 56 is evaporated on the glass substrate 51, and if it is judged to reach the preset film thickness by the ellipsometer 70, the evaporating chamber 12 stops the evaporation. The glass substrate 51 on which the evaporation product 56 of the first layer is evaporated is fed to the evaporating chamber 13 of the next stage by the feeding robot 11 serving as the feeding device. In the evaporating chamber 13, the evaporation product 56 of the second layer is evaporated, and its film thickness is measured by the ellipsometer 70 installed in the evaporating chamber 13. When the evaporation product 56 of the second layer arrives at a preset film thickness in the evaporating chamber 13, the evaporation is stopped, and it is fed to the evaporating chamber 14 of the next stage. The respective evaporating chambers 12 to 15 and 22 to 25 are connected through the data transmission device P that includes a transmission line and a transmission reception apparatus. The information with regard to the evaporation situations in the respective evaporating chambers 12 to 15 and 22 to 25 is transmitted and received through the data transmission device P.

In this way, in the first film forming apparatus 10, the evaporations of the first to fourth layers are carried out together with the film thickness measurement in real time through the respective ellipsometers 70. After the completion of the evaporation of the fourth layer, the glass substrate 51 on which the evaporation product 56 is evaporated is fed to the receiving/passing chamber 42, in which the vacuum gates G are installed at the inlet and the outlet, by the feeding robot 11. The second film forming apparatus 20 linked to the receiving/passing chamber 42 is also provided with a vacuum gate G, the evaporating chambers 22 to 25, the data transmission device P, the ellipsometers 70, a feeding robot 21 and a receiving/passing chamber 43, similarly to the first film forming apparatus 10.

The glass substrate 51 is fed through the receiving/passing chamber 42 to the evaporating chamber 22 of the second film forming apparatus 20, and the evaporation of the fifth layer is carried out. Similarly to the first film forming apparatus 10, the ellipsometers 70, 70, 70—are also installed in the evaporating chambers 22 to 25, and the film thicknesses of the respective layers on which the evaporations are performed are measured. Then, it arrives at a preset film thickness, it is fed to the evaporating chamber 23 of the next stage by the feeding robot 21 serving as the feeding device. The glass substrate 51 on which the evaporation product 56 is evaporated in the evaporating chambers 22 to 25 is fed to the receiving/passing chamber 43 by the feeding robot 21. Note that this embodiment has the two-stage configuration composed of the first film forming apparatus 10 and the second film forming apparatus 20. However, the film deposition may be carried out by installing the film forming apparatus composed of one stage or three stages or more. Moreover, the first film forming apparatus 10 and the second film forming apparatus 20 contain the four evaporating chambers 12 to 15 and 22 to 25, respectively. However, its number may be properly increased or decreased depending on the number of the evaporation layers.

The sealing cluster 30 linked to the receiving/passing chamber 43 is provided with a feeding robot 31, a vacuum gate a sealing chamber 34, a discharging chamber 44 and a sealing substrate feeding chamber 32. The glass substrate 51 after the completion of the evaporations onto all of the layers is fed to the sealing chamber 34 by the feeding robot 31. Also, even the sealing substrate 57 fed to the sealing substrate feeding chamber 32 is similarly fed to the sealing chamber 34. The glass substrate 51 on which the evaporation product 56 is evaporated and the sealing substrate 57 are stuck to each other through adhesive in the sealing chamber 34. The stuck organic EL element panel 500 is fed through the discharging chamber 44 to the outside. Note that an inspecting chamber 33 for inspecting the optical characteristic and a spare film forming chamber 35 for spare may be installed in the sealing cluster 30.

Figure 17:
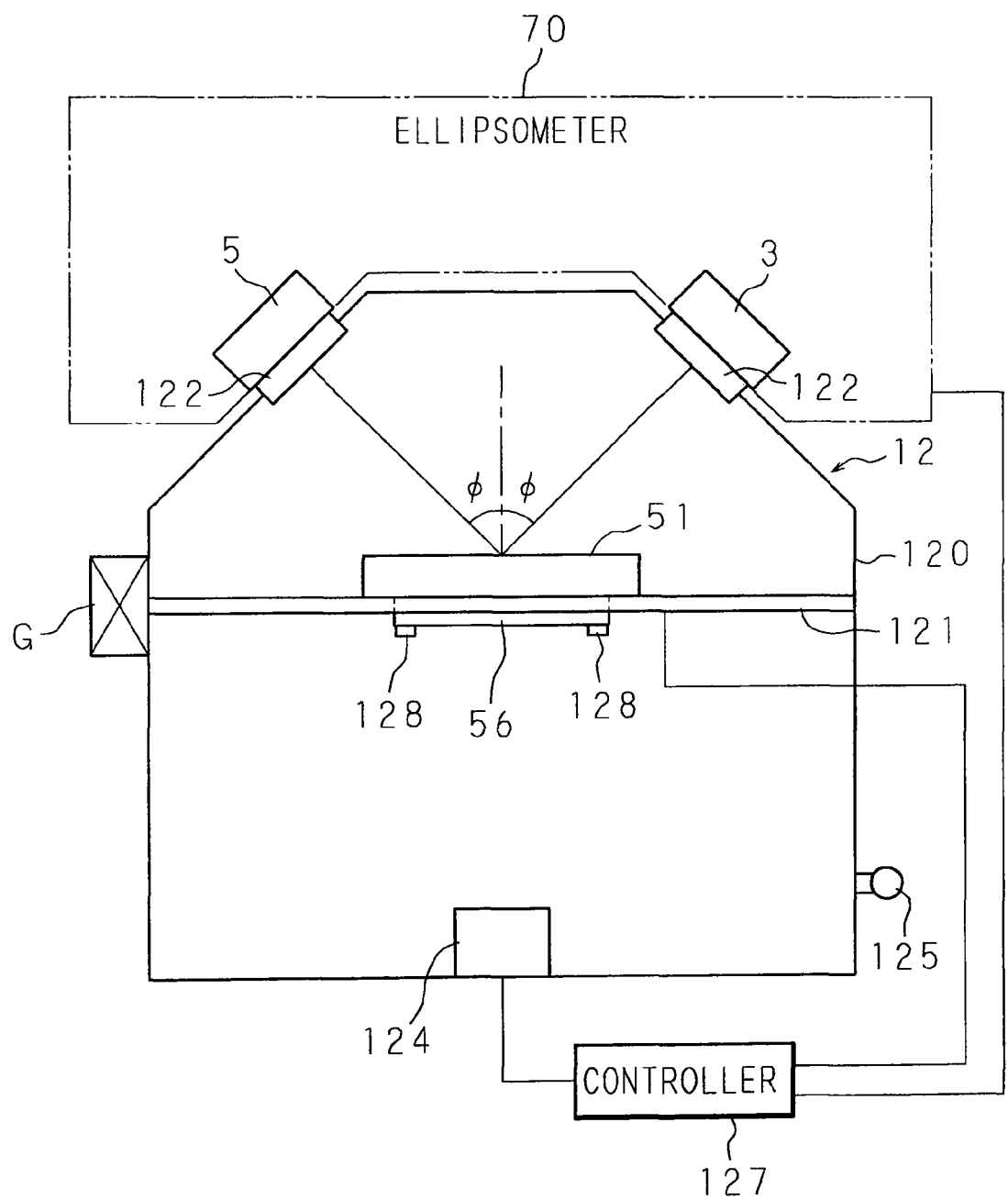
FIG. 17 is a diagrammatic sectional view showing a section of an evaporating chamber.
Figure 18:
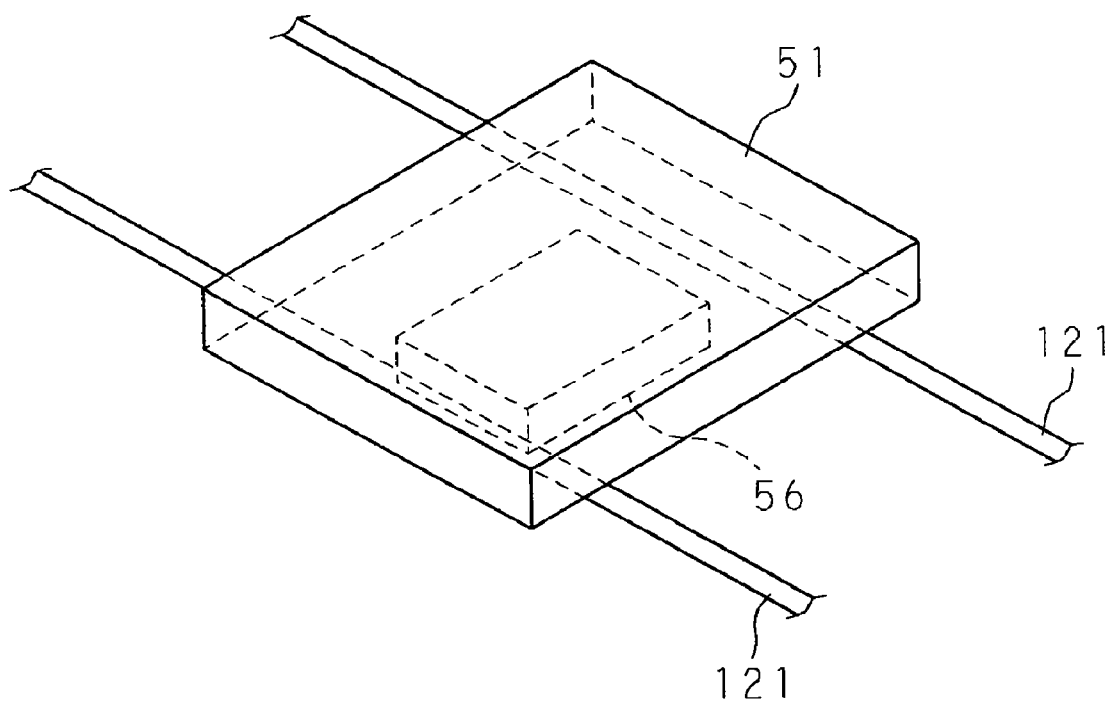
FIG. 18 is a diagrammatic perspective view showing a schema of an inside of the evaporating chamber.

FIG. 17 is a diagrammatic sectional view showing a section of the evaporating chamber 12, and FIG. 18 is a diagrammatic perspective view showing the schema of the inside of the evaporating chamber 12. The evaporating chamber 12 is provided with racks 121 where the glass substrate 51 on which the evaporation product 56 is evaporated is placed, an evaporation unit (film deposition unit) 124, a controller (control apparatus) 127 and a decompression apparatus 125. The evaporating chamber 12 contains a body 120 that has a rectangular bottom and a trapezoidal top in its section, and the two racks 121, 121 are mounted at the substantial center of the body 120. The glass substrate 51 is fed into the evaporating chamber 12 by the feeding robot 11 shown in FIG. 16 and placed on the racks 121, 121. That is, as for the glass substrate 51 fed to the evaporating chamber 12 from the vacuum gate G, both ends thereof are supported by the racks 121, 121 as shown in FIG. 18, and it is fed to the position where the evaporation and the measurement of the film thickness are possible.

The glass substrate 51 is placed on the racks 121, 121 so that the deposition direction of the evaporation product 56 is downward, and so as to attain a desirable pattern, a mask 128 is formed inside the evaporating chamber 12. Note that the notation of the mask 128 is omitted in FIG. 18. An evaporation unit 124 is installed on the bottom surface of the body 120 in the evaporation direction of the evaporation product 56. The evaporation unit 124 is constituted by: a crucible or boat in which the evaporation material is filled; and a heat source for heating the crucible or boat. In accordance with the control of the controller 127, this discharges the evaporation material and evaporates the evaporation product 56 on the glass substrate 51. Note that the controller 127 is connected so as to be able to transmit and receive an information to and from the ellipsometer 70.

In the deposition direction of the evaporation product 56 and on the side wall of the body 120 in the evaporating chamber 12, the decompression apparatus 125 is placed so as to penetrate through the side wall. The decompression apparatus 125 decreases the pressure inside the evaporating chamber 12.

The top of the body 120 has the shape of a trapezoid having two oblique sides, and transmission windows 122, 122 such as glass and the like are fixedly installed on the two oblique sides in a situation that each sealed property is kept. On the side opposite to the deposition direction of the evaporation product 56 and on the upper side of the body 120, the ellipsometer 70 that contains the light irradiator 3 and the light obtainer 5 is installed. The output surface of the light irradiator 3 and the outer surface side of the body 120 of the transmission window 122 are in contact with each other. Similarly, the light reception surface of the light obtainer 5 and the outer surface side of the body 120 of the transmission window 122 are in contact with each other. It is noted that the light irradiator 3 and the light obtainer 5 may be installed away from the transmission window 122. The incident light from the light irradiator 3 is inputted substantially vertically to the transmission window 122 installed on the oblique side and irradiated onto the rear of the glass substrate 51 on which the evaporation product 56 is evaporated. The reflected light from the glass substrate 51 is inputted substantially vertically to the transmission window 122 and arrives at the light obtainer 5. Note that in this embodiment, the evaporation unit 124 is installed on the lower side of the evaporating chamber 12, and the ellipsometer 70 is installed on the upper side of the evaporating chamber 12, respectively. However, when the deposition (lamination) direction of the evaporation product 56 is upward, the evaporation unit 124 may be installed in the deposition direction, namely, on the upper side of the evaporating chamber, and the ellipsometer 70 for carrying out the output/input through the transmission window 122 may be installed on the lower side of the evaporating chamber 12 opposite to the deposition direction.

Figure 19:
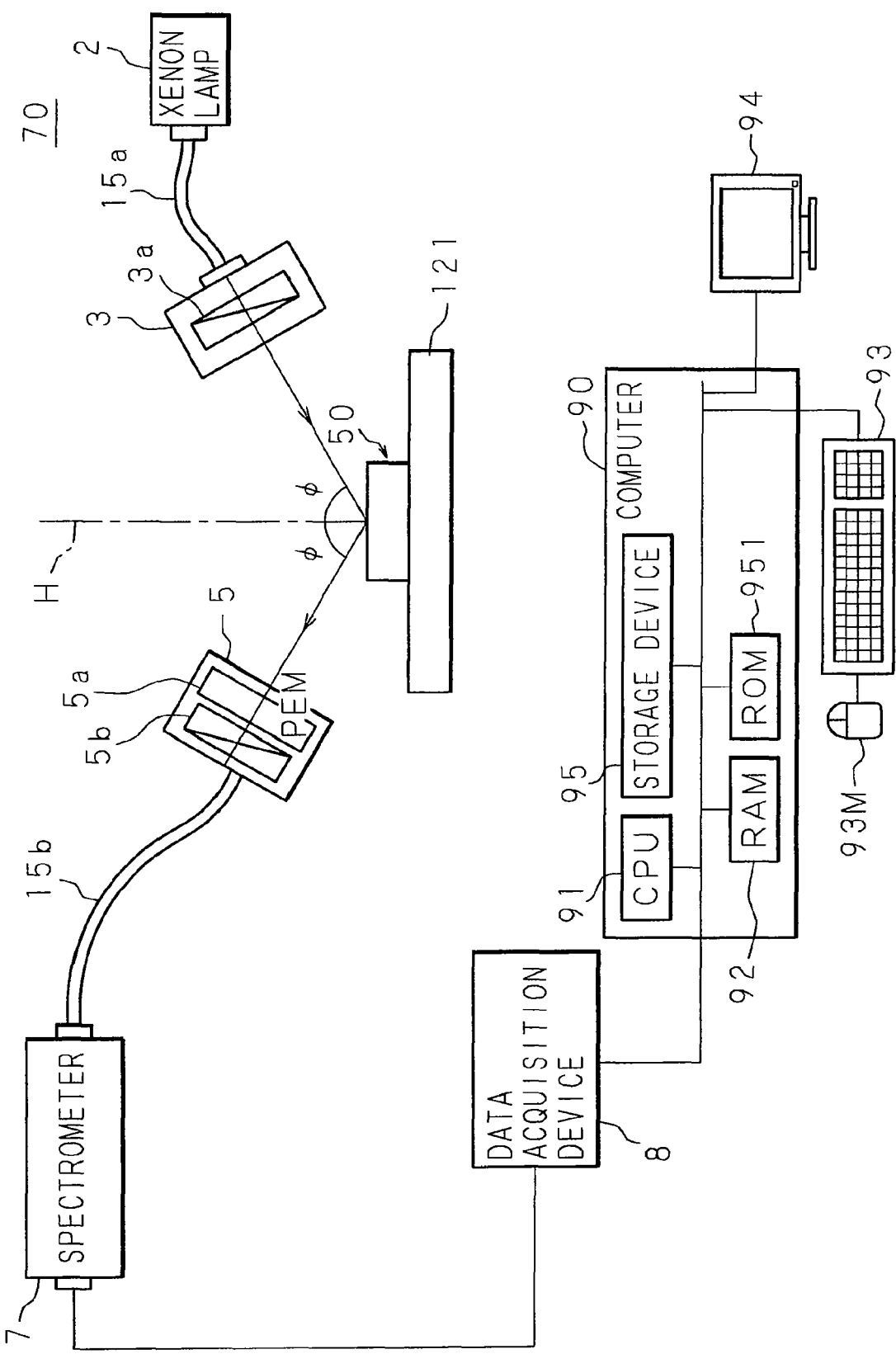
FIG. 19 is a block diagram showing a hardware configuration of an ellipsometer.

FIG. 19 is a block diagram showing the hardware configuration of the ellipsometer 70. The ellipsometer 70 shown in FIG. 19 is roughly classified into a portion of a measurement analysis group and a drive group portion. The ellipsometer 70 is configured such that as the portion of the measurement analysis group, the xenon lamp 2 and the light irradiator 3 are connected through the first optical fiber cable 15a, and the light of the polarization state is irradiated onto the glass substrate 51 which is placed on the rack 121 and on which the evaporation product 56 is evaporated (hereafter, they are referred to as a sample 50), and the light is inputted to the sample 50, and the light reflected on the sample 50 is acquired by the light obtainer 5. Note that the evaporating chamber 12, the transmission window 122 and the like are omitted in FIG. 19 in order to simplify the explanation.

The light obtainer 5 is connected through the second optical fiber cable 15b to the spectrometer 7. The spectrometer 7 carries out the measurement for each wavelength and transmits the measurement result as the analog signal to the data acquisition device 8. The data acquisition device 8 converts the analog signal into the necessary value and transmits to a computer 90, and the analysis is carried out by the computer 90.

The foregoing respective portions of the ellipsometer 70 will be detailed below in turn. At first, the xenon lamp 2 serves as the light source, and generates the white light including the plurality of wavelength components and then sends the generated white light through the first optical fiber cable 15a to the light irradiator 3.

The light irradiator 3 has the polarizer 3a therein. Then, the white light is polarized by the polarizer 3a, and the light of the polarization state is irradiated onto the sample 50.

The light obtainer 5 obtains the light reflected on the sample 50 and measures the polarization state of the obtained light. In the light obtainer 5, the PEM (Photo Elastic Modulator) 5a and the analyzer 5b are built therein, and the light reflected on the sample 50 is guided through the PEM 5a to the analyzer 5b. Note that the PEM 5a built in the light obtainer 5 obtains the ellipse polarization from the straight polarization because the acquired light is phase-modulated at the necessary frequency (for example, 50 kHz). Also, the analyzer 5b selectively obtains and measures the polarization from the various polarizations which are phase-modulated by the PEM 5a. In this embodiment, it can be attained by obtaining the ellipse polarization through a rotation analyzer (RAE, RPE). However, when PEM is used, in addition to cos Δ, sin Δ can be obtained, which enables the improvement of the measurement precision. That is, in this embodiment, since the light is irradiated from the glass substrate 51 side, the phase difference Δ of the film that is the analysis target is small in value and small in change, in many cases. Hence, in order to extract Δ that is this small value at a high precision, the use of PEM that enables the detection of sin Δ is preferable.

The reflection mirror, the diffraction grating, the photo multiplier (PMT: Photo Multiplier Tube), the control unit and the like, which are not shown, are built in the spectrometer 7. Then, the light sent through the second optical fiber cable 15b from the light obtainer 5 is reflected by the reflection mirror and guided to the refractive grating. The spectrometer 7 is configured such that a total of 32 photo multipliers (not shown) are arranged in the shape of a fan with the refractive grating (not shown) as a center. The refractive grating reflects the light guided through a switcher and a mirror, which are not illustrated, towards the respective photo multipliers, and the reflection direction is distributed for each wavelength of the light at the time of the reflection. Each photo multiplier performs the measurement on the particular wavelength reflected by the refractive grating. Since the spectrometer 7 has the total of 32 photo multipliers, the simultaneous measurement of 32 ch (channels) is attained. A signal related to the content measured by each photo multiplier is sent to the data acquisition device 8. Note that, when the optical film thickness measurement apparatus uses the polarimeter, the configuration of the combination of photo diode arrays (PDA) is possible.

The data acquisition device 8 calculates the amplitude ratio and the phase difference Δ with regard to the polarization state (the p-polarization and the s-polarization) of the reflected light in accordance with the signal from the spectrometer 7 and sends the calculated result to the computer 90. Note that as for the amplitude ratio Ψ and the phase difference Δ, the relation of the following equation (7) is established for the amplitude reflection coefficient Rp of the p-polarization and the amplitude reflection coefficient Rs of the s-polarization.

$$Rp/Rs = \tan \Psi \cdot \exp(i \cdot \Delta) \quad (7)$$

However, i is the imaginary unit (hereafter, similarly). Also, Rp/Rs is referred to as the polarization change amount p.

Also, the computer 90 of the ellipsometer 70 analyzes the sample 50 in accordance with the amplitude ratio Ψ and the phase difference Δ of the polarization state, which are obtained by the data acquisition device 8, and the model corresponding to the sample 50. The computer 90 is provided with a display 94, a keyboard 93 and a mouse 93M and the like. A CPU (Central Processing Unit) 91, a storage unit 95, a RAM (Random Access Memory) 92 and a ROM (Read Only Memory) 951 are connected through an inner bus. The CPU 91 carries out the various processes in accordance with the various computer programs stored in the storage unit 95. The RAM 92 transiently stores the various data and the like with regard to the processes, and the ROM 951 stores the content related to the functions of the computer 90 and the like.

The storage unit 95 stores in advance the various programs such as the computer program for the sample analysis and also stores the data of the various menu images to be displayed on the display 94, the known data related to the sample 50, the models of the structures different from each other, the plurality of dispersion formulas to used to prepare the models, the prepared models, the reference data based on the various samples, and the standard value to be used in the comparison process related to the interference pattern, and the like.

With regard to the analysis of the sample 50, the computer 90 analyzes the optical constants, such as the refractive index, the extinction coefficient and the like, as the optical characteristics of the respective layers deposited on the evaporation product 56 and also analyzes the film thicknesses of the respective layers and the like. Note that an example of using the refractive index and the extinction coefficient as the optical constants will be described below.

Specifically, the computer 90 uses a modeling program that is stored in advance in the storage unit 95, if a complex refractive index of a peripheral atmosphere of the sample 50 is already known from the measured amplitude ratio Ψ and phase difference Δ. Then, the model corresponding to the material structure and the items of the sample 50 set by the user is prepared and stored in the storage unit 95, and the model stored at the analysis stage is used to calculate the film thicknesses and the complex refractive indexes of the respective film layers of the evaporation product 56. As for the complex refractive index N, when the layer to be analyzed is assumed to have the refractive index n and the extinction coefficient k, the relation of the equation (8) represented by the following optical equation is established.

$$N = n - ik \quad (8)$$

Also, when the incident angle is assumed to be φ and the wavelength of the irradiated light is assumed to be λ, as for the amplitude ratio Ψ and the phase difference Δ that are outputted by the data acquisition device 8 and measured by the ellipsometer 70, with regard to the film thicknesses d, the refractive indexes n and the extinction coefficients k of the respective layers of the evaporation product 56 to be analyzed, the relation of the following equation (9) is established.

$$(d,n,k)=F(\rho)=F(\Psi(\lambda,\phi),\Delta(\lambda,\phi)) \quad (9)$$

Note that the computer 90 uses the film thicknesses of the respective layers to be analyzed and the dispersion formula indicating the wavelength dependence of the complex dielectric constant having the plurality of parameters and carries out the process (fitting) for changing the film thicknesses, the parameters of the dispersion formula and the like, so as to minimize the difference between the model spectrum ($\Psi_M(\lambda_i)$, $\Delta(\lambda_i)$) obtained by the theoretical calculation from the stored model and the measurement spectrum ($\Psi_E(\lambda_i)$, $\Delta_E(\lambda_i)$) related to the measurement result outputted by the data acquisition device 8. Note that one example of the application dispersion formula is indicated by the following equation (10).

$$\varepsilon = \varepsilon_\infty + \frac{(\varepsilon_S - \varepsilon_\infty)\varpi_t^2}{\varpi_t^2 - \varpi^2 + i\Gamma_0\varpi} + \frac{\varpi_p^2}{-\varpi^2 + i\Gamma_D\varpi} + \sum_{j=1}^{2} \frac{f_j\varpi_{oj}^2}{\varpi_{oj}^2 - \varpi^2 + i\gamma_j\varpi}$$

In the equation (10), $\in$ on the left side represents the complex dielectric constant, and $\in_\infty$, $\in_s$ represent the dielectric constants, and $\Gamma_0$, $\Gamma_D$, $\gamma_j$ represent damping factors for the viscous force, and $\omega_{oj}$, $\omega_t$, $\omega_p$ represent the intrinsic angular frequencies (the oscillator frequency, the transverse frequency, and the plasma frequency). Note that $\in_\infty$ is the high frequency dielectric constant, and $\in_s$ is the static dielectric constant. Also, as for the complex dielectric constant $\in$ (corresponding to $\in(\lambda)$) and the complex refractive index N (corresponding to $N(\lambda)$), the relation of the following equation (11) is established.

$$\in(\lambda)=N^2(\lambda) \quad (11)$$

Note that, when the fitting is simply explained, in the case that the sample 50 is measured, let us suppose that T measurement data pairs are Exp (i=1, 2 . . . , T) and T model calculation data pairs are Mod (i=1, 2 . . . , T). Then, when the measurement error is considered to have the normal distribution and when the standard deviation is assumed to be $\sigma_i$, the mean square error $\chi^2$ related to the least squares method is calculated from the following equation (12). Note that P is the numeral of the parameters. When the value of the mean square error $\chi^2$ is small, this implies that the coincidence degree between the measurement result and the prepared model is high. Thus, when the plurality of models are compared, the model having the smallest value of the mean square error $\chi^2$ corresponds to the best model.

$$x^2 = [1/(2T-P)]\sum_{i=1}^{T}(\text{Exp}_i - \text{Mod}_i)^2/\sigma_i^2 \quad (12)$$

The series of the processes related to the sample analysis executed by the computer 90 as mentioned above are defined by the computer program for the sample analysis which is stored in the storage unit 95.

Figure 20:
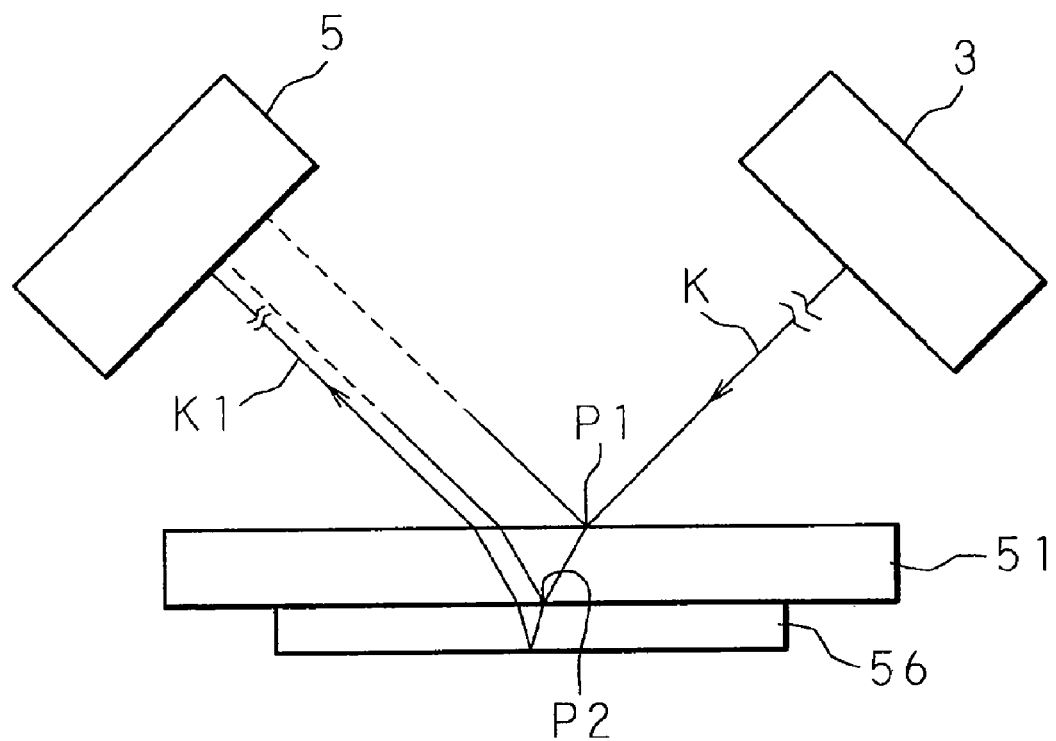
FIG. 20 is a diagrammatic lateral sectional view showing routes of an incident light and a reflected light.

FIG. 20 is a diagrammatic lateral sectional view showing the routes of the incident light and the reflected light. The incident beam K irradiated from the light irradiator 3 is inputted through the glass substrate 51 to the evaporation product 56 and reflected on the bottom surface of the evaporation product 56. The reflected beam K1 reflected on the bottom surface is again inputted through the evaporation product 56 and the glass substrate 51 to the light obtainer 5. Note that, although the reflection or multi reflection is induced at an intersection point P1 of the incident beam K and the top surface of the glass substrate 51 and at an intersection point P2 of the incident beam K and the top surface of the evaporation product 56, it is included in the selection of the model to be used for the analysis.

Figure 21:
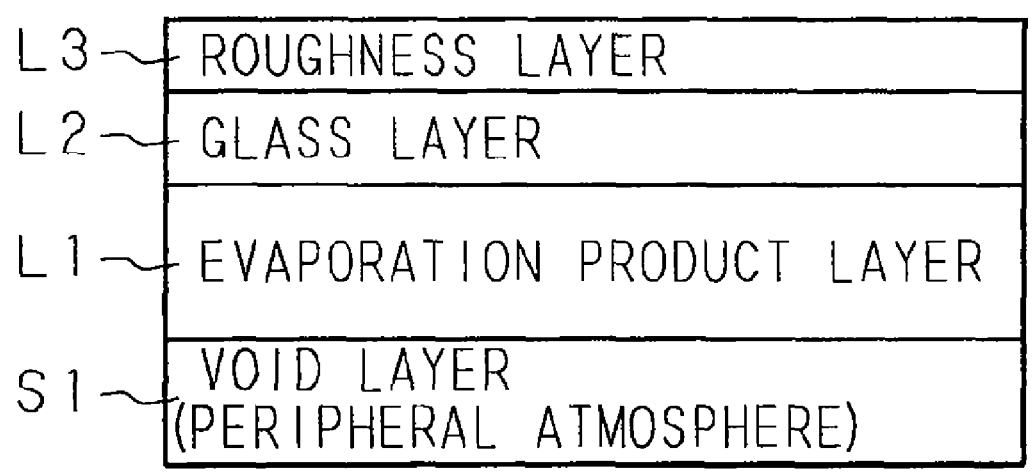
FIG. 21 is an explanation view showing a model to analyze a sample.

FIG. 21 is an explanation view showing the model to analyze the sample 50. In the ellipsometer 70, the measurement is carried out from the direction opposite to the deposition direction of the evaporation product 56. Thus, as the model for the analysis, the element in which a void layer (peripheral atmosphere) S1, an evaporation product layer L1, a glass layer L2 and a roughness layer L3 are deposited in turn is used. That is, the space on the lower side of the evaporation product 56 is defined as the void layer (peripheral atmosphere) S1, and this is regarded as the substrate. Then, the evaporation product 56 is defined as the evaporation product layer L1, the portion without any surface roughness of the glass substrate 51 is regarded as the glass layer L2, and the portion corresponding to the surface roughness of the glass substrate 51 is regarded as the roughness layer L3.

Figure 22A:
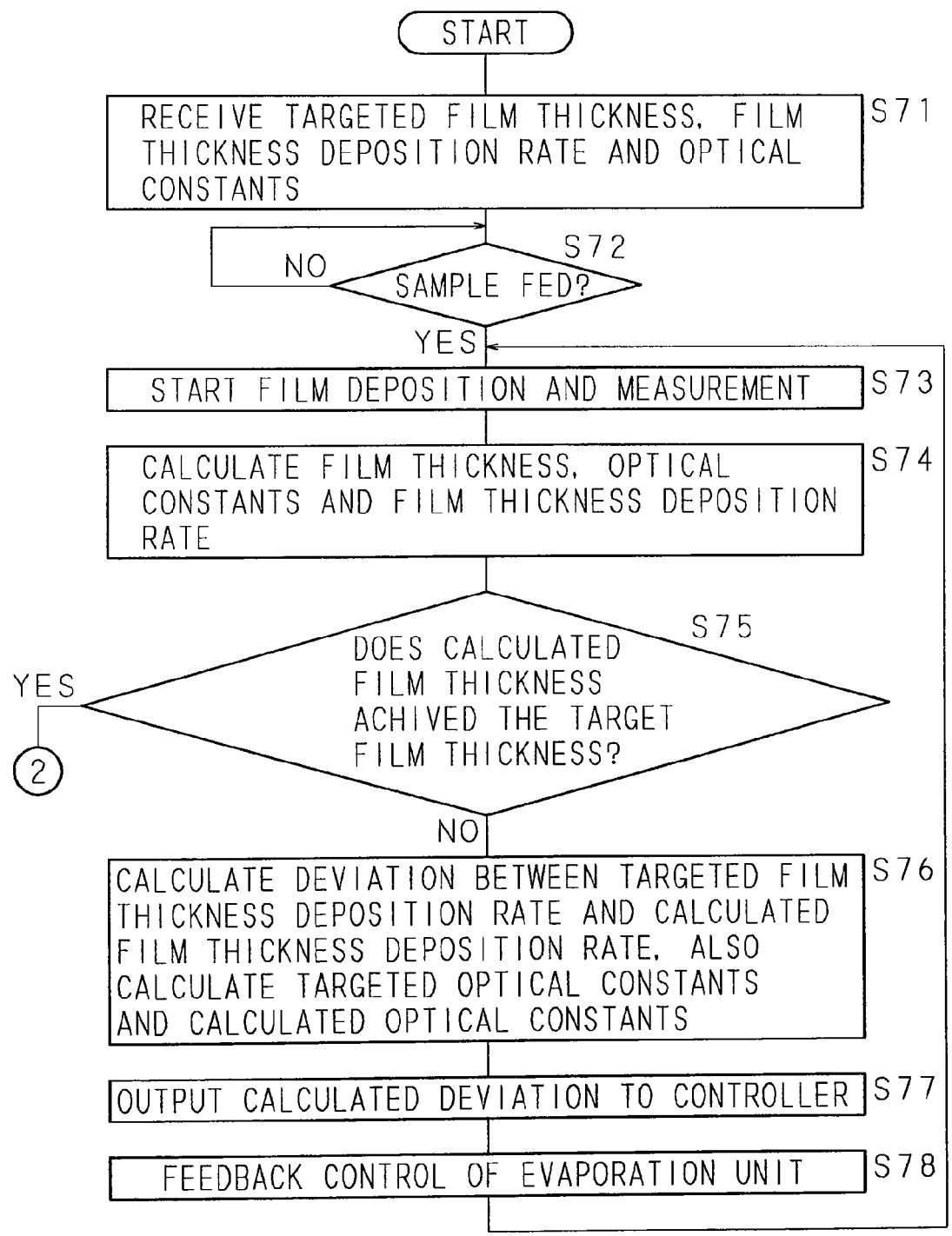
FIGS. 22A and 22B are flowcharts showing procedures of film deposition and measurement processes.
Figure 22B:
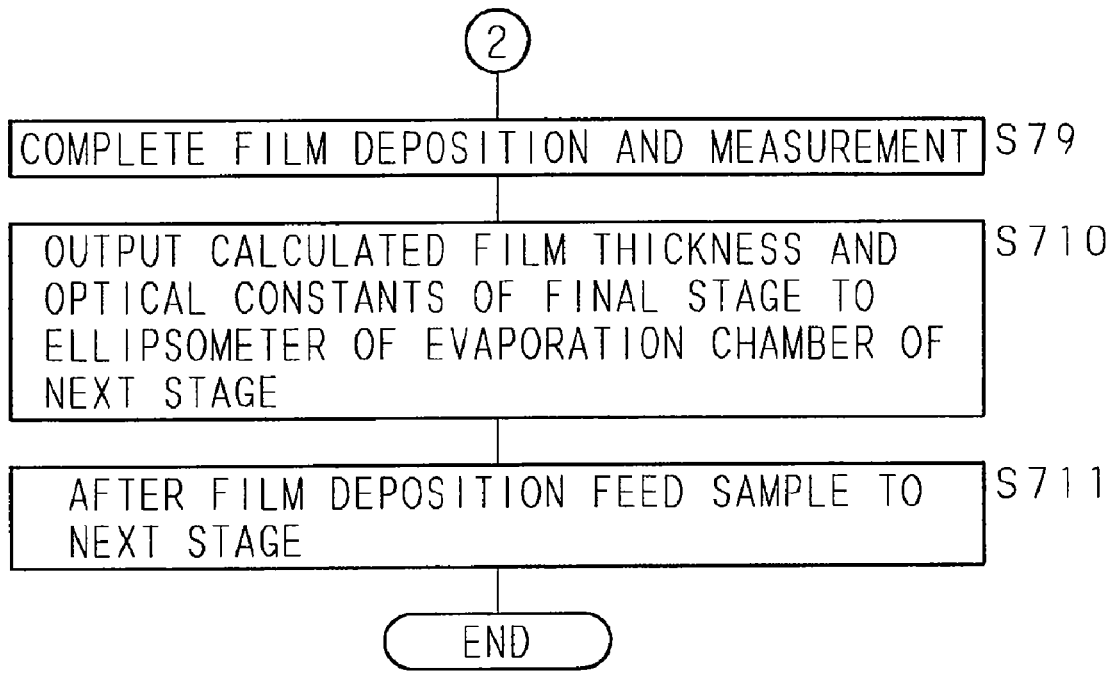

In the foregoing configuration, the procedure of the calculation process of the film thickness will be described below by using flowcharts. FIGS. 22A and 22B are the flowcharts showing the procedures of the film deposition and the calculation process. The user inputs the targeted film thickness of the layer on which the evaporation is performed in the evaporating chamber 12, the film thickness deposition rate (velocity), and the refractive index and the extinction coefficient (hereafter, they are referred as the optical constants) from the keyboard 93. Note that the values having the allowable ranges of several % for the targeted film thickness, the film thickness deposition rate and the optical constant may be inputted. Moreover, as for the input film thickness deposition rate, in the case that it comes close to the targeted film thickness, the rate may be slow down. The CPU 91 receives the inputted target film thickness, the film thickness deposition rate and the optical constant (Step S71) and stores in the RAM 92. The controller 127 of the evaporating chamber 12 monitors whether or not the sample 50 is fed to the evaporation position, and if the sample 50 is fed to the evaporation position, outputs its fact to the CPU 91 of the ellipsometer 70. The CPU 91 judges whether or not the sample 50 is fed to the evaporation position (Step S72), namely, judges whether or not the controller 127 outputs the signal indicating that the sample 50 is fed to the evaporation position.

The CPU 91, if judging that the sample 50 is not fed (Step S72: NO), waits for the fact that the sample 50 is fed. On the other hand, the CPU 91, if judging that the sample 50 is fed (Step S72: YES), the film deposition and the measurement of the ellipsometer 70 are started (Step S73). The controller 127 actuates the evaporation unit 124 and evaporates the evaporation product 56 on the glass substrate 51. The CPU 91 of the ellipsometer 70 executes the computer program for the sample analysis stored in the storage unit 95 and calculates the film thickness, the optical constant and the film thickness deposition rate (Step S74). Note that the film thickness deposition rate can be calculated by using the calculated film thickness and the measurement speed (for example, 200 ms, and this may be properly set to 100 ms or 50 ms, depending on the film deposition rate of the evaporation product) of the ellipsometer 70.

The CPU 91 compares the calculated film thickness and the target film thickness stored in the RAM 92 and judges whether or not the calculated film thickness arrives at the target film thickness (Step S75). The CPU 91, if judging that it does not arrive at the target film thickness (Step S75: NO), calculates the deviation between the targeted optical constant and the calculated optical constant and the deviation between the targeted film thickness deposition rate and the calculated film thickness deposition rate, respectively (Step S76). The CPU 91 outputs the calculated deviations to the controller 127 (Step S77).

The controller 127 carries out a feedback control of the evaporation unit 124 so that the output deviation becomes approximately zero (Step S78). Specifically, if the film thickness deposition rate is faster than the target, namely, if a negative deviation signal is outputted, the output of the evaporation unit 124 is decreased. On the other hand, if the film thickness deposition rate is slower than the target, namely, if a positive deviation signal is outputted, the output of the evaporation unit 124 is increased. Also, if the optical constant is greater than the target optical constant, namely, if the negative deviation signal is outputted, the output of the evaporation unit 124 is increased. On the other hand, if the optical constant is smaller than the target optical constant, namely, if the positive deviation signal is outputted, the output of the evaporation unit 124 is decreased. After that, the operational flow proceeds to the step S73, and the foregoing processes are repeated.

At the step S75, if the CPU 91 judges that the calculated film thickness arrives at the target film thickness (Step S75: YES), the processes at the steps S76 to S78 are skipped to then finish the film deposition in the evaporating chamber 12 and the measurement of the ellipsometer 70 (Step S79). The CPU 91 outputs the film thickness calculated at the final stage of the step S74 and the optical constant to the ellipsometer 70 of the evaporating chamber 13 of the next stage (Step S710). After that, the feeding robot 11 feeds the sample 50 after the film deposition to the evaporating chamber 13 of the next stage (Step S711).

Figure 23A:
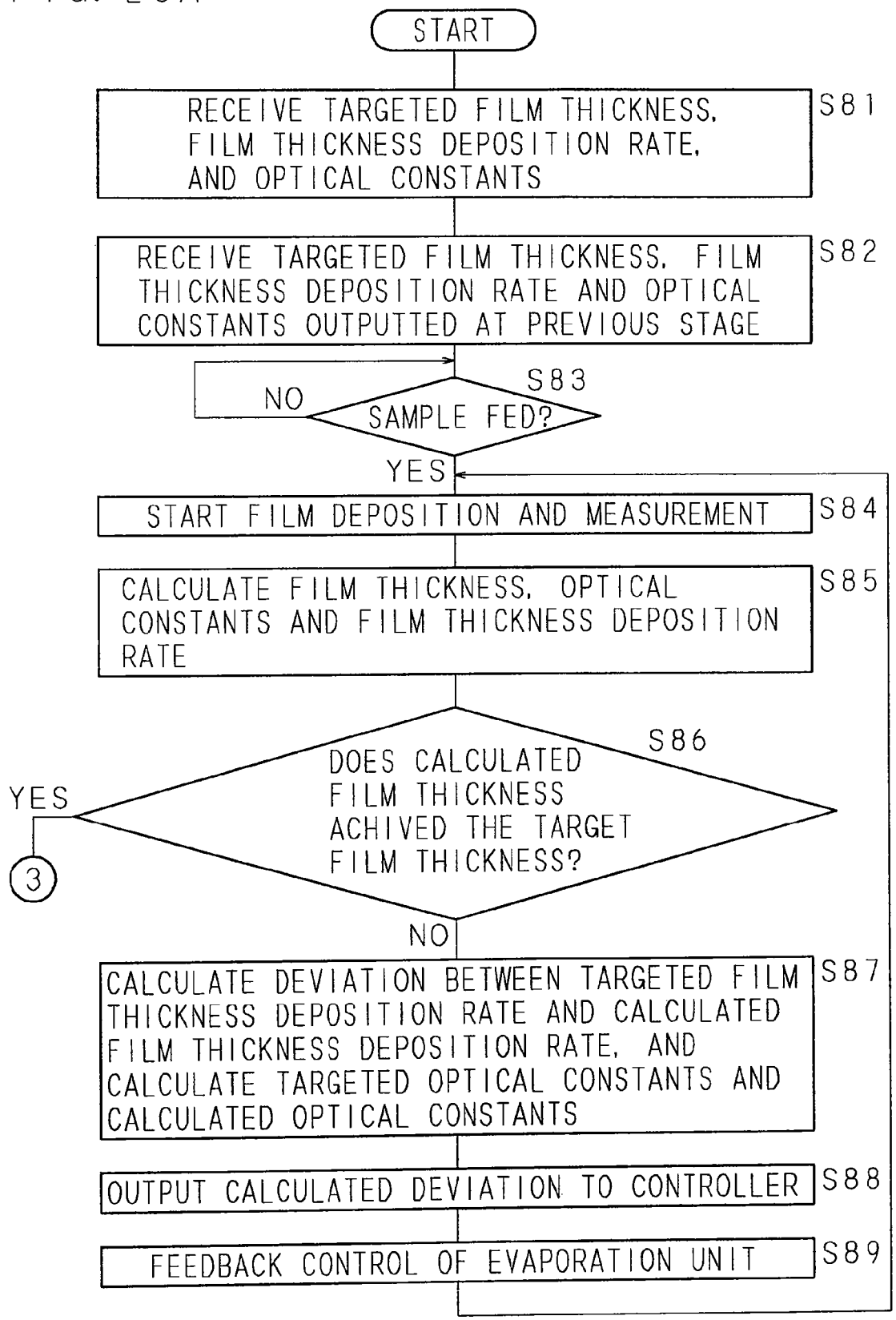
FIGS. 23A and 23B are flowcharts showing procedures of film deposition and measurement processes of a second layer.
Figure 23B:
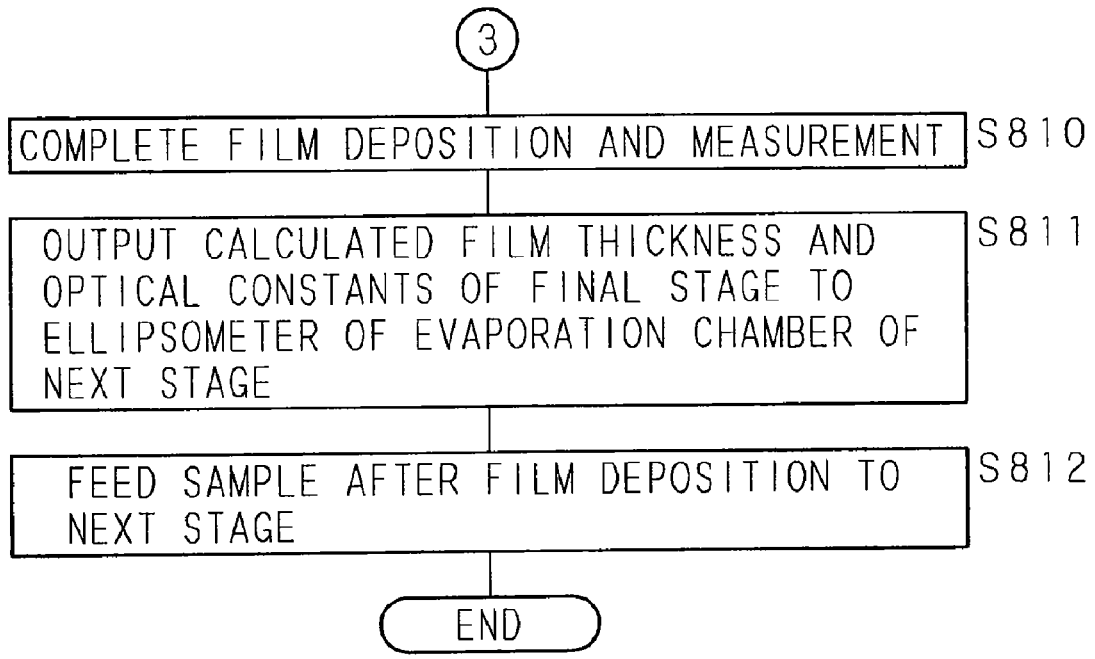

FIGS. 23A and B are flowcharts showing the procedure of the film deposition of the second layer and the measurement process. The CPU 91 receives the input target film thickness of the second layer, the film thickness deposition rate and the optical constant (Step S81) and stores in the RAM 92. Also, the CPU 91 reads the calculation film thickness and the optical constant of the former stage (first layer) outputted from the evaporating chamber 12 of the former stage at the step 710 (Step S82). The controller 127 of the evaporating chamber 13 monitors whether or not the sample 50 is fed to the evaporation position, and if the sample 50 is fed to the evaporation position, outputs its fact to the CPU 91 of the ellipsometer 70. The CPU 91 judges whether or not the sample 50 is fed to the evaporation position (Step S83), namely, judges whether or not the controller 127 outputs the signal indicating that the sample 50 is fed to the evaporation position.

The CPU 91, if judging that the sample 50 is not fed (Step S83: NO), waits for the fact that the sample 50 is fed. On the other hand, the CPU 91, if judging that the sample 50 is fed (Step S83: YES), the film deposition and the measurement of the ellipsometer 70 are started (Step S84). The CPU 91 of the ellipsometer 70 executes the computer program for the sample analysis stored in the storage unit 95 and calculates the film thickness, the optical constant and the film thickness deposition rate (Step S85). Note that the CPU 91 can use the film thickness and the optical constant, which is read at the step S82 and calculated at the former stage, as the parameters and may further use the target film thickness and the optical constant of the former stage received at the step S71 as the parameters.

The CPU 91 compares the calculated film thickness and the target film thickness stored in the RAM 92 and judges whether or not the calculated film thickness arrives at the target film thickness (Step S86). The CPU 91, if judging that it does not arrive at the target film thickness (Step S86: NO), calculates the deviation between the targeted optical constant and the calculated optical constant and the deviation between the targeted film thickness deposition rate and the calculated film thickness deposition rate, respectively (Step S87). The CPU 91 outputs the calculated deviations to the controller 127 (Step S88).

The controller 127 carries out the feedback control of the evaporation unit 124 so that the output deviation becomes approximately zero (Step S89). After that, the operational flow proceeds to the step S84, and the foregoing processes are repeated. At the step S86, if the CPU 91 judges that the calculated film thickness arrives at the target film thickness (Step S86: YES), the processes at the steps S87 to S89 are skipped to then finish the film deposition in the evaporating chamber 13 and the measurement of the ellipsometer 70 (Step S810). The film thickness and the optical constant calculated at the final stage of the step S85 are outputted to the ellipsometer 70 of the evaporating chamber 14 of the next stage (Step S811). After that, the feeding robot 11 feeds the sample 50 after the film deposition to the evaporating chamber 14 of the next stage (Step S812). Note that the processes after the evaporating chamber 14 of the next stage are similar, and their explanations are omitted.

Third Embodiment

Figure 24:
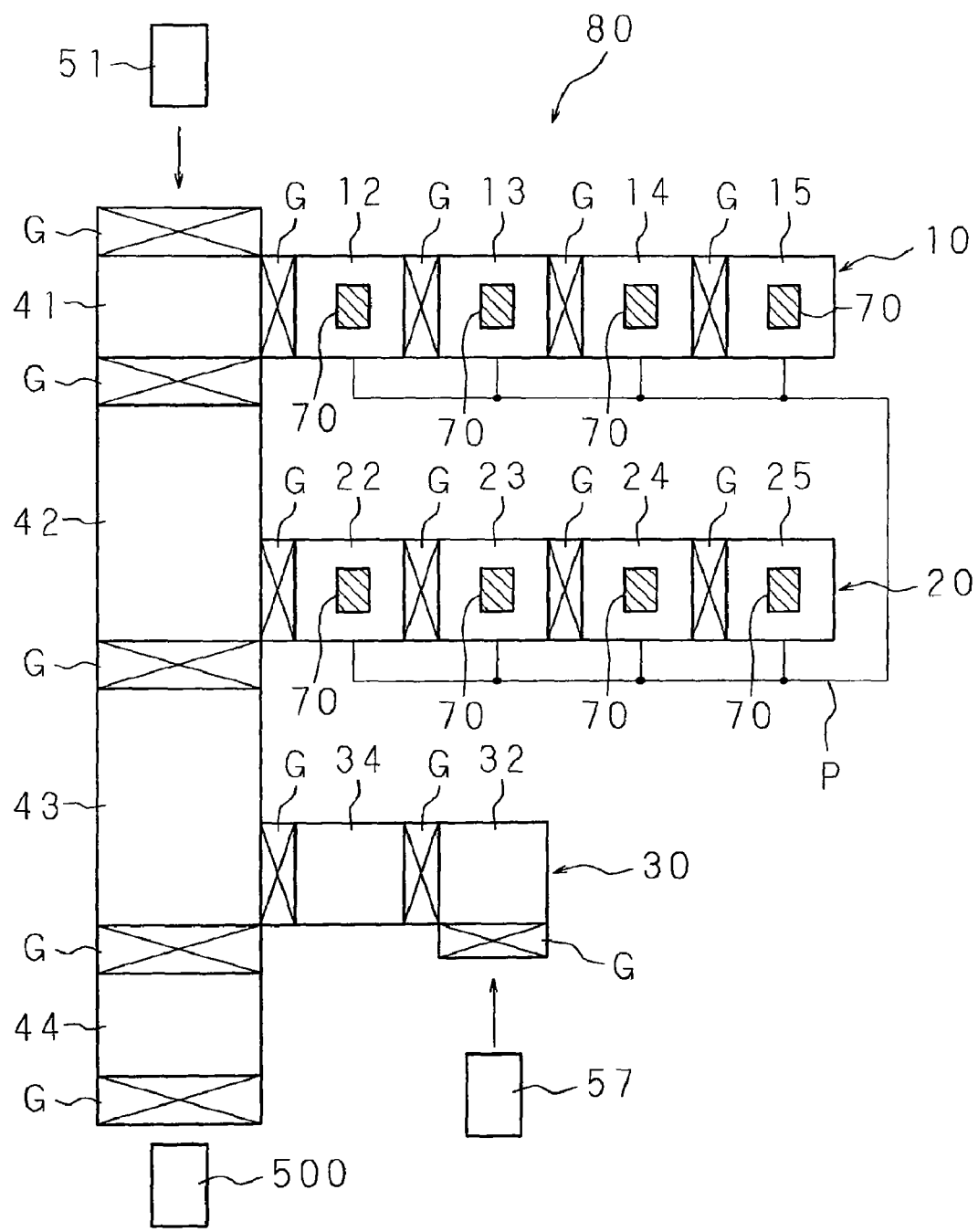
FIG. 24 is a schematic plan view showing a schema of a manufacturing equipment according to a third embodiment.

FIG. 24 is a schematic plan view showing the schema of a manufacturing equipment 80 according to the third embodiment. An in-line type shown in FIG. 24 may be applied to the manufacturing equipment 80. The manufacturing equipment 80 is provided with: the two series of the first film forming cluster 10 and the second film forming cluster 20 for evaporating the evaporation product 56 on the glass substrates 51; and the sealing cluster 30 where the sealing substrate 57 is stuck to the glass substrate 51 on which the evaporation product 56 is evaporated and the organic EL element panel 500 is discharged. The glass substrate 51 is fed to the first film forming apparatus 10 and the second film forming apparatus 20 and fed to the sealing cluster 30 after the evaporation product 56 is evaporated. In the sealing cluster 30, after the sealing substrate 57 is stuck to the glass substrate 51 on which the evaporation product 56 is evaporated, the organic EL element panel 500 as the completion product is discharged to outside.

The first film forming apparatus 10 is provided with the substrate feeding chamber 41, the evaporating chambers 12 to 15, the ellipsometers 70 and the vacuum gates G. In the first film forming apparatus 10, the evaporating chambers 12 to 15 are laterally linked through the gates G. Also, the ellipsometers 70 are installed in the respective evaporating chambers 12 to 15. The glass substrate 51 fed to the substrate feeding chamber 41 is fed to the evaporating chamber 12, and the film deposition and the measurement process are performed thereon, as mentioned above. Note that the feeding of the glass substrate 51 is carried out by the feeding robot, similarly to the foregoing explanation in the second embodiment.

The second film forming apparatus 20 linked to the receiving/passing chamber 42 is also provided with the vacuum gates G, the evaporating chambers 22 to 25 and the ellipsometers 70, similarly to the first film forming apparatus 10. The film deposition of the evaporation product 56 and the measurement process are carried out in the respective evaporating chambers 22 to 25 and the ellipsometers 70. The respective evaporating chambers 12 to 15 and 22 to 25 are connected to each other through the data transmission device P. In the case of the completion of the film deposition of the evaporation product 56, the glass substrate 51 is fed through the receiving/passing chamber 43 to the sealing cluster 30.

The sealing cluster 30 linked to the receiving/passing chamber 43 is provided with the vacuum gate G, the sealing chamber 34 and the sealing substrate feeding chamber 32. The glass substrate 51 after the completion of the evaporations on all of the layers is fed to the sealing chamber 34, and the sealing substrate 57 fed to the sealing substrate feeding chamber 32 is similarly fed to the sealing chamber 34. The glass substrate 51 on which the evaporation product 56 is evaporated and the sealing substrate 57 are stuck to each other through the adhesive in the sealing chamber 34, and the organic EL element panel 500 after the sticking is fed through the discharging chamber 44 to the outside.

Fourth Embodiment

Figure 25:
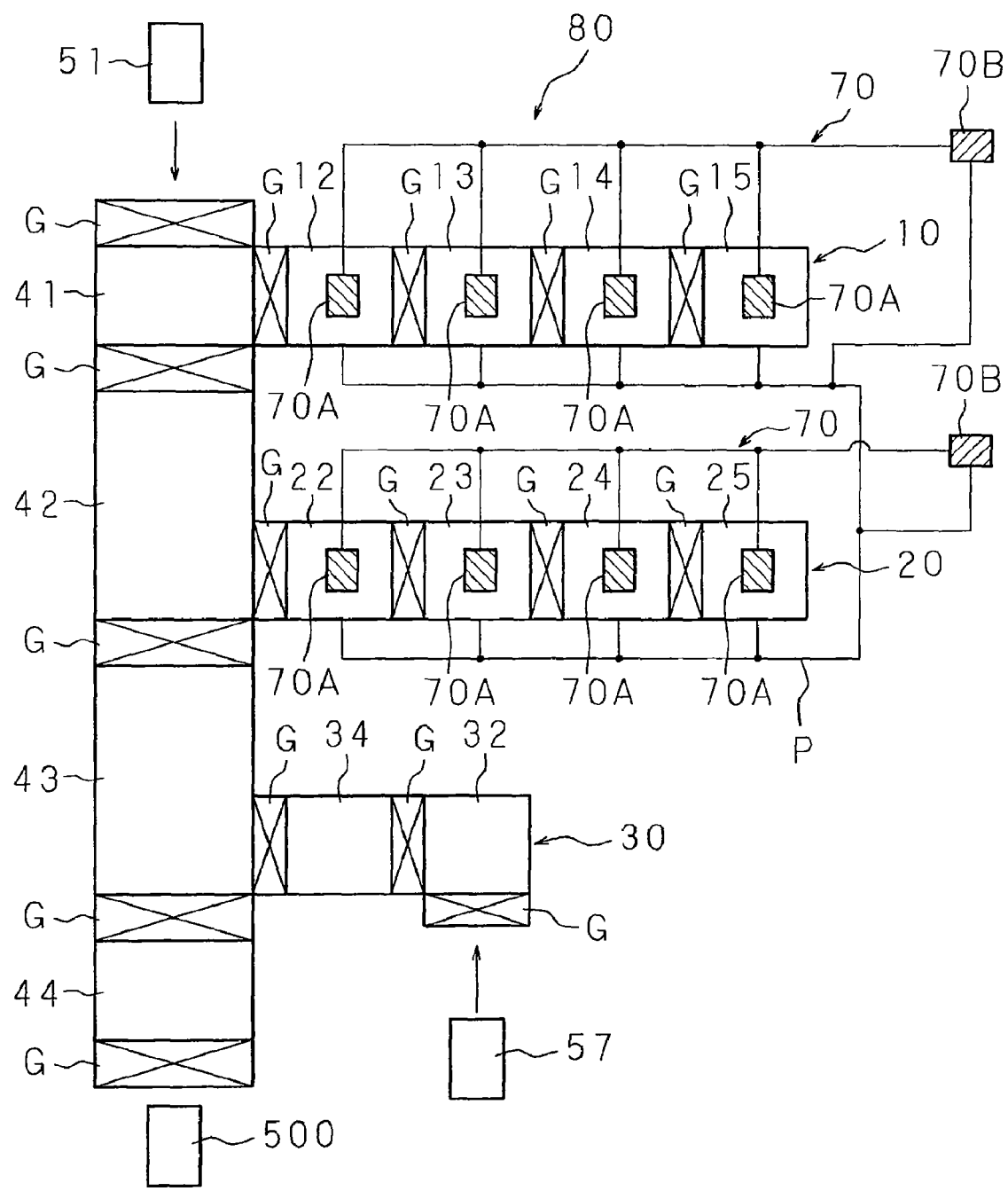
FIG. 25 is a schematic plan view showing a schema of a manufacturing equipment according to a fourth embodiment.

FIG. 25 is a schematic plan view showing the schema of the manufacturing equipment 80 according to the fourth embodiment. The ellipsometer 70 is installed in each of the evaporating chambers 12 to 15. In addition, as described in this embodiment, a light irradiating/obtaining unit 70A including at least the light irradiator 3 and the light obtainer 5 is installed in each of the evaporating chambers 12 to 15 and 22 to 25, and one calculation unit 70B including the computer 90 for calculating at least the film thickness, the refractive index that is the optical constant, the extinction coefficient, the film thickness deposition rate and the like is connected to each light irradiating/obtaining unit 70A, and may be used as the ellipsometer 70. The light irradiating/obtaining unit 70A is installed in each of the evaporating chambers 12 to 15, and the measured data is outputted to the light irradiating/obtaining unit 70A and the calculation unit 70B connected to the data transmission device P. Similarly, in the second film forming apparatus 20, the light irradiating/obtaining unit 70A is installed in each of the evaporating chambers 22 to 25, and one calculation unit 70B to be connected thereto is installed.

The various equipments such as the data acquisition device 8 constituting the ellipsometer 70 and the like may be installed on each side of the light irradiating/obtaining unit 70A and the calculation unit 70B, depending on the design of the manufacturing equipment 80. In this way, since the calculation unit 70B including the computer 90 of the ellipsometer 70 is installed at one location so that the concentration process is executed, the space saving and the low cost can be attained in the manufacturing equipment 80. Note that, although this embodiment is configured to install the calculation units 70B in the respective first film forming apparatus 10 and second film forming apparatus 20, they may be integrated such that the various processes are executed in the single calculation unit 70B. Also, this embodiment is explained with regard to the case of the application to the in-line type. However, it may be applied to the manufacturing equipment of the cluster type.

Fifth Embodiment

Figure 26:
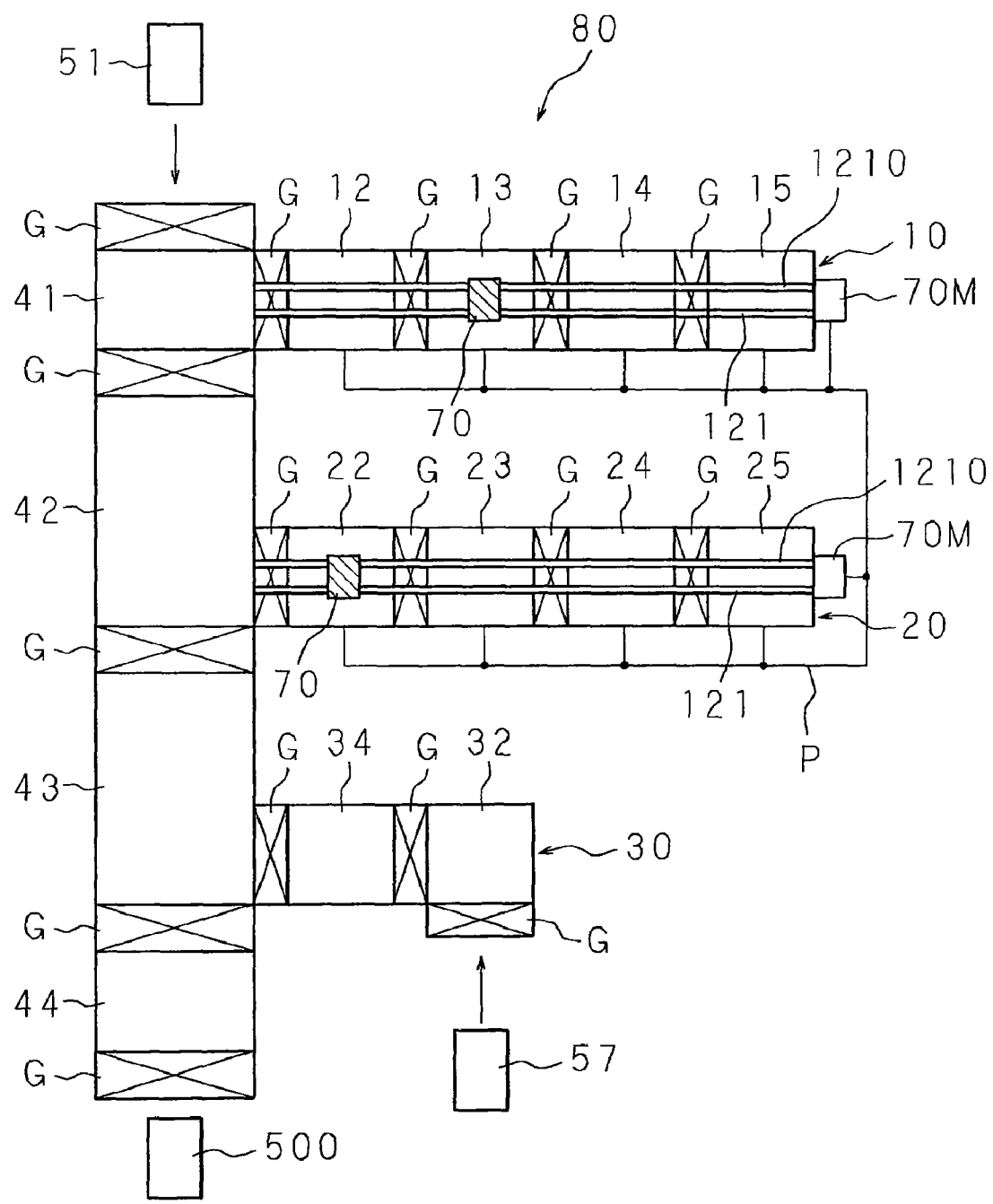
FIG. 26 is a schematic plan view showing a schema of a manufacturing equipment according to a fifth embodiment.

FIG. 26 is a schematic plan view showing the schema of the manufacturing equipment 80 according to the fifth embodiment. In the fifth embodiment, two belt conveyers 1210, 1210 in which the ellipsometer 70 is placed and which feed it are placed in each of the evaporating chambers 12 to 15 of the first film forming apparatus 10 and on the upper sides outside the respective vacuum gates G Motor 70M for driving them is installed at the final end of the belt conveyers 1210, 1210, and the motor 70M is connected to the data transmission device P. The motor 70M drives the belt conveyers 1210, 1210 and moves the ellipsometer 70 to any of the evaporating chambers 12 to 15.

Figure 27:
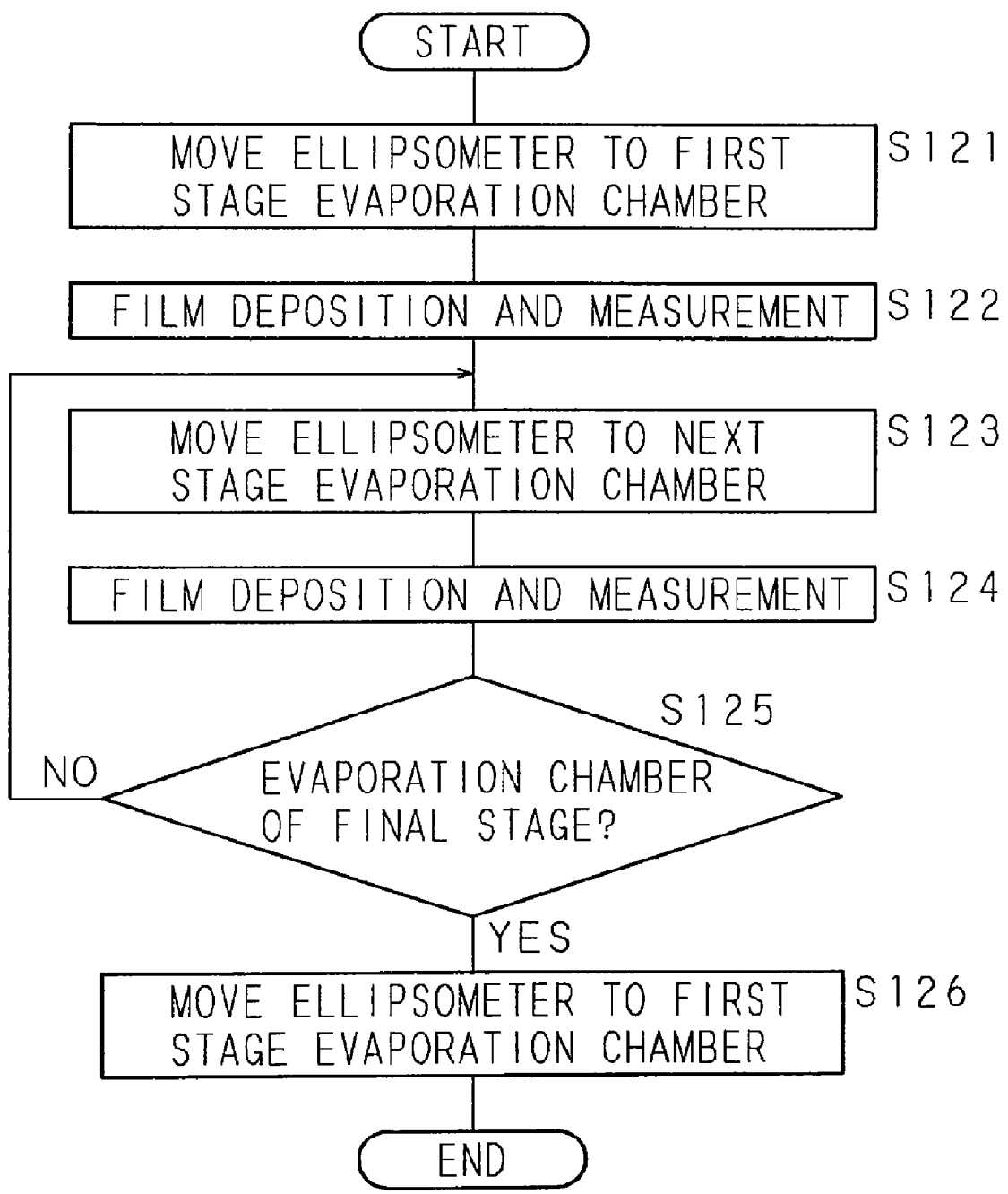
FIG. 27 is a flowchart showing a control process procedure of a motor.

The motor 70M moves the ellipsometer 70 in association with the movement of the sample 50, for the sake of the measurement of the sample 50. Similarly, the belt conveyers 1210, 1210 and the motor 70M are installed in the second film forming apparatus 20. FIG. 27 is a flowchart showing the control process procedure of the motor 70M. The motor 70M moves the ellipsometer 70 to the evaporating chamber 12 of the first stage by driving the belt conveyers 1210, 1210 (Step S121). When the sample 50 is fed to the evaporating chamber 12, the film deposition and the measurement are started (Step S122). When the process of the step S711 moves the sample 50 to the evaporating chamber 13 of the next stage, the motor 70M moves the ellipsometer 70 to the evaporating chamber 13 of the next stage, in order to follow it (Step S123).

After the film deposition and the measurement are carried out in the evaporating chamber 13 of the next stage (Step S124), the motor 70M judges whether or not the current evaporating chamber is the evaporating chamber 15 of the final stage (Step S125). If the motor 70M judges that it is not the evaporating chamber 15 of the final stage (Step S125: NO), the operational flow proceeds to the step S123, and the foregoing processes are repeated. On the other hand, if the motor 70M judges that it is the evaporating chamber 15 of the final stage (Step S125: YES), the motor 70M drives the belt conveyers 1210, 1210 and moves the ellipsometer 70 to the evaporating chamber 12 of the first stage (Step S126). In this way, since the measurement is carried out by the single ellipsometer 70, the lower cost of the manufacturing equipment 80 can be attained. Note that, although this embodiment is explained with regard to the case of the application to the in-line type, it may be applied to the manufacturing equipment of the cluster type by circumferentially installing the annular belt conveyers 1210, 1210 on the evaporating chambers 12 to 15.

The third to fifth embodiments have the foregoing configurations, and the other configurations and actions are similar to the second embodiment. Thus, the same reference numbers are assigned to the corresponding portions, and their detailed explanations are omitted.

Sixth Embodiment

Figure 28:
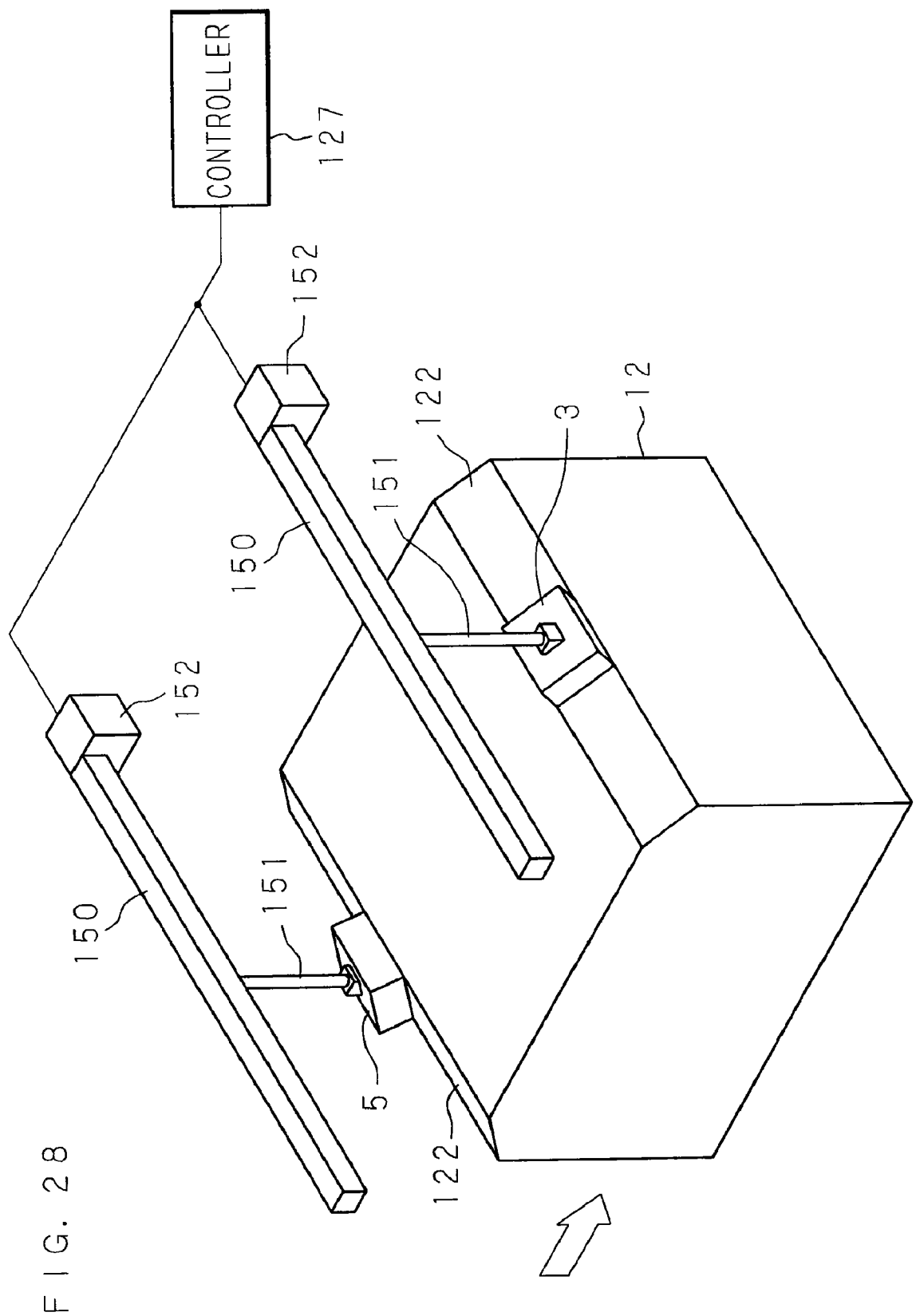
FIG. 28 is a diagrammatic perspective view showing a configuration of an evaporating chamber according to a sixth embodiment.

FIG. 28 is a diagrammatic perspective view showing the configuration of the evaporating chamber 12 according to the sixth embodiment. As shown in FIG. 28, the rectangular transmission windows 122, 122 indicated by an arrow in white of FIG. 28, in which their longitudinal directions are orthogonal to the feeding direction of the feeding device of the glass substrate 51, are extended at both ends of the upper portion opposite to the evaporation direction of the evaporating chamber 12 according to the sixth embodiment. The rectangular transmission windows 122, 122 are obliquely placed when they are viewed on the side.

Similarly to the second embodiment, above the transmission windows 122, 122, the light irradiator 3 and the light obtainer 5 that are indicated by the arrow in white, respectively, are movably placed in the direction orthogonal to the feeding direction of the glass substrate 51. The light irradiator 3 and the light obtainer 5 are attached to one ends of support bars 151, 151 that are upwardly extended. On the other hand, the other ends of the support bars 151, 151 are movably suspended from rails 150, 150 extended in the orthogonal direction.

The support bars 151, 151 suspended from the rails 150, 150 are moved in the orthogonal direction along the rails 150, 150 by drive motors 152, 152 that are operated in accordance with the control of the controller 127, and consequently move the light irradiator 3 and the light obtainer 5, which are attached to the one ends of the support bars 151, 151, to the orthogonal direction. In this way, since the light irradiator 3 and the light obtainer 5 are moved to the direction orthogonal to the feeding direction of the glass substrate 51 through the feeding device, the film thickness can be measured in the wide range on the glass substrate 51. Note that, although this embodiment is configured so as to movably place the light irradiator 3 and the light obtainer 5 in the direction orthogonal to the feeding direction of the glass substrate 51, this is not limited thereto. For example, the configuration may be employed in which the transmission window whose longitudinal direction is the direction parallel to the feeding direction of the glass substrate 51 is placed and the light irradiator 3 and the light obtainer 5 are movably placed in this parallel direction.

The sixth embodiment has the foregoing configurations, and the other configurations and actions are similar to the second embodiment. Thus, the same reference numbers are assigned to the corresponding portions, and their detailed explanations are omitted.

Seventh Embodiment

Figure 29:
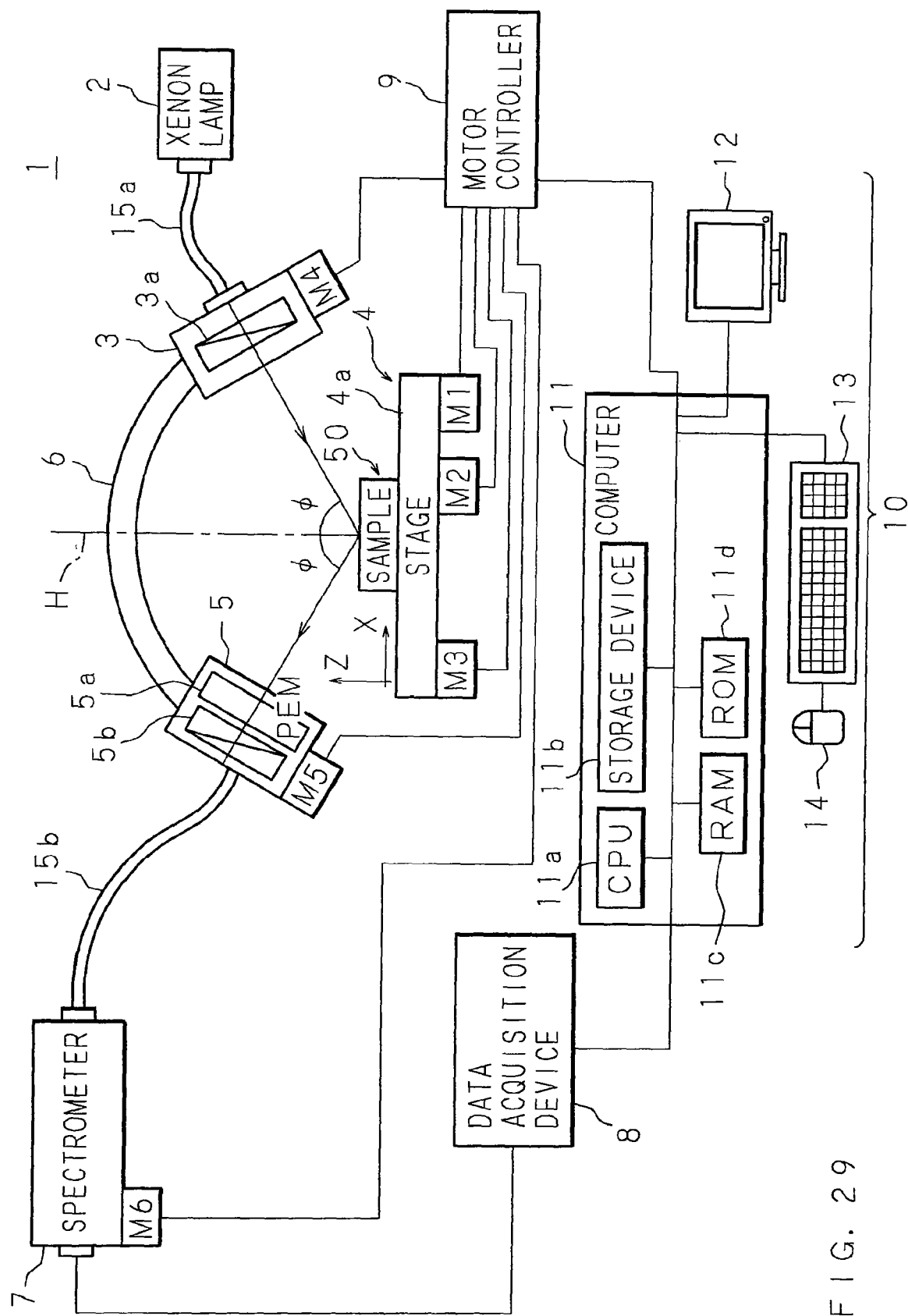
FIG. 29 is a block diagram showing a hardware configuration of a sample analyzing apparatus according to an embodiment of the present invention.

The embodiment of the present invention will be described below with reference to the drawings. FIG. 29 is a block diagram showing the hardware configuration of the sample analyzing apparatus 1 according to the embodiment of the present invention. The sample analyzing apparatus 1 is provided with the ellipsometer and the computer 10 that is the analyzing device (analyzing unit). The sample analyzing apparatus 1 irradiates the polarized light to the sample 50 where a multi-layer structure (plurality of films) are deposited, obtains the light reflected on the sample 50, and measures the polarization state of the reflected light and then analyzes the characteristics of the respective film layers of the sample 50 in accordance with this measurement result and the model corresponding to the sample 50. The embodiment for analyzing the organic EL element panel 50 as the sample 50 through the sample analyzing apparatus 1 will be described below. Note that instead of the ellipsometer, the polarimeter can be used in the sample analyzing apparatus 1.

Figure 30A:
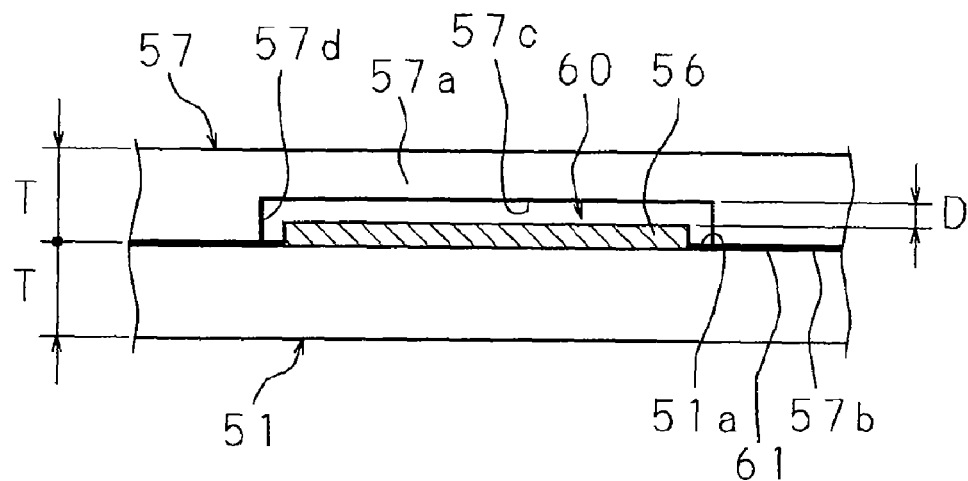
FIGS. 30A and B are diagrammatic sectional views showing a deposition state of an organic EL element.

FIGS. 30A and B are diagrammatic sectional views showing the deposition state of the organic EL element panel 50. The organic EL element panel 50 is provided with a transparent substrate 51 such as a glass substrate and the like, the organic film 56 and the cover material 57 such as glass and the like. FIG. 30A is the diagrammatic sectional view showing the deposition state of the transparent substrate 51, the organic film 56 and the cover material 57. This organic EL element panel 50 is configured such that with two glass plate members, namely, the organic film 56 between, the transparent substrate 51 and the cover material 57 are stuck to each other. In the structure of the organic EL element panel 50, the organic film 56 is formed on one surface 51a of the transparent substrate 51 that is one glass plate member. On the other hand, the cover material 57 that is the other glass plate member contains the concave portion 57d in which the organic film 56 is accommodated. Then, the surface 57b containing the concave portion 57d is stuck to the one surface 51a of the transparent substrate 51 through the adhesive 61, and both of them are integrated.

The inside of the concave portion 57d sealed by the sticking between the transparent substrate 51 and the cover material 57 is made vacuum in order to protect the organic film 56, or rare gas (for example, nitrogen gas) is sealed therein. Also, in this embodiment, the glass is used in the cover material 57 and the transparent substrate 51. However, it is not limited to this. For example, as the transparent substrate 51, a flexibly transparent plastic substrate may be used. When the transparent plastic substrate is used, after the thin film (ITO and the like) of the transparent conductive property is coated on the transparent plastic substrate, the organic film 56 may be formed thereon. Also, in the cover material 57, for example, Barix (a registered trademark) that is transparent in a visible region can be used as the sealing film, and this may be stuck on the transparent plastic substrate.

Figure 30B:
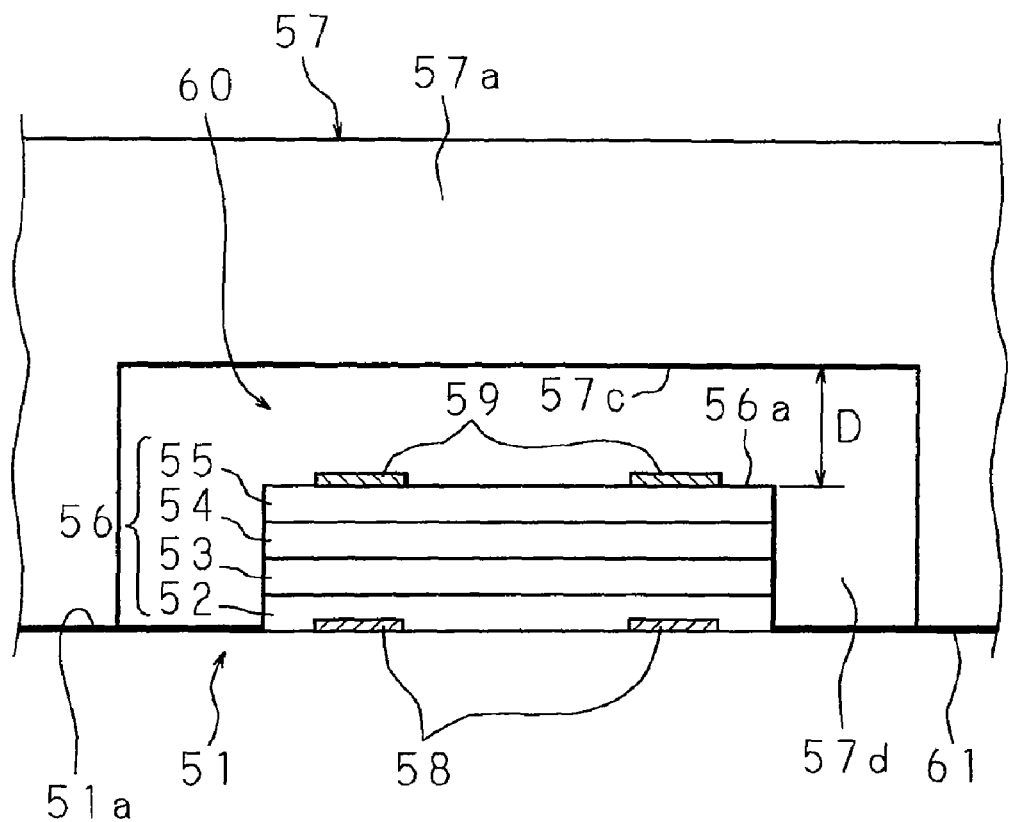

FIG. 30B shows the detailed structure of the organic film 56 accommodated in the concave portion 57d. In the organic film 56, on the anode (ITO) 58 that is the transparent electrode arranged on the one surface 51a of the transparent glass substrate 51, the total of the 4 layers of the film layers composed of: the hole transport layer 52, the emitting layer 53, the hole blocking layer 54 and the electron transport layer 55 are sequentially stacked. Also, in the organic film 56, the cathode 59 is arranged on the surface 56a opposite to the cover material 57.

The organic film 56 is accommodated in the concave portion 57d at the gap (gap), and there is the space 60 from a cover portion 57a of the cover material 57 for covering the surface 56a of the organic film 56. The thickness dimension D of the space 60 (the vertical dimension to the inner surface 57c of the cover portion 57a from the surface 56a of the organic film 56, and this corresponds to the gap distance) is various depending on the specification of the organic EL element panel 50. Typically, the thickness dimension D is set in the range between 10 μm and 400 μm, in many cases. Note that in the glass substrate 51 and the cover material 57, the thickness T of 0.5 mm, 0.7 mm or 1.1 mm is used in many cases (0.7 mm is the most typical thickness). Thus, the entire thickness (2T) of the organic EL element panel 50 typically has the dimension in the range between 1.0 mm and 2.2 mm.

The sample analyzing apparatus 1 for analyzing the organic film 56 of the organic EL element panel 50 of the foregoing structure is configured as shown in FIG. 29, and it is roughly classified into the portion of the measurement analysis group, which includes the measuring unit composed of a pair of the light irradiator 3 and the light obtainer 5, and the drive group portion. The sample analyzing apparatus 1 is configured such that as the portion of the measurement analysis group, the xenon lamp 2 and the light irradiator 3 are connected through the first optical fiber cable 15a, and the light of the polarization state is irradiated onto the sample (organic EL element panel 50) placed on the stage 4 (sample table), and the light is inputted to the sample, and the light reflected on the sample is acquired by the light obtainer 5. The light obtainer 5 is connected through the second optical fiber cable 15b to the spectrometer 7. The spectrometer 7 carries out the measurement for each wavelength and transmits the measurement result as the analog signal to the data acquisition device 8. The data acquisition device 8 converts the analog signal into the necessary value and transmits to the computer 10, and the analysis is carried out by the computer 10.

Also, as shown in FIG. 29, in the sample analyzing apparatus 1, as the drive group portion, the first motor M1 to the sixth motor M6 are installed in the stage 4, the light irradiator 3, the light obtainer 5 and the spectrometer 7, respectively. Since the drives of the respective motors M1 to M6 are controlled by the motor controller 9 connected to the computer 10, the stage 4, the light irradiator 3, the light obtainer 5 and the spectrometer 7 are changed to the suitable positions and poses corresponding to the measurements. The motor controller 9 performs the drive control on the respective motors M1 to M6 in accordance with the indication outputted by the computer 10. Note that in the sample analyzing apparatus 1, the portion corresponding to the ellipsometer is the range mainly constituted by the xenon lamp 2, the light irradiator 3, the stage 4, the light obtainer 5, the spectrometer 7, the data acquisition device 8, the motor controller 9 and the motors M1 to M6.

The foregoing respective portions of the sample analyzing apparatus 1 will be detailed below in turn. At first, the xenon lamp 2 serves as the light source, and generates the white light including the plurality of wavelength components and then sends the generated white light through the first optical fiber cable 15a to the light irradiator 3. The light irradiator 3 is arranged on the rail 6 having the shape of the half circular arc and has the polarizer 3a therein. Then, the white light is polarized by the polarizer 3a, and the light of the polarization state is irradiated onto the sample. Also, the light irradiator 3 is moved along the rail 6 because the fourth motor M4 is driven, and the angle (incident angle φ) for the vertical line H of the stage surface 4a of the stage 4 with respect of the irradiated light is made adjustable.

The stage 4 is slidably arranged on the movement rail portion (not shown), and the drives of the first motor M1 to the third motor M3 enable the stage 4 to be moved in the X-direction and the Y-direction in FIG. 29 (directions orthogonal to the paper surface of FIG. 3) and the Z-direction serving as the height direction, respectively. The movement of the stage 4 enables the portion, at which the light is inputted to the sample, to be suitably changed, and the surface analysis of the sample is made possible. Note that the stage surface 4a on which the sample of the stage 4 is placed is blacked in order to present the reflection of the light.

In this embodiment, the organic EL element panel 50 is measured from the side of the transparent substrate 51 and the side of the cover material 57, respectively. At first, the procedure for measuring from the side of the transparent substrate 51 is explained.

Figure 31:
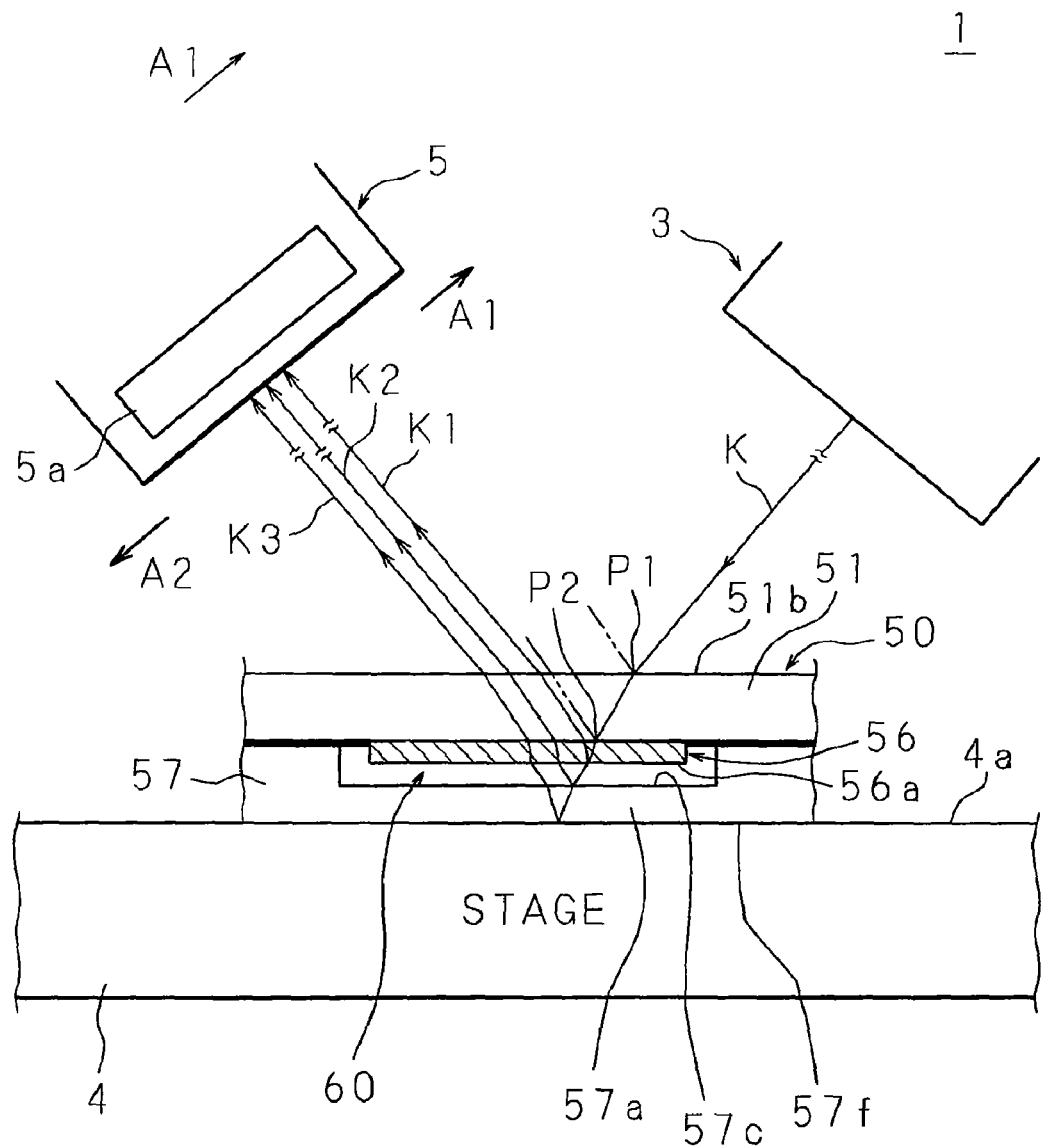
FIG. 31 is a diagrammatic sectional view showing input and reflection states of light when an organic EL element panel is measured from a transparent substrate side.

FIG. 31 is a diagrammatic sectional view showing the input and output states of the light when the organic EL element panel 50 is measured from the side of the transparent substrate 51. The organic EL element panel 50 is placed on the stage 4 so that the upper portion and the lower portion are turned over and the outer surface 57f of the cover portion 57a of the cover material 57 is consequently brought into contact with the stage surface 4a of the stage 4. Since in this situation, the light irradiator 3 irradiates the light, the light is inputted from the rear 51b of the transparent substrate 51 of the organic EL element panel 50, and passed through the transparent substrate 51 of the transparent property and sent to the organic film 56. Note that in FIG. 31, the illustrations of the anode 58, the cathode 59 and the like of the organic EL element panel 50 are omitted (FIG. 30A and FIG. 38 which will be illustrated later are similar).

Also, as shown in FIG. 29, the light obtainer 5 obtains the light reflected on the organic EL element panel 50 and measures the polarization state of the obtained light. The light obtainer 5 is arranged on the rail 6 similarly to the light irradiator 3, and the PEM (Photo Elastic Modulator) 5a and the analyzer 5b are built therein, and the light reflected on the sample is guided through the PEM 5a to the analyzer 5b. Also, the light obtainer 5 can be moved in the arrows A1, A2 directions in FIG. 31 along the rail 6 in accordance with the drive of the fifth motor M5. Basically, it is controlled by the motor controller 9 so that in linkage with the movement of the light irradiator 3, the reflection angle φ and the incident angle φ become equal in angle. Note that the PEM 5a built in the light obtainer 5 obtains the ellipse polarization from the straight polarization because the acquired light is phase-modulated at the necessary frequency (for example, 50 kHz). Also, the analyzer 5b selectively obtains and measures the polarization from the various polarizations which are phase-modulated by the PEM 5a.

As shown in FIG. 29, the reflection mirror, the diffraction grating, the photo multiplier (PMT: Photo Multiplier Tube), the control unit and the like are built in the spectrometer 7. Then, the light sent through the second optical fiber cable 15b from the light obtainer 5 is reflected by the reflection mirror and guided to the refractive grating. The refractive grating changes the angle through the sixth motor M6 and varies the wavelength of the output light. The light advanced to the inside of the spectrometer 7 is amplified by PMT, and even if the light amount is small, the measured signal (light) is made stable. Also, the control unit carries out the process for generating the analog signal corresponding to the measured wavelength and sending to the data acquisition device 8. Note that if the polarimeter is used, the configuration of the combination of photo diode arrays (PDA) is also possible.

The data acquisition device 8 calculates the amplitude ratio Ψ and the phase difference Δ with regard to the polarization state (the p-polarization and the s-polarization) of the reflected light in accordance with the signal from the spectrometer 7 and sends the calculated result to the computer 10. Note that as for the amplitude ratio Ψ and the phase difference Δ, the relation of the following equation (1) is established for the amplitude reflection coefficient Rp of the p-polarization and the amplitude reflection coefficient Rs of the s-polarization.

$$Rp/Rs = \tan \Psi \cdot \exp(i \cdot \Delta) \quad (13)$$

However, i is the imaginary unit (hereafter, similarly). Also, Rp/Rs is referred to as the polarization change amount ρ.

Also, the computer 10 of the sample analyzing apparatus 1 analyzes the sample in accordance with the amplitude ratio Ψ and the phase difference Δ of the polarization state, which are obtained by the data acquisition device 8, and the model corresponding to the sample, and also controls the movement of the stage 4 and the like.

The computer 10 is provided with the computer body 11, the display 12, the keyboard 13 and the mouse 14 and the like. In the computer body 11, the CPU 11a, the storage unit 11b, the RAM 11c and the ROM 11d are connected through the inner bus. The CPU 11a carries out the various processes with regard to the computer 10 in accordance with the various computer programs stored in the storage unit 11b. The RAM 11c transiently stores the various data and the like with regard to the processes, and the ROM 11d stores the content related to the functions of the computer 10 and the like.

Note that the storage unit 11b of the computer 10 stores in advance the various programs, such as the computer program for the sample analysis, the computer program for the movement control of the stage 4, and the like and also stores: the data of the various menu images to be displayed on the display 12; the known data related to the samples; the model patterns of the structures different from each other; the plurality of dispersion formulas used to prepare the models; the prepared models; the reference data corresponding to the various samples; the standard values to be used in the comparing process related to the interference patterns; and the like.

With regard to the analysis of the sample (organic EL element panel 50), the computer 10 analyzes the refractive indexes and the extinction coefficients (hereafter, represented by the optical constant, depending on the case) as the optical characteristics of the respective film layers 52 to 55 constituting the organic film 56 of the organic EL element panel 50 and also analyzes the film thicknesses of the respective film layers 52 to 55 and the like.

Specifically, the computer 10 uses the modeling program that is stored in advance in the storage unit 11b, if the complex refractive index of the peripheral atmosphere composed of the transparent substrate 51, the cover material 57 and the organic EL element panel 50 and the like is already known from the measured amplitude ratio Ψ and phase difference Δ. Then, the model corresponding to the items of the sample set by the user and the material structure of the organic EL element panel 50 is prepared and stored in the storage unit 11b, and the model stored at the analysis stage is used to calculate the film thicknesses and the complex refractive indexes of the respective film layers 52 to 55 of the organic film 56. As for the complex refractive index N, when the film layer to be analyzed is assumed to have the refractive index n and the extinction coefficient k, the relation of the equation (14) represented by the following optical equation is established.

$$N = n - ik \tag{14}$$

Also, when then incident angle is assumed to be ϕ and the wavelength of the light irradiated by the light irradiator 3 is assumed to be λ, as for the amplitude ratio Ψ and the phase difference Δ that are outputted by the data acquisition device 8 and measured by the ellipsometer, with regard to the film thicknesses d, the refractive indexes n and the extinction coefficients k of the film layers 52 to 55 to be analyzed, the relation of the following equation (15) is established.

$$(d, n, k) = F(\rho) = F(\Psi(\lambda, \phi), \Delta(\lambda, \phi)) \tag{15}$$

Note that the computer 10 uses the film thicknesses of the film layers 52 to 55 to be analyzed and the dispersion formula indicating the wavelength dependence of the complex dielectric constant having the plurality of parameters and carries out the process (fitting) for changing the film thicknesses, the parameters of the dispersion formula and the like, so as to minimize the difference between the model spectrum ($\Psi_M(\lambda_i), \Delta_M(\lambda_i)$) obtained by the theoretical calculation from the stored model and the measurement spectrum ($\Psi_E(\lambda_i), \Delta_E(\lambda_i)$) related to the measurement result outputted by the data acquisition device 8. Note that one example of the application dispersion formula is indicated by the following equation (16).

$$\varepsilon = \varepsilon_\infty + \frac{(\varepsilon_S - \varepsilon_\infty)\omega_t^2}{\omega_t^2 - \omega^2 + i\Gamma_0 \omega} + \frac{\omega_p^2}{-\omega^2 + i\Gamma_D\omega} + \sum_{j=1}^{2} \frac{f_j \omega_{oj}^2}{\omega_{oj}^2 - \omega^2 + i\gamma_j \omega} \tag{16}$$

In the equation (16), ∈ on the left side represents the complex dielectric constant, and $\in_\infty$, $\in_s$ represent the dielectric constants, and $\Gamma_0$, $\Gamma_D$, $\gamma_j$ represent damping factors, and $\omega_{oj}$, $\omega_t$, $\omega_p$ represent angular frequencies (the oscillator frequency, the transverse frequency, and the plasma frequency). Note that $\in_\infty$ is the high frequency dielectric constant, and $\in_s$ is tje static dielectric constant, and $f_j = (\in_{sj} - \in_\infty)$. Also, as for the complex dielectric constant s (corresponding to ∈(λ)) and the complex refractive index N (corresponding to N(λ)), the relation of the following equation (17) is established.

$$\in(\lambda) = N^2(\lambda) \tag{17}$$

Note that, when the fitting is simply explained, in the case that the organic EL element panel 50 is measured, let us suppose that the T measurement data pairs are Exp (i=1, 2 . . . , T) and the T model calculation data pairs are Mod (i=1, 2 . . . , T). Then, when the measurement error is considered to have the normal distribution and when the standard deviation is assumed to be $\sigma_i$, the mean square error $\chi^2$ related to the least squares method is calculated from the following equation (18). Note that P is the numeral of the parameters. When the value of the mean square error $\chi^2$ is small, this implies that the coincidence degree between the measurement result and the prepared model is high. Thus, when the plurality of models are compared, the model having the smallest value of the mean square error $\chi^2$ corresponds to the best model.

$$\chi^2 = [1/(2T - P)] \sum_{i=1}^{T} (\text{Exp}_i - \text{Mod}_i)^2 / \sigma_i^2 \tag{18}$$

The series of the processes related to the sample analysis executed by the computer 10 as mentioned above are defined by the computer program for the sample analysis which is stored in the storage unit 11b. In the sample analyzing apparatus 1 according to this embodiment, the model type (the structure of the model) that is preliminarily prepared so as to be able to cope with the plurality of reflection manners in the sample is stored in the storage unit 11b. The structure of the model type is read and used in the analysis in accordance with the process defined by the computer program (modeling program) stored in the storage unit 11b. Moreover, the computer program stores the program for carrying out the fitting on the basis of the measurement spectrum measured from both of the side of the transparent substrate 51 and the side of the cover material 57 and on the basis of the model spectrum of both of the side of the transparent substrate 51 and the side of the cover material 57 and then calculating the film thicknesses of the respective film layers of the organic film 56 and the optical constant.

In this embodiment, in order to measure the organic EL element panel 50 in the manner as shown in FIG. 31, as the manner that the beam K irradiated onto the organic EL element panel 50 is reflected, the 3 kinds are typically assumed. The first manner is the case that the beam K inputted to the organic EL element panel 50 is reflected on the boundary (the portion corresponding to the surface 56a of the organic film 56) between the organic film 56 and the space 60 (the optical path of the reflected beam K1 in FIG. 31). The second manner is the case that the beam K is transmitted through the organic film 56 and the space 60 and reflected on the inner surface 57c of the cover material 57 (the optical path of a reflected beam K2 in FIG. 31). The third manner is the case that it is transmitted through the cover material 57 and reflected on the boundary (the portion where the outer surface 57f of the cover material 57 and the stage surface 4a of the stage 4 are in contact with each other) between the cover material 57 and the stage 4 (the optical path of the reflected beam K3 in FIG. 5).

Actually, as shown in FIG. 31, Note that, although the reflection at the point P1 on the surface of the transparent substrate 51, the reflection at the point P2 serving as the boundary between the transparent substrate 51 and the organic film 56, and the multiple reflection are included, since the reflections at the points P1, P2 are not directly used to select the model to be used in the analysis, their treatments are omitted in this embodiment. Also, the beam K and the reflected lights K1 to K3 and the like are refracted at the time of the input to the transparent substrate 51, the organic film 56 and the like and also refracted at the time of the output. However, at this time, the angles of the input case and the output case are equal. Moreover, whether or not all of the reflected lights K1 to K3 including the multiple reflection are measured depends on the thickness dimension of the sample. Thus, the sample analyzing apparatus 1 selects even the kind of the model to be used for the analysis, in accordance with the thickness dimension of the sample.

Figure 32A:
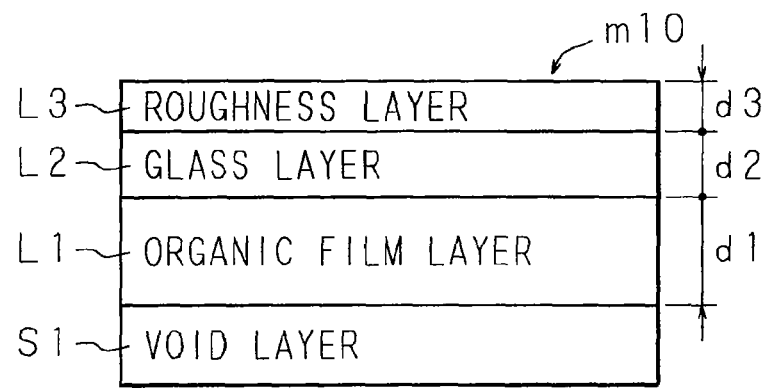
FIGS. 32A to C are explanation views showing a model at a time of a measurement from a transparent substrate side.
Figure 32B:
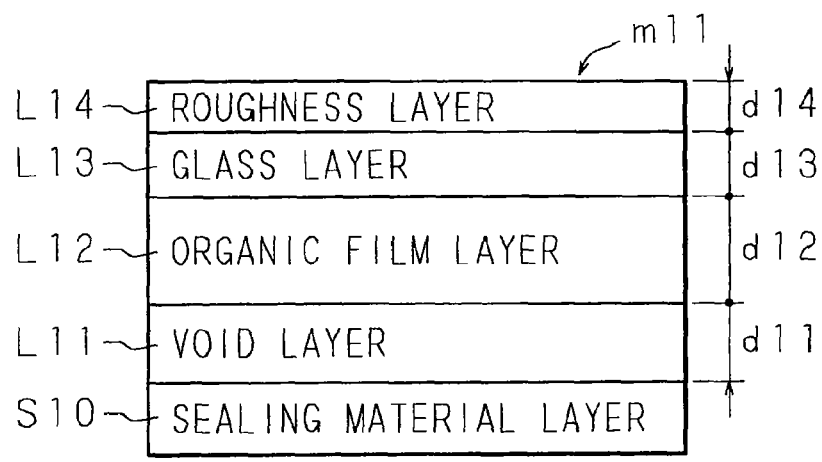
Figure 32C:
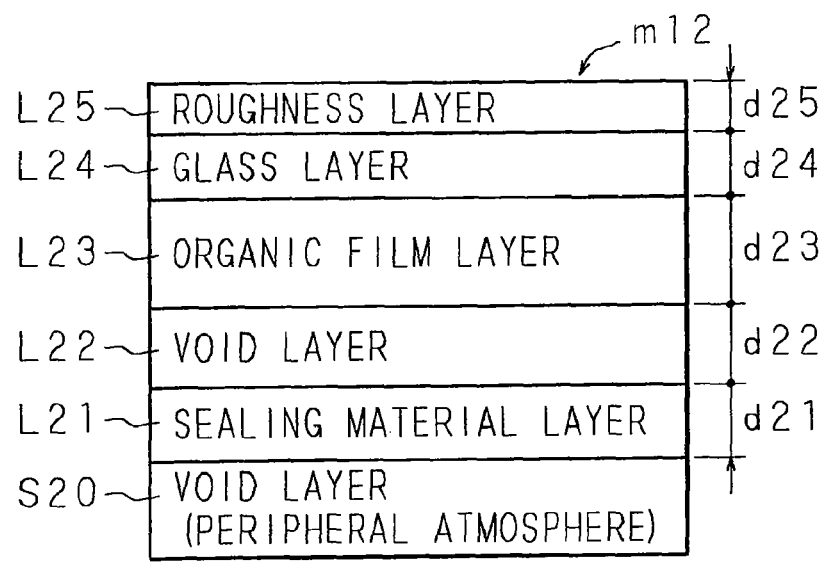

In the reflection manners of the 3 kinds as mentioned above, the layers through which the lights are transmitted are different from each other. Thus, as for the model to be used for the analysis, the model having the structure corresponding to the reflection manner in the actual measurement is required to be selected. FIGS. 32A to C are explanation views showing the model when it is measured from the side of the transparent substrate 51. FIG. 32A shows the model m10 of the structure corresponding to the reflected beam K1 in FIG. 31. The model m10, since corresponding to the reflection on the organic film 56, is configured such that the space 60 located below the organic film 56 is defined as the void layer (gap layer), and the organic film layer L1 (corresponding to the organic film 56), the glass layer L2 (corresponding to the portion without any surface roughness of the transparent substrate 51) and the roughness layer L3 (the portion corresponding to the surface roughness of the transparent substrate 51) are stacked on the void layer S1 (to be regarded as the substrate).

Also, FIG. 32B shows the model m11 of the structure corresponding to the reflected beam K2 in FIG. 31. The model m11, since corresponding to the reflection on the inner surface 57c of the cover material 57, is configured such that the material (sealing material) constituting the cover material 57 is regarded as the substrate, and the void layer L11 (corresponding to the gap layer of the space 60), the organic film layer L12 (corresponding to the organic film 56), the glass layer L13 (corresponding to the portion without any surface roughness of the transparent substrate 51) and the roughness layer L14 (the portion corresponding to the surface roughness of the transparent substrate 51) are stacked on its sealing material S10 (corresponding to the layer related to the cover material 57).

Moreover, FIG. 32C shows the model m12 of the structure corresponding to the reflected beam K3 in FIG. 31.

The model m12, since corresponding to the reflection on the boundary surface between the cover material 57 and the stage 4, is configured such that the medium (corresponding to the void layer in the space existing between the cover material 57 and the stage 4, in FIG. 31) constituting the peripheral atmosphere below the cover material 57 is regarded as the substrate, and the void layer L21 (corresponding to the layer of the material constituting the cover material 57), the void layer L22 (corresponding to the gap layer of the space 60), the organic film layer L23 (corresponding to the organic film 56), the glass layer L24 (corresponding to the portion without any surface roughness of the transparent substrate 51) and the roughness layer L25 (the portion corresponding to the surface roughness of the transparent substrate 51) are stacked on its void layer (peripheral atmosphere) S20 (substrate).

Note that in the foregoing respective models m10, m11 and m12, the organic film layers L1, L12 and L23 are simply represented as one film layer in which the respective film layers 52 to 55 shown in FIG. 30B are collected. However, the organic film layers L1, L12 and L23 in the actual modeling are assumed such that the hole transport layer 52, the emitting layer 53, the hole blocking layer 54 and the electron transport layer 55 are deposited similarly to the organic film 56 of the organic EL element panel 50, and the film thicknesses corresponding to the respective film layers 52 to 55 are set. In this way, the modeling corresponding to the respective film layers 52 to 55 enables the analysis of the characteristics of the respective film layers 52 to 55 included in the organic film 56. The user selects one model from the keyboard 13 or mouse 14 by considering the thickness of the organic EL element panel 50 and the like. Note that if the thickness dimension of the sample of the analysis target is 2.2 mm or more, the reflection direction of the reflected beam K3 is dislocated and deviated from the measurement range of the light obtainer 5. For this reason, if the thickness dimension of the sample is 2.2 mm or more, the reflected beam K3 cannot be measured by the light obtainer 5. Thus, as the structure of the model to be used for the analysis, the model m10 or the model m11 may be selected.

Also, if the thickness dimension of the sample is between 1.0 mm and 2.2 mm, there is the possibility that all of the reflected lights K1 to K3 belong to the measurement range of the light obtainer 5. For this reason, if the thickness dimension of the sample is between 1.0 mm and 2.2 mm, as the structure of the model to be used for the analysis, the model m10, m11 or m12 corresponding to the reflected lights K1 to K3 may be selected. Moreover, even if the thickness dimension of the sample is 1.0 mm or less, there is the possibility that all of the reflected lights K1 to K3 belong to the measurement range of the light obtainer 5. For this reason, the sample analyzing apparatus 1 may select the model m10, m11 or m12 corresponding to the reflected lights K1 to K3, as the structure of the model to be used for the analysis, if the thickness dimension of the sample is 1.0 mm or less.

Figure 33:
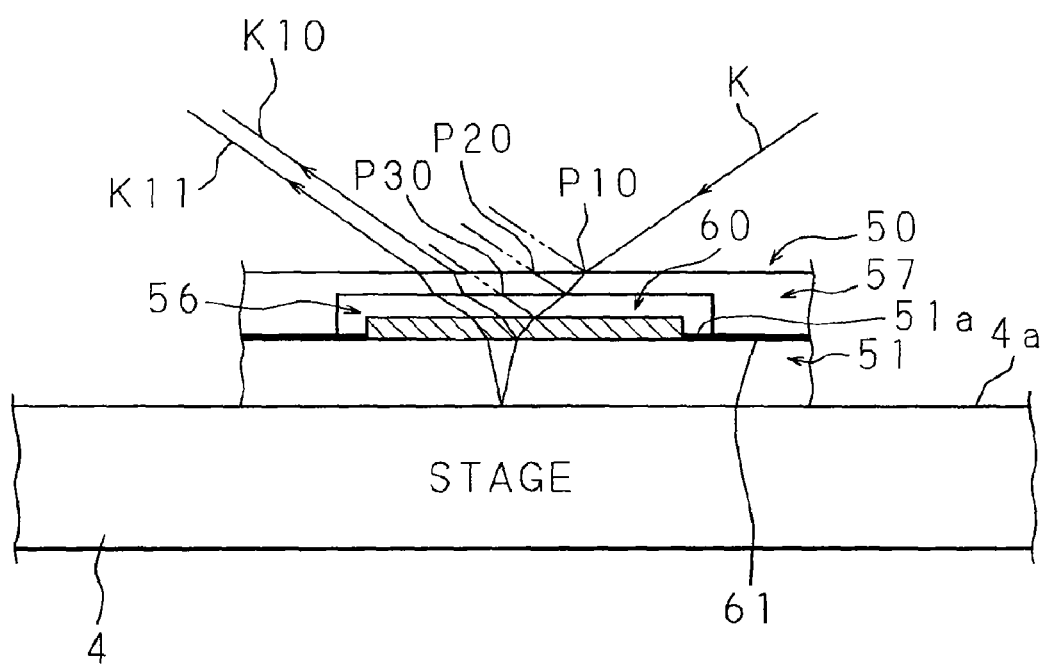
FIG. 33 is a diagrammatic sectional view showing input and reflection states of light when an organic EL element panel is measured from a transparent substrate side.

FIG. 33 is a diagrammatic sectional view showing the input and output states of the light when the organic EL element panel 50 is measured from the side of the transparent substrate 51. The organic EL element panel 50 is placed in the direction where the transparent substrate 51 is brought into contact with the stage 4 so that the light is irradiated from the side of the cover material 57. In the sample analyzing apparatus 1, the beam K of the polarization state is irradiated towards the cover material 57, and the beam K passed through the cover material 57 and the space 60 arrives at the organic film 56 composed of the plurality of film layers 52 to 55 (refer to FIG. 30B). Moreover, there is the case that after the beam K is passed through the organic film 56, it is reflected on the boundary between the organic film 56 and the transparent substrate 51 (the case of the reflected beam K10) and the case that it is passed through even the transparent substrate 51 and then reflected on the boundary between the transparent substrate 51 and the stage 4 (the case of the reflected beam K11). Note that any of the reflected lights K10, K11 is outputted from the cover material 57 and obtained by the light obtainer 5, and the polarization state is measured.

Note that even in FIG. 33, although the reflection (P10) on the cover glass surface, the reflection (P20) on the inner surface of the cover material 57, the reflection (P30) on the surface of the organic film 56 and the multiple reflection are actually included, those reflections (P10, P20 and P30) are not directly used to select the model to be used in the analysis. Thus, their treatments are omitted.

When the sample is analyzed in the placement manner of the organic EL element panel 50 shown in FIG. 13, the model to be used for the analysis is required to use the structure corresponding to the reflected lights K10, K11. FIGS. 34A and B show the model at the time of the measurement from the side of the cover material 57. FIG. 34A shows the model m20 of the structure corresponding to the reflected beam K10. The model m20 has the structure where the lowermost transparent substrate 51 is defined as the glass layer (S30), and the organic film layer L31 (corresponding to the organic film 56), the void layer L32 (corresponding to the space 60), the sealing material layer L33 (corresponding to the portion without any surface roughness of the cover material 57) and the roughness layer L34 (the portion corresponding to the surface roughness of the cover material 57) are stacked thereon. Note that the thicknesses d31 to d34 of the respective layers of the model m20 are set in accordance with the value inputted by the user in the preparation stage.

On the other hand, FIG. 34B shows the model m21 of the structure corresponding to the reflected beam K11. In the model m21, the medium (corresponding to the void layer of the space existing between the transparent substrate 51 and the stage 4 in FIG. 33) constituting the peripheral atmosphere below the transparent substrate 51 is regarded as the substrate. The glass layer L41 (corresponding to the transparent substrate 51), the organic film layer L42 (corresponding to the organic film 56), the void layer L43 (corresponding to the space 60), the sealing material layer L44 (corresponding to the portion without any surface roughness of the cover material 57) and the roughness layer L45 (the portion corresponding to the surface roughness of the cover glass 57) are stacked on its void layer S40 (substrate). Note that the thicknesses d41 to d45 of the respective layers of the model m21 are set in accordance with the value inputted by the user in the preparation stage. The user selects the model to be selected from the keyboard 13 or mouse 14.

Figure 35:
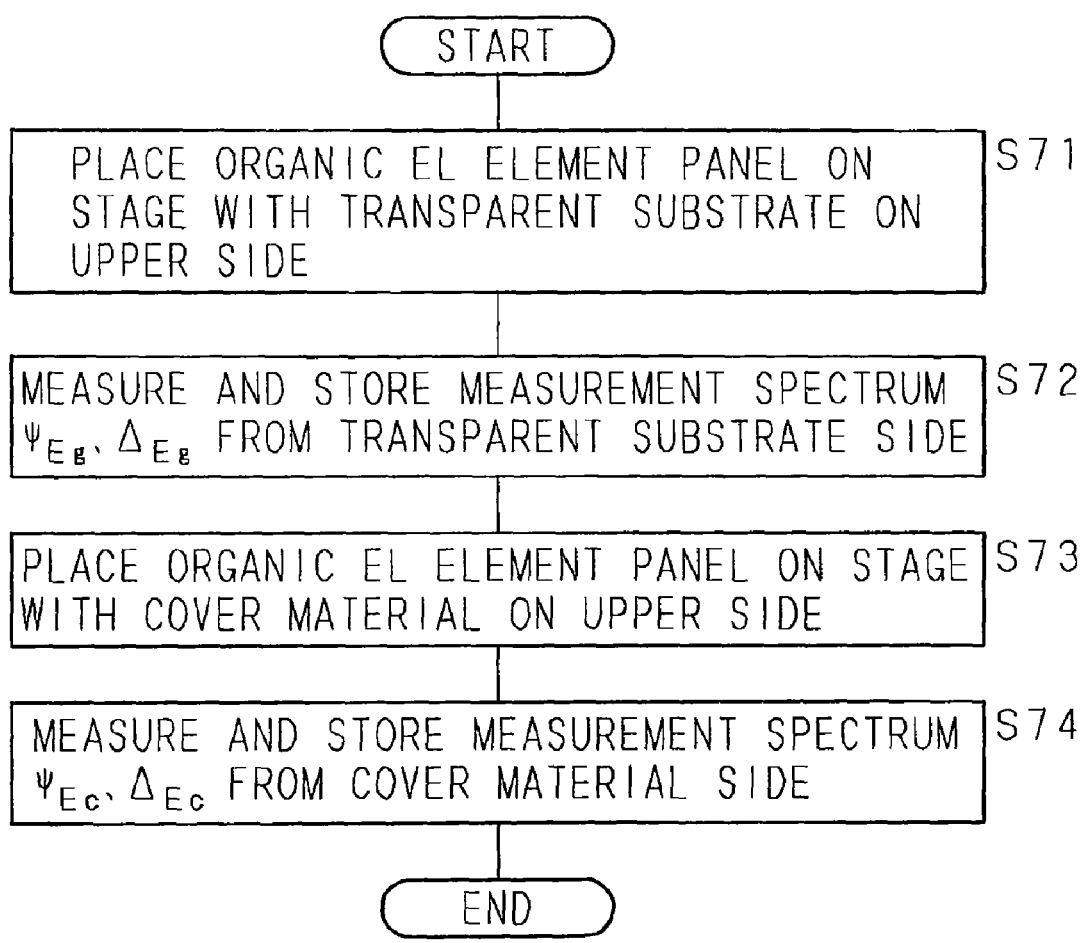
FIG. 35 is a flowchart showing a measurement procedure of an organic EL element panel.

FIG. 35 is a flowchart showing the measurement procedure of the organic EL element panel 50. At first, the organic EL element panel 50 is placed on the stage 4 while the transparent substrate 51 is placed on the upper side (Step S71). In the sample analyzing apparatus 1, the light irradiator 3 and the light obtainer 5 are used, and as shown in FIG. 31, the light is irradiated towards the transparent substrate 51. Then, the measurement spectra $\Psi_{Eg}$, $\Delta_{Eg}$ on the side of the transparent substrate 51 are measured, and the measurement result is received by the computer 10 and stored in the storage unit 11b (Step S72). Next, in order to carry out the measurement from the side of the cover material 57, while the organic EL element panel 50 is placed in the opposite direction, namely, while the cover material 57 is placed on the upper side, the organic EL element panel 50 is placed on the stage 4 (Step S73).

The work for orienting the organic EL element panel 50 in the opposite direction may be manually executed by the user. Also, with a feeding robot (not shown), it is allowable to hold the organic EL element panel 50, invert this and place on the stage 4. In the sample analyzing apparatus 1, the light irradiator 3 and the light obtainer 5 are used, and as shown in FIG. 33, the light is irradiated onto the cover material 57, and the measurement spectra $\Psi_{Ec}$, $\Delta_{Ec}$ on the side of the cover material 57 are measured, and the measurement result is received by the computer 10 and stored in the storage unit 11b (Step S74). Note that in this embodiment, the side of the transparent substrate 51 is measured first. However, the side of the cover material 57 may be first measured.

Figure 36:
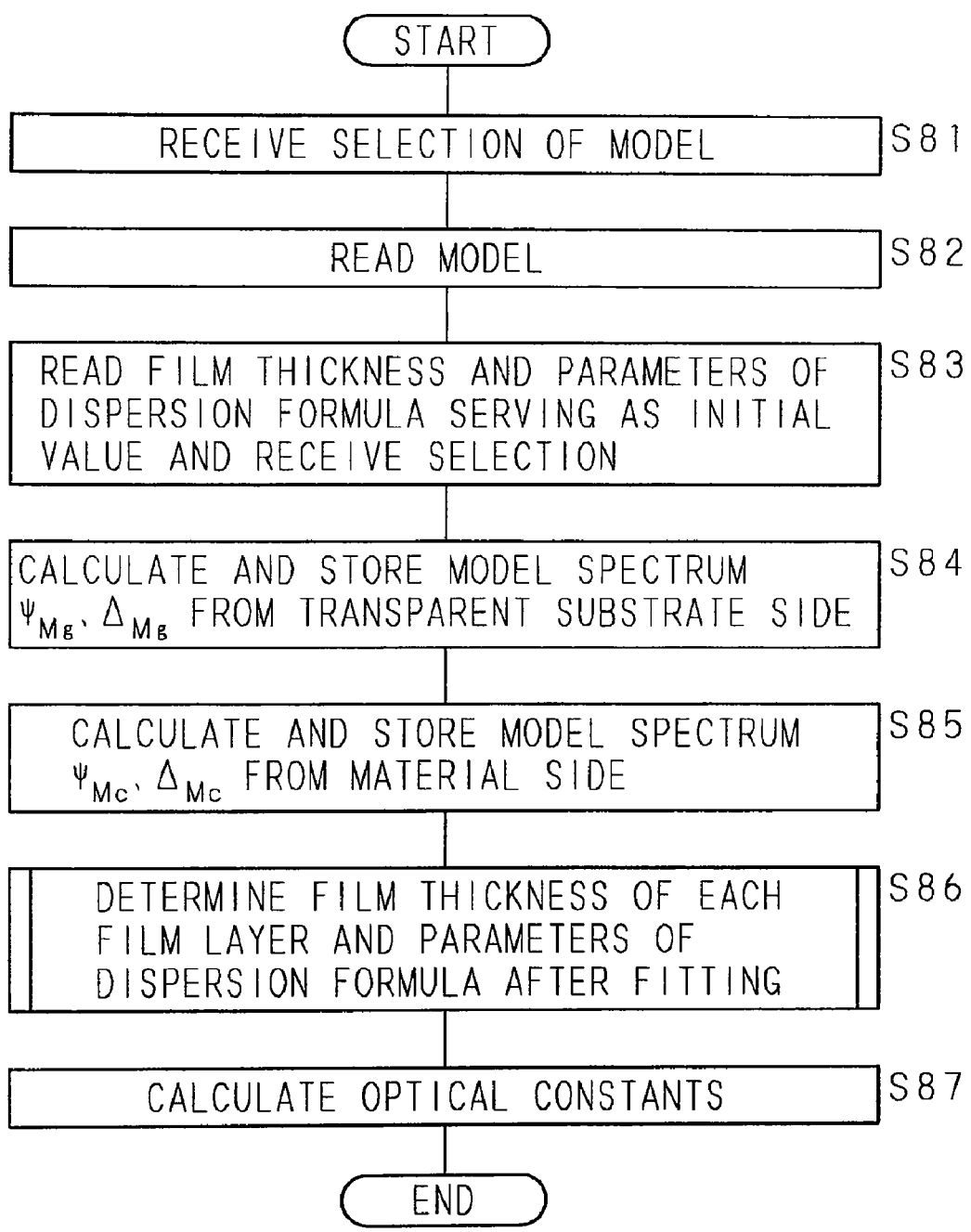
FIG. 36 is a flowchart showing a procedure of a calculation process of a film thickness and an optical constant.

FIG. 36 is a flowchart showing the procedure of the calculation process of the film thickness and the optical constant.

At first, a CPU 11a of the sample analyzing apparatus 1 receives the selection of the model from the keyboard 13 or mouse 14 (Step S81). In this model selection, as the model on the side of the transparent substrate 51, the model is selected from the models m10 to m12 shown in FIGS. 32A to C, and as the model on the side of the cover material 57, the model is selected from the model m20 or m21 shown in FIGS. 34A and B. In this model selection, the proper model may be selected in accordance with the film thickness of the organic EL element panel 50 and the like. Note that this embodiment is explained under an assumption where the model m11 shown in FIG. 32B is selected as the model on the side of the transparent substrate 51, and the model m20 shown in FIG. 34A is selected as the model on the side of the cover material 57, respectively.

The CPU 11a reads the selected model from the storage unit 11b (Step S82). Then, the CPU 11a corresponds to the selected models m11, m12 and reads the plurality of film thicknesses and the parameters of the plurality of dispersion formulas, which are stored in advance and serve as initial values, from the storage unit 11b and receives the selection of each model from the keyboard 13 or mouse 14 (Step S83) and then determines each model. The CPU 11a calculates the model spectra $\Psi_{mg}$, $\Delta_{Mg}$ on the side of the transparent substrate 51 in accordance with the read model and stores the result in the storage unit 11b (Step S84). Similarly, the CPU 11a calculates the model spectra $\psi_{Mc}$, $\Delta_{Mc}$ on the side of the cover material 57 and stores the result in the storage unit 11b (Step S85).

The CPU 11a reads the model spectra $\Psi_{Mg}$, $\Delta_{Mg}$ on the side of the transparent substrate 51 calculated at the step S84, the model spectra $\Psi_{Mc}$, $\Delta_{Mc}$ on the side of the cover material 57 calculated at the step S85, the measurement spectra $\Psi_{Eg}$, $\Delta_{Eg}$ on the side of the transparent substrate 51 measured at the step S72 and the measurement spectra $\Psi_{Ec}$, $\Delta_{Ec}$ on the side of the cover material 57 measured at the step S74, respectively, and performs the fitting thereon and then determines the film thicknesses of the respective film layers 52 to 55 of the organic film 56 and the parameters of the dispersion formula (Step S86). Note that the detailed process of this step will be described later. Finally, the CPU 11a refers to the film thicknesses of the respective film layers 52 to 55, the parameters of the dispersion formula, the voids and the like and consequently calculates the optical constants (the refractive index n and the extinction coefficient k) of the respective film layers 52 to 55 of the organic film 56 in the organic EL element panel 50 (Step S87).

Figure 37B:
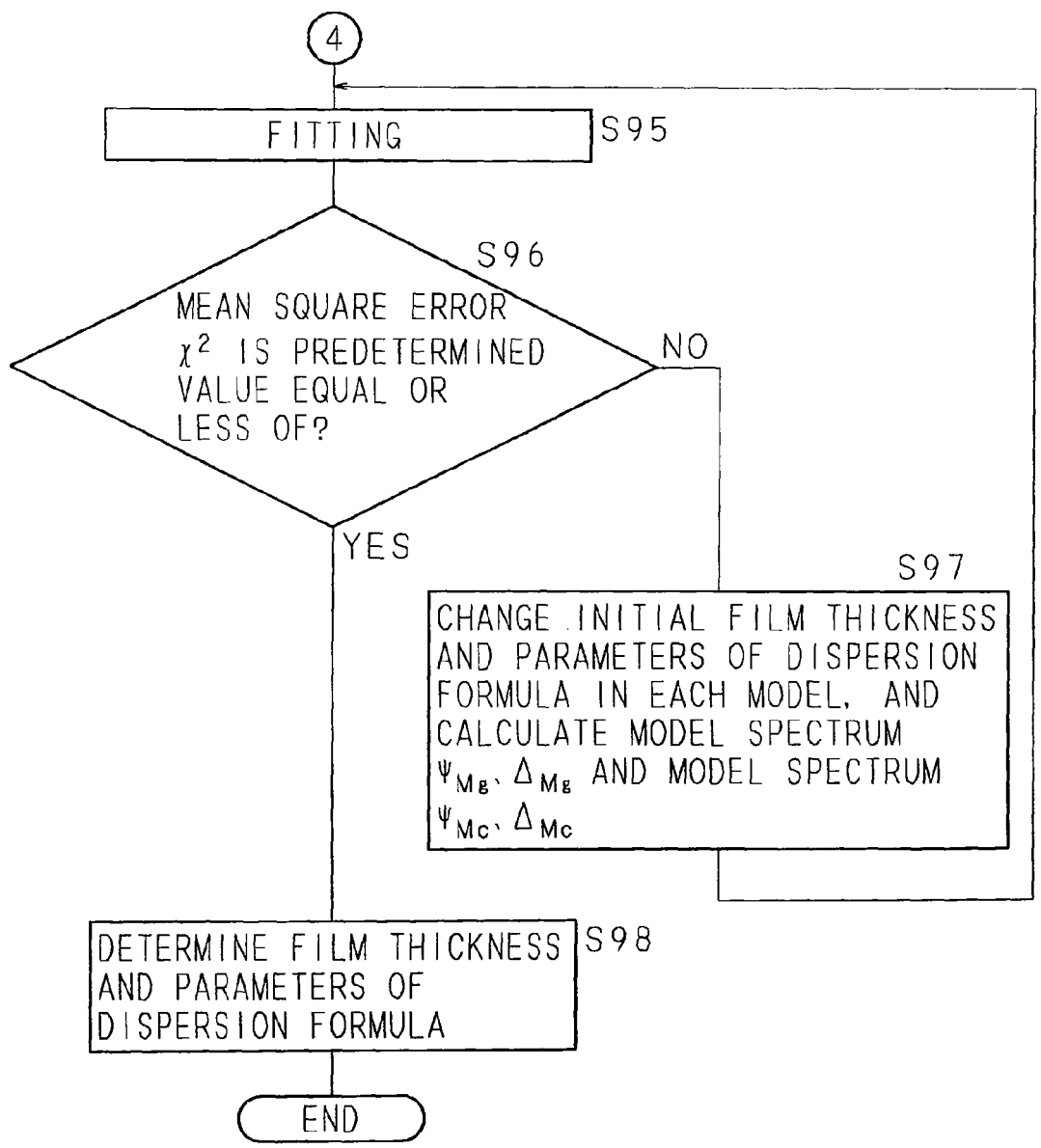
FIGS. 37A and B are flowcharts showing a procedure of a fitting process.

FIGS. 37A and B are flowcharts showing the procedure of the fitting process. The CPU 11a reads the measurement spectra $\Psi_{Eg}$, $\Delta_{Eg}$ on the side of the transparent substrate 51 measured at the step S72 from the storage unit 11b (Step S91). Also, the CPU 11a reads the model spectra $\Psi_{Mg}$, $\Delta_{Mg}$ on the side of the transparent substrate 51 calculated at the step S84 from the storage unit 11b (Step S92). Similarly, even on the side of the cover material 57, the CPU 11a reads the measurement spectra $\Psi_{Ec}$, $\Delta_{Ec}$ on the side of the cover material 57 measured at the step S74 from the storage unit 11b (Step S93) and also reads the model spectra $\Psi_{MC}$, $\Delta_{Mc}$ on the side of the cover material 57 calculated at the step S85 from the storage unit 11b (Step S94).

The CPU 11a carries out the process (fitting) for comparing the measurement spectra $\Psi_{Eg}$, $\Delta_{Eg}$ on the side of the transparent substrate 51 and the model spectra $\Psi_{Mg}$, $\Delta_{Mg}$ and the measurement spectra $\Psi_{Ec}$, $\Delta_{Ec}$ on the side of the cover material 57 and the model spectra $\Psi_{Mc}$, $\Delta_{Mc}$, which are read for the fitting, and changing the film thicknesses and the parameters of the dispersion formula and the like so as to minimize the difference between the measurement spectra and the model spectra (Step S95). The CPU 11a uses the least squares method as this fitting result and obtains the mean square error $\chi^2$. The mean square error $\chi^2$ at the step S95 can be calculated by the equation (19).

$$\chi^2 = \frac{1}{2T_g - P_g} \sum_{i=1}^{T_g} (\text{Exp}_i - \text{Mod}_i)^2 / \sigma_i^2 + \frac{1}{2T_c - P_c} \sum_{i=1}^{T_c} (\text{Exp}_i - \text{Mod}_i)^2 / \sigma_i^2 \qquad (19)$$

When the organic EL element panel 50 is measured from the side of the transparent substrate 51, let us suppose that Tg measurement data pairs are Exp (i=1, 2 ..., Tg) and Tg model calculation data pairs are Mod (i=1, 2 ..., Tg). At the time of the measurement from the side of the cover material 57, let us suppose that Tc measurement data pairs are Exp (i=1, 2 ..., Tc) and Tc model calculation data pairs are Mod (i=1, 2 ..., Tc). Also, Pg is the numeral of the parameters at the time of the measurement from the side of the transparent substrate 51, and Pc is the numeral of the parameters at the time of the measurement from the side of the cover material 57.

As the result of the fitting, the CPU 11a judges whether or not the calculated mean square error $\chi^2$ is a predetermined value or less (Step S96). Note that this predetermined value is stored in the storage unit 11b.

The CPU 11a, if judging that the calculated mean square error $\chi^2$ is not the predetermined value or less (Step S96: NO), properly changes the film thickness and the parameters of the dispersion formula, which are set as the initial values for each model, and again calculates the model spectra $\Psi_{Mg}, \Delta_{Mg}$ and the model spectra $\Psi_{Mc}, \Delta_{Mc}$ (Step S97). Note that this change may be the change down by the CPU 11a or may be the change done by an operator. After that, the operational flow again proceeds to the step S95, and the similar processes are repeated. Note that this explain is explained such that the initial film thicknesses of the models on the side of the transparent substrate 51 and the side of the cover material 57 and the parameters of the dispersion formula are changed to then calculate the model spectra $\Psi_{Mg}, \Delta_{Mg}$ and the model spectra $\Psi_{Mc}, \Delta_{Mc}$. However, the models themselves which are applied on the side of the transparent substrate 51 and the side of the cover material 57 may be changed. For example, the model of FIG. 32B is used as the model on the side of the transparent substrate 51, and the model of FIG. 34A is used as the model on the side of the cover material 57. In addition, it is allowable to read the models different from them (for example, the models in FIG. 32C and FIG. 34B) from the storage unit 11b and change the initial film thicknesses of those different models and the parameters of the dispersion formula and then calculate the model spectra $\psi_{Mg}, \Delta_{Mg}$ and the model spectra $\Psi_{Mc}, \Delta_{Mc}$. Note that this change may be the change down by the CPU 11a or may be the change done by the operator. As the other models, for example, there is the model in which the roughness layer of the film thickness d further exists between the organic film layer L12 of FIG. 32B and the void layer L11 and the model in which the roughness layer of the film thickness d further exists between the void layer L32 of FIG. 34A and the organic film layer L31. The model to calculate the model spectrum for the different model is stored in the storage unit 11b. Then, the CPU 11a newly reads this model and calculates the model spectra $\Psi_{Mg}, \Delta_{Mg}$ and the model spectra $\Psi_{Mc}, \Delta_{Mc}$. Note that this change may be the change down by the CPU 11a or may be the change done by the operator.

The sample analyzing apparatus 1, if judging that the calculated mean square error $\chi^2$ is the predetermined value or less (Step S96: YES), determines the film thickness and the parameters of the dispersion formula, which are obtained in the fitting at that time, as the values to be employed (Step S98). Note that in the process at the step S96, the process is carried out until the calculated mean square error $\chi^2$ becomes the predetermined value or less. However, the initial film thickness and the parameters of the dispersion formula which should be set for each model within a predetermined time may be sequentially changed to employ as the result the film thickness and the parameters of the dispersion formula when the minimal mean square error is obtained within the predetermined time. Also, it is allowable to sequentially change the incident angle φ and the reflection angle φ and determine the film thickness and the parameters of the dispersion formula when the mean square error is minimal as the values to be employed. For example, at an incident angle $\phi_1$ and reflection angle $\phi_1$, in the predetermined time, the film thickness of each model and the parameters of the dispersion formula are changed to calculate a minimal mean square error $\chi_1$. After that, the incident angle is physically changed to $\phi_2$, and the reflection angle is physically changed to $\phi_2$, and in the predetermined time, the film thickness of each model and the parameters of the dispersion formula are changed to calculate a minimal mean square error $\chi^2_2$. Moreover, after that, the incident angle is physically changed to $\phi_3$, and the reflection angle is physically changed to $\phi_3$, and in the predetermined time, the film thickness of each model and the parameters of the dispersion formula are changed to calculate a minimal mean square error $\chi^2_3$. The sample analyzing apparatus 1 compares the incident angle $\phi_1$, the incident angle $\phi_2$ and the incident angle $\phi_3$ (the reflection angle $\phi_1$, the reflection angle $\phi_2$ and the reflection incident angle $\phi_3$) and the respective mean square error $\chi^2_1$, mean square error $\chi^2_2$ and mean square error $\chi^2_3$, respectively, and employs the film thickness and the parameters of the dispersion formula at the incident angle when the minimal mean square error is obtained, as the result. Note that in addition to the method of physically changing the incident angle and the output angle, the values may be properly changed while the incident angle and the output angle are kept constant. Also, the incident angle itself can be considered to be one parameter of the fitting.

Eighth Embodiment

Figure 38:
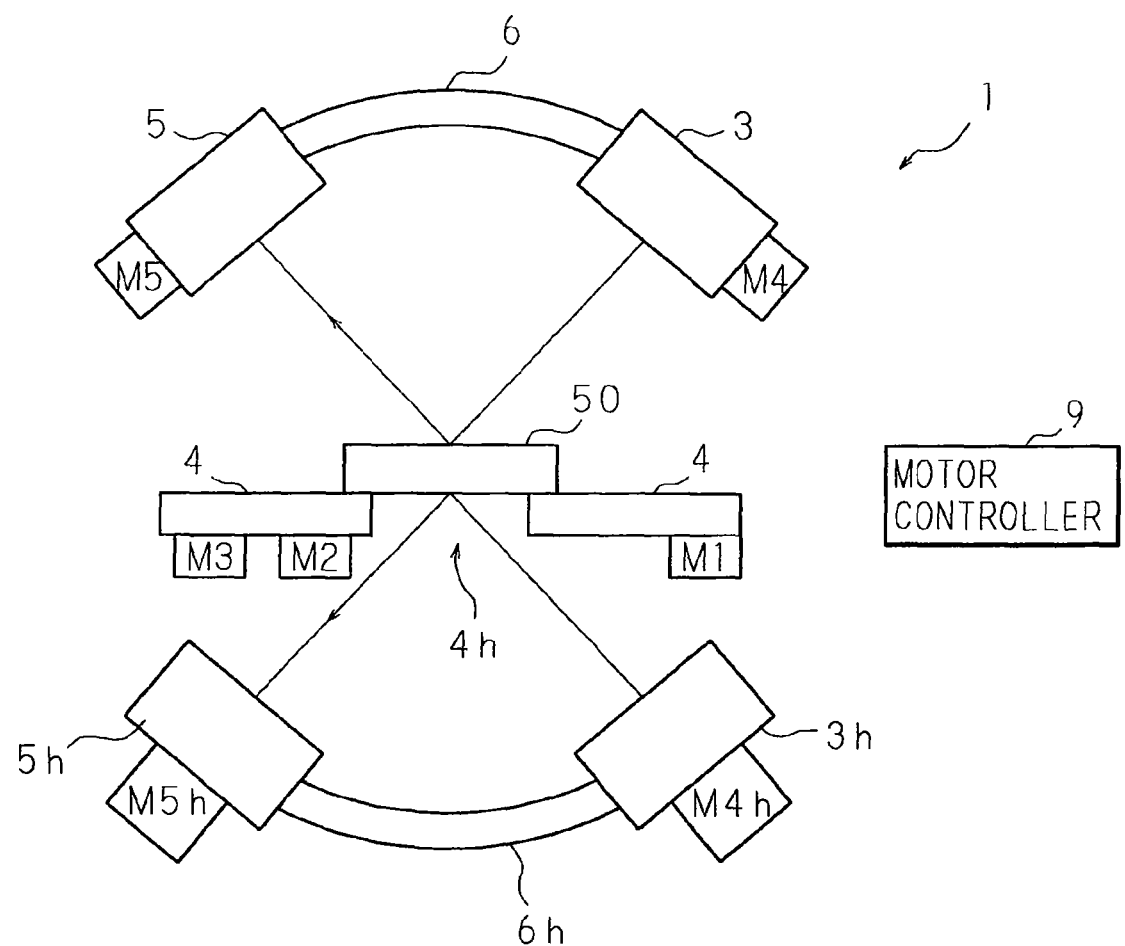
FIG. 38 is a block diagram showing a main portion of a measuring unit of a sample analyzing apparatus according to an eighth embodiment.

FIG. 38 is a block diagram showing the main portion of the measuring unit in the sample analyzing apparatus 1 according to the eighth embodiment. As shown in FIG. 38, in order to enable even the measurement from the lower direction, a route hole 4h that has a round shape when it is viewed from the bottom or has a rectangular opening penetrates the stage 4. The organic EL element panel 50 is placed on the stage 4 in the situation that it straddles this route hole 4h. Above the stage 4, as explained in the seventh embodiment, the light irradiator 3 and the light obtainer 5 which serve as the measuring unit are movably placed on the rail 6 having the shape of a half circular arc, in order to make them function as a substrate side measurement device or a cover side measurement side.

Similarly, even below the stage 4, a light irradiator 3h and an light obtainer 5h which serve as the measuring unit are placed (be possible to move) on a rail 6h having a shape of a half circular arc, in order to make them function as the cover side measurement device or the substrate side measurement side, at the position symmetrical about the stage 4. A motor M4h is attached to the light irradiator 3h, and a motor 5Mh is attached to the light obtainer 5h, respectively, and they are moved on the rail 6h in accordance with the control of the motor controller 9. Note that the illustration of the transmission line between the motor controller 9 and each motor is omitted. Also, the light irradiator 3, the light obtainer 5, the light irradiator 3h and the light obtainer 5h may be the fixed type that cannot be moved on the rail 6 and the rail 6h. Under such configuration, when the organic EL element panel 50 is placed on the stage 4 while the transparent substrate 51 is placed on the upper side as shown in FIG. 31, the data with regard to the side of the transparent substrate 51 can be obtained from the light obtainer 5, and the data with regard to the side of the cover material 57 can be obtained from the light obtainer 5h on the lower side of the stage 4.

On the contrary, when the organic EL element panel 50 is placed on the stage 4 while the cover material 57 is placed on the upper side as shown in FIG. 33, the data with regard to the side of the cover material 57 can be obtained from the light obtainer 5, and the data with regard to the side of the transparent substrate 51 can be obtained from the light obtainer 5h below the stage 4. Note that the xenon lamp 2 and the spectrometer 7 which are not shown are installed correspondingly to the light irradiator 3h and the light obtainer 5h, respectively.

Figure 39A:
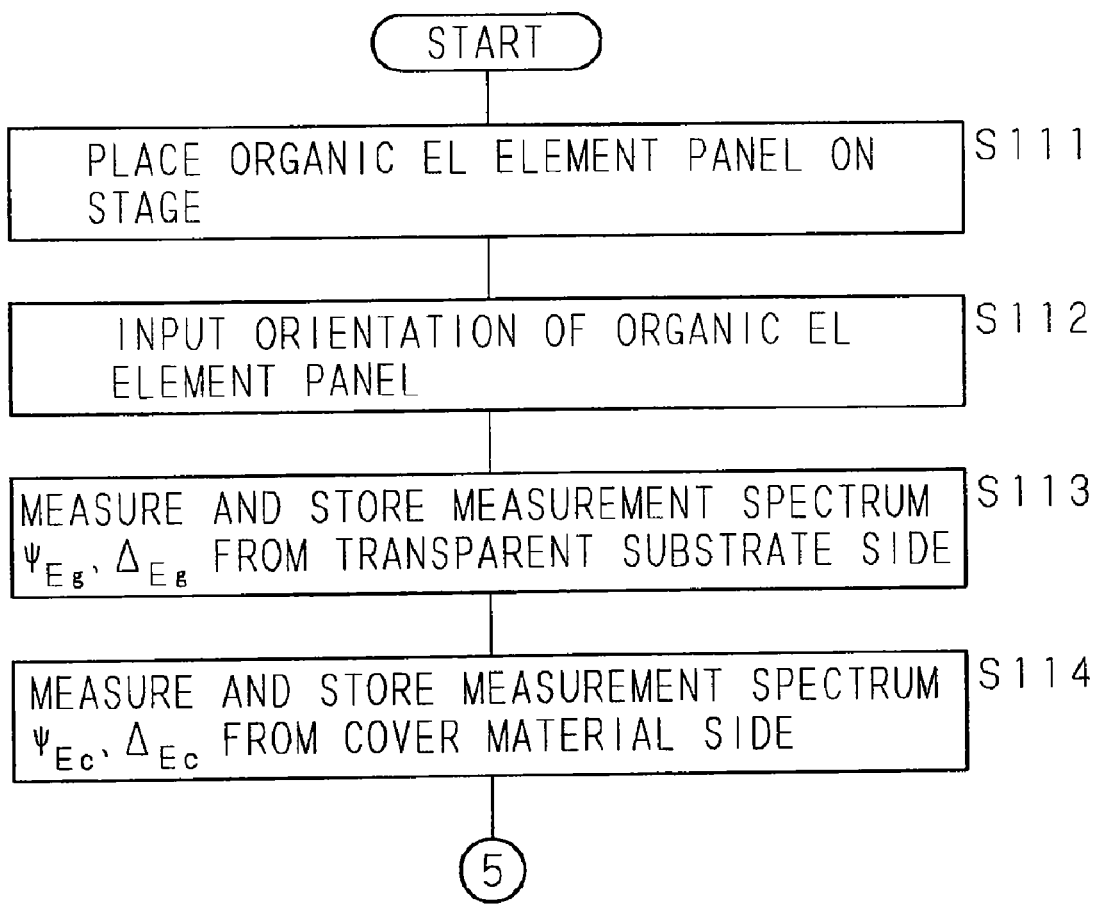
FIGS. 39A and B are flowcharts showing a procedure of a calculation process of a film thickness and an optical constant according to a ninth embodiment.
Figure 39B:
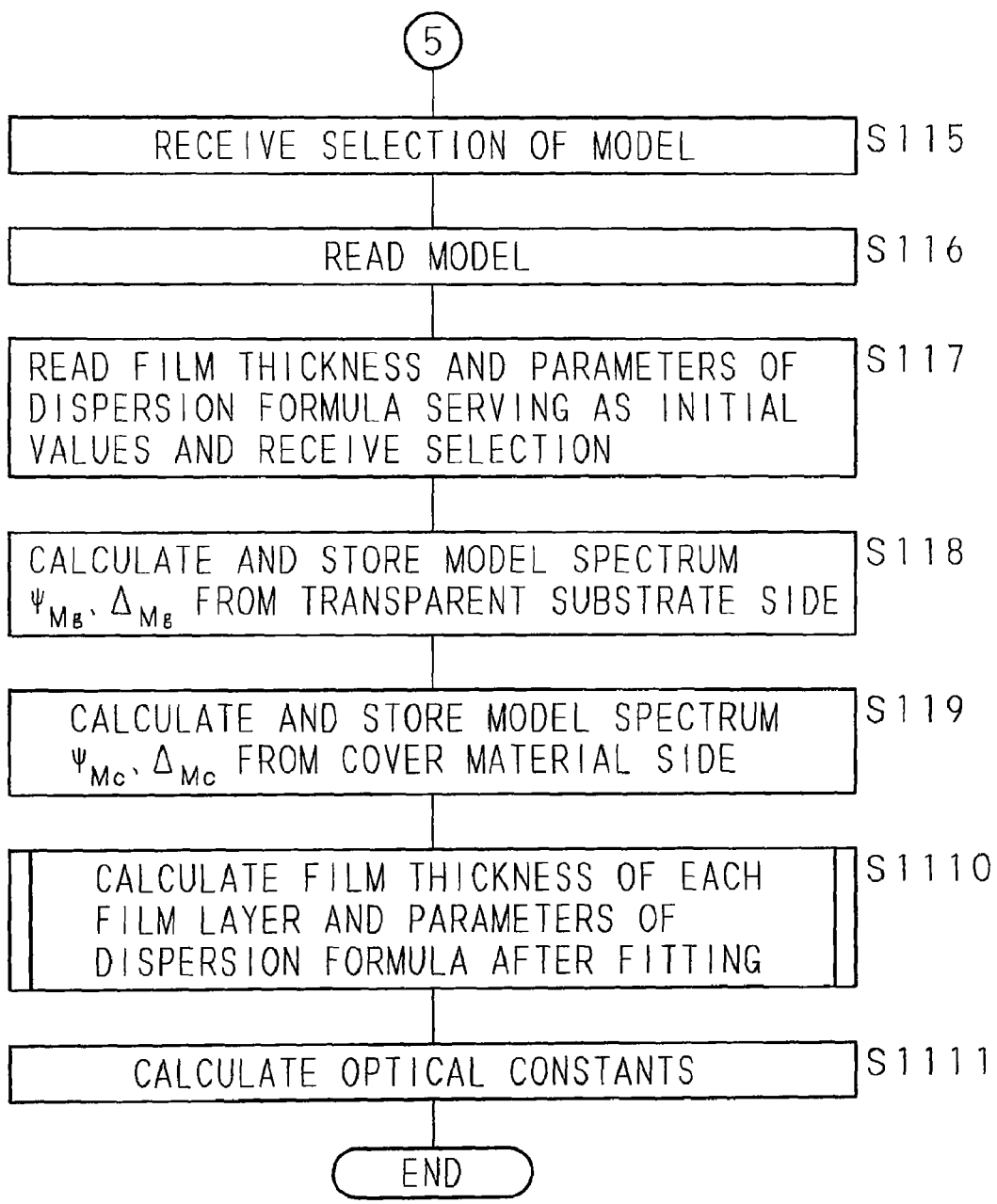

FIGS. 39A and B are flowcharts showing the procedure of the calculation process of the film thickness and the optical constant according to the eighth embodiment. At first, the organic EL element panel 50 is placed on the stage 4 (Step S111). The user inputs the orientation of the organic EL element panel 50 from the keyboard 13 or mouse 14 (Step S112). That is, the information as to whether the transparent substrate 51 is placed on the upper side as shown in FIG. 31 or the cover material 57 is placed on the upper side as shown in FIG. 33 is inputted. The case of the example of FIG. 31, namely, the case that the transparent substrate 51 is placed on the upper side will be explained.

The sample analyzing apparatus 1 uses the light irradiator 3 and the light obtainer 5, irradiates the light towards the transparent substrate 51 and measures the measurement spectra $\Psi_{Eg}, \Delta_{Eg}$ on the side of the transparent substrate 51 and then stores the measurement result in the storage unit 11b (Step S113). Next, in order to carry out the measurement from the side of the cover material 57, the sample analyzing apparatus 1 uses the light irradiator 3h and the light obtainer 5h and irradiates the light from below the stage 4 through the route hole 4h towards the cover material 57 and measures the measurement spectra $\Psi_{Ec}, \Delta_{Ec}$ on the side of the cover material 57 and then stores the measurement result in the storage unit 11b (Step S114).

Then, the CPU 11a receives the selection of the model from the keyboard 13 or mouse 14 (Step S115). The CPU 11a reads the selected model from the storage unit 11b (Step S116). The CPU 11a reads the plurality of film thicknesses and the parameters of a plurality of the dispersion formulas, which serve as the pre-stored initial values, correspondingly to the selected models m11, m12, and receives the selections of the respective models from the keyboard 13 or mouse 14 and determines the respective models. The CPU 11a calculates the model spectra $\Psi_{Mg}, \Delta_{Mg}$ on the side of the transparent substrate 51 in accordance with the read model and stores the result in the storage unit 11b (Step S118). Similarly, the CPU 11a calculates the model spectra $\Psi_{Mc}, \Delta_{Mc}$ on the side of the cover material 57 and stores the result in the storage unit 11b (Step S119).

The sample analyzing apparatus 1 reads the model spectra $\Psi_{Mg}, \Delta_{Mg}$ on the side of the transparent substrate 51 calculated at the step S118, the model spectra $\Psi_{Mc}, \Delta_{Mc}$ on the side of the cover material 57 calculated at the step S119, the measurement spectra $\Psi_{Eg}, \Delta_{Eg}$ on the side of the transparent substrate 51 measured at the step S113 and the measurement spectra $\Psi_{Ec}, \Delta_{Ec}$ on the side of the cover material 57 measured at the step S114, respectively, and performs the fitting thereon and then calculates the film thicknesses of the respective film layers 52 to 55 of the organic film 56 and the parameters of the dispersion formula (Step S1110). Finally, the sample analyzing apparatus 1 refers to the film thicknesses of the respective film layers 52 to 55, the parameters of the dispersion formula, the voids and the like, and consequently calculates the optical constants (the refractive indexes n and the extinction coefficients k) of the respective film layers 52 to 55 of the organic film 56 in the organic EL element panel 50 (Step S1111).

This eighth embodiment has the foregoing configuration, and the other configurations and actions are similar to the seventh embodiment. Thus, the same reference numbers are assigned to the corresponding portions, and their detailed explanations are omitted.

Ninth Embodiment

Figure 40:
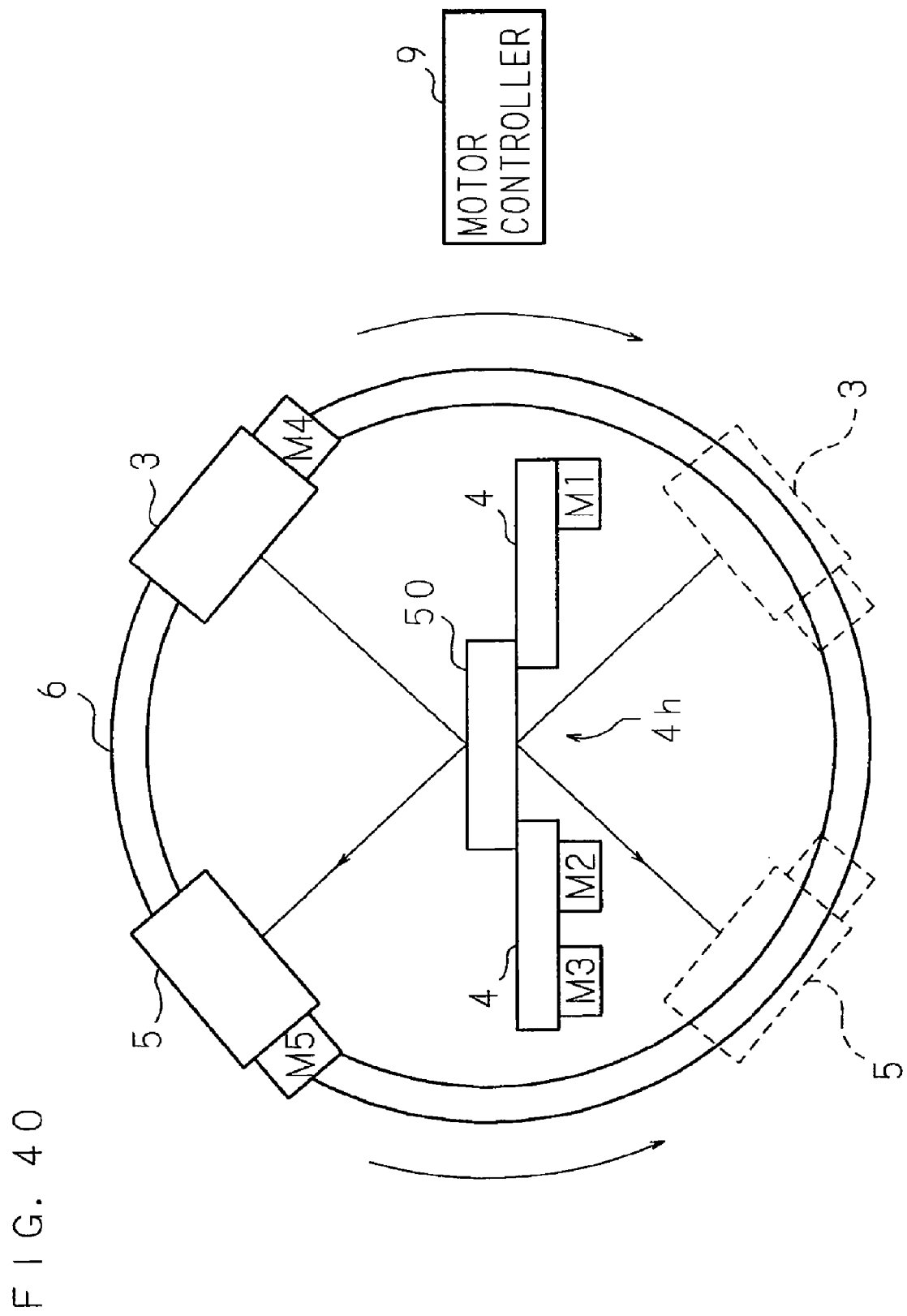
FIG. 40 is a block diagram showing a main portion of a measuring unit of a sample analyzing apparatus according to a tenth embodiment.

FIG. 40 is a block diagram showing the main portion of the measuring unit in the sample analyzing apparatus 1 according to the ninth embodiment. Differently from the eighth embodiment, in the sample analyzing apparatus 1 in the ninth embodiment, the single light irradiator 3 and light obtainer 5 are installed, and they are moved to the upper side and lower side of the stage 4. The annular rail 6 is circumferentially laid around the stage 4. The light irradiator 3 is moved clockwise along the rail 6, and the light obtainer 5 is moved counterclockwise along the rail 6. The motors M4 and M5 are attached to the light irradiator 3 and the light obtainer 5, which are moved on the rail 6 in accordance with the indication of the motor controller 9. The motor controller 9, the rail 6, the motor M4 and the motor M5 constitute the moving device (moving apparatus).

When the measurement is executed on the upper side of the stage 4, the motor controller 9 moves the light irradiator 3 serving as the measuring unit to a position of 2 o'clock indicated by the solid line in the drawing, in order to make it function as the substrate side measuring device or cover side measuring device. Also, this moves the light obtainer 5 serving as the measuring unit to a position of 10 o'clock indicated by the solid line in the drawing, in order to make it function as the substrate side measuring device or cover side measuring device. On the other hand, after the completion of the measurement on the upper side, the motor controller 9 moves the light irradiator 3 serving as the measuring unit to a position of 4 o'clock indicated by the dashed line in the drawing, in order to make it function as the cover side measuring device or substrate side measuring device. Also, this moves the light obtainer 5 serving as the measuring unit to a position of 8 o'clock indicated by the dashed line in the drawing, in order to make it function as the cover side measuring device or substrate side measuring device. Consequently, one set of the light irradiator 3 and the light obtainer 5 can execute the measurements on the side of the transparent substrate 51 and the side of the cover material 57. Thus, the cost-down can be attained. Note that although this embodiment uses the annular rail 6, at least the rail 6 may exist in the range where the light irradiator 3 at the position of 2 o'clock indicated by the solid line can be moved to the position of 4 o'clock indicated by the dashed line and in the range where the light obtainer 5 at the position of 10 o'clock indicated by the solid line can be moved to the position of 8 o'clock indicated by the dashed line.

This ninth embodiment has the foregoing configuration, and the other configurations and actions are similar to the seventh and eighth embodiments. Thus, the same reference numbers are assigned to the corresponding portions, and their detailed explanations are omitted.

Tenth Embodiment

FIG. 4 is a block diagram showing the configuration of the sample analyzing apparatus 1 according to the tenth embodiment. The computer program for operating the computer 10 in the sample analyzing apparatus 1 according to the seventh embodiment can be provided in a portable recording medium 1A such as CD-ROM, a memory card and the like, as described in this tenth embodiment. Moreover, the computer program can be downloaded through a communication network, such as LAN, the Internet and the like which are not shown, from a server computer (not shown). Its content will be explained below.

A portable recording medium 1A in which the computer program for instructing a recording medium reading apparatus (not shown) in the computer 10 shown in FIG. 41 to receive the result of the substrate side, receive the result of the cover side, calculate the polarization state and analyze the characteristics recorded is inserted, and this program is installed into a program of the storage unit 11b. Or, such a program may be downloaded from an external server computer (not shown) through a communication unit (not shown) and installed in the storage unit 11b. Such a program is loaded to the RAM 11c and executed. Consequently, this functions as the computer 10 of the present invention as mentioned above.

This tenth embodiment has the foregoing configuration, and the other configurations and actions are similar to the seventh to ninth embodiments. Thus, the same reference numbers are assigned to the corresponding portions, and their detailed explanations are omitted.

Eleventh Embodiment

The eleventh embodiment is related to the method that calculates the mean square error which becomes a predetermined value or less or a minimal value by using a plurality of dispersion formulas. For the model on the side of the transparent substrate 51 and the model on the side of the cover material 57, a different known dispersion formula other than the dispersion formula indicated by the equation (16) can be used. For example, in the dispersion formula proposed by G. E. Jellison, Jr., F. A. Modine, P. Doshi, A. Rohatgi et al., in "Spectroscopic ellipsometry characterization of thin-film silicon nitride" (Thin Solid Films 313-314 (1998) p 193-p 197), its imaginary part is represented by the equation (20), and its real part is represented by the equation (21), respectively.

$$\varepsilon_{2TL} = \frac{AE_o C(E-E_g)^2}{(E^2-E_o^2)^2+C^2E^2} \frac{1}{E} = 0 \quad E > E_g \quad E \le E_g \quad (20)$$

$$\varepsilon_{1TL}(E) = \varepsilon_1(\infty) + \frac{2}{\pi} P \int_{E_g}^{\infty} \frac{\xi \varepsilon_{2TL}(\xi)}{\xi^2 - E^2} d\xi \quad (21)$$

Here, $E_o$ is a peak transition energy, C is an broadening term, $E_g$ is an optical band edge, and A is a proportional item of a transition probability matrix element. Also, $\varepsilon_1(\infty)$ is an integration constant, and 1 is typically given. A plurality of kinds of dispersion formulas, such as the equation (19), the equation (20) and the equation (21) and the like are stored in the storage unit 11b shown in FIG. 29. The CPU 11a properly reads them and calculates the mean square error that becomes the predetermined value or less or the minimal value.

Figure 42A:
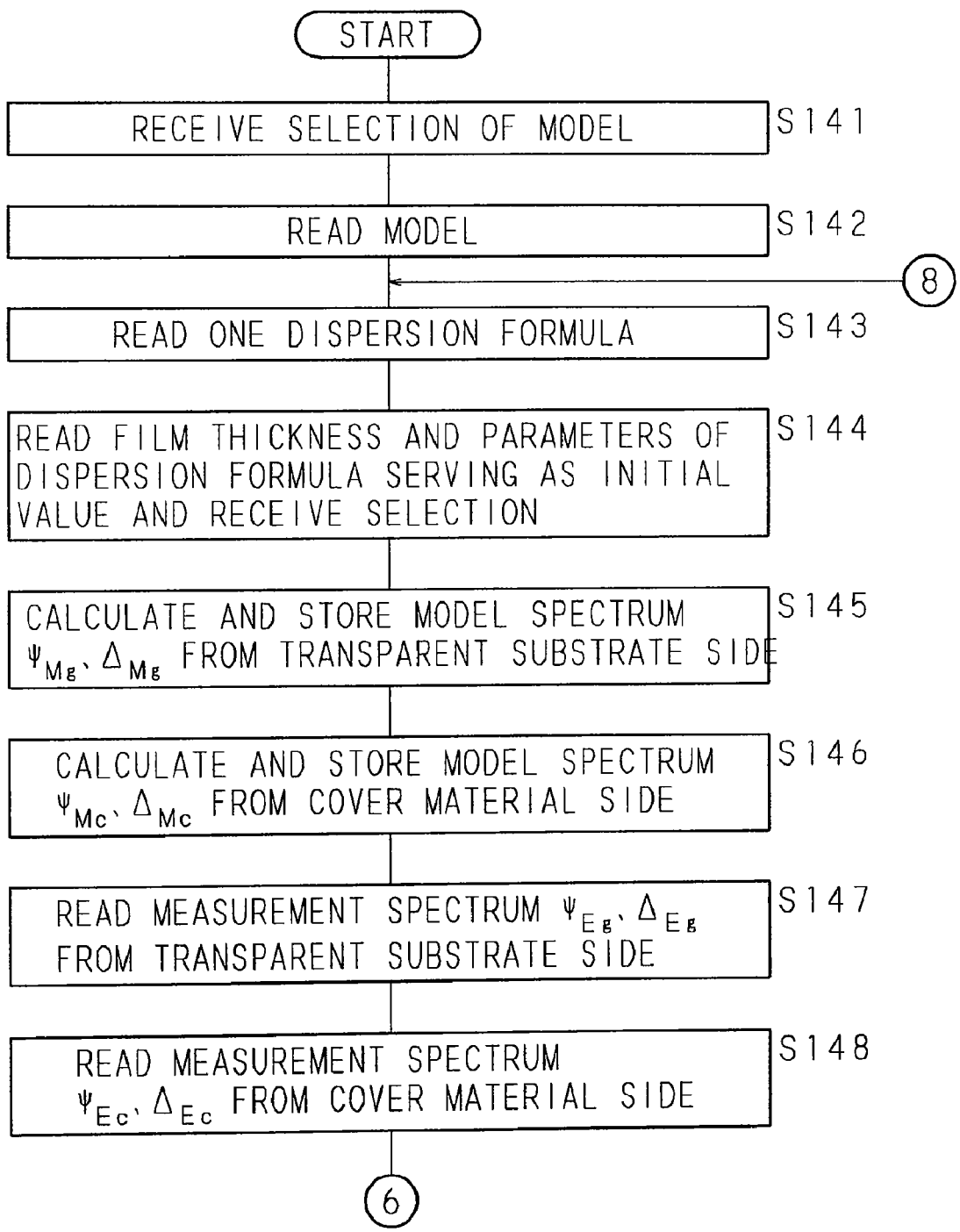
Figure 42C:
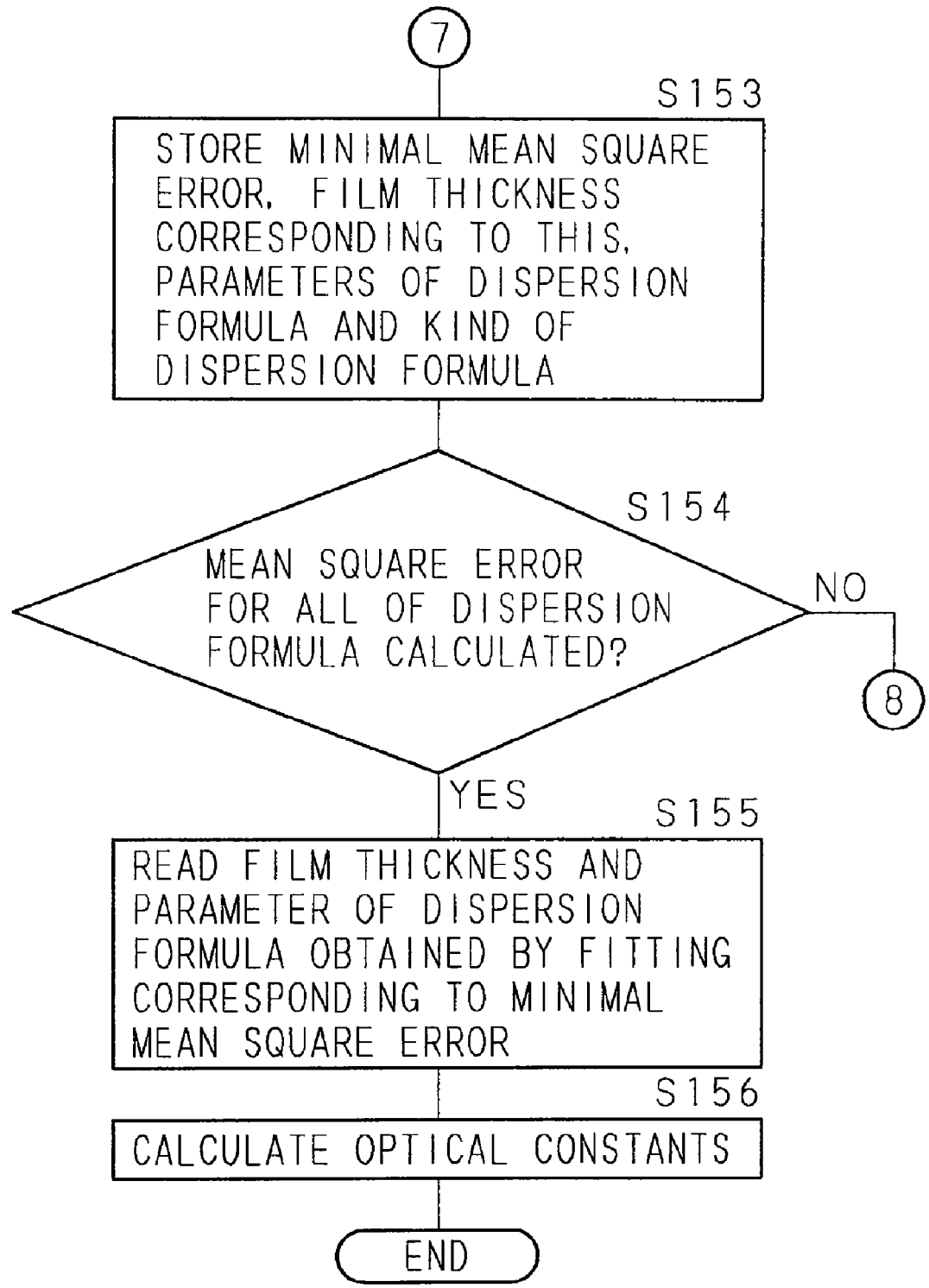

FIGS. 42A to C are flowcharts showing the procedure for calculating the mean square error by using the plurality of dispersion formulas. The CPU 11a receives the selection of the model from the keyboard 13 or mouse 14 (Step S141). When this model is selected, the model is selected from the models m10 to m12 shown in FIG. 32 as the model on the side of the transparent substrate 51. Also, the model is selected from the model m20 or m21 shown in FIG. 34 as the model on the side of the cover material 57.

The CPU 11a reads the selected model from the storage unit 11b (Step S142).

Then, the CPU 11a corresponds to the selected models m11, m20 and reads the plurality of film thicknesses and the parameters of the plurality of dispersion formulas, which are stored in advance and serve as the initial values, from the storage unit 11b and receives the selection of each model from the keyboard 13 or mouse 14 (Step S144) and then determines each model. The CPU 11a of the sample analyzing apparatus 1 calculates the model spectra $\Psi_{Mg}$, $\Delta_{Mg}$ on the side of the transparent substrate 51 in accordance with the read model and stores the result in the storage unit 11b (Step S145). Similarly, the CPU 11a of the sample analyzing apparatus 1 calculates the model spectra $\Psi_{Mc}$, $\Delta_{Mc}$ on the side of the cover material 57 and stores the result in the storage unit 11b (Step S146).

The CPU 11a of the sample analyzing apparatus 1 reads the measurement spectra $\Psi_{Eg}$, $\Delta_{Eg}$ on the side of the transparent substrate 51 measured at the step S72 and further reads the measurement spectra $\Psi_{Ec}$, $\Delta_{Ec}$ on the side of the cover material 57 measured at the step S74, respectively (Step S148). The CPU 11a carries out the process (fitting) that uses the equation (19) for the fitting, compares the measurement spectra $\Psi_{Eg}$, $\Delta_{Eg}$ and the model spectra $\Psi_{Mg}$, $\Delta_{Mg}$ and the measurement spectra $\Psi_{Ec}$, $\Delta_{Ec}$ on the side of the cover material 57 and the model spectra $\Psi_{Mc}$, $\Delta_{Mc}$ and changes the film thicknesses and the parameters of the dispersion formula and the like so as to minimize the different between the measurement spectra and the model spectra. Then, the CPU 11a uses the least squares method as this fitting result and obtains the mean square error $\chi^2$ (Step S149). The mean square error calculated at the step S149 is transiently stored in the RAM 11c.

The CPU 11a judges whether or not the predetermined time elapses (Step S151). If the predetermined time is judged not to elapse (Step S151: NO), the initial film thickness and the parameters of the dispersion formula which are set for each model are properly changed to again calculate the model spectra $\Psi_{Mg}$, $\Delta_{Mg}$ and the model spectra $\Psi_{Mc}$, $\Delta_{Mc}$ (Step S152). After that, the operational flow again proceeds to the step S149, and the similar processes are repeated. The CPU 11a, if judging that the predetermined time elapses (Step S151: YES), stores the mean square error that becomes minimal from the mean square errors stored in the RAM 11c, and the film thickness and parameters of the dispersion formula which correspond thereto, and the kind of the dispersion formula, in the RAM 11c (Step S153). Note that in this embodiment, the process for calculating the minimal value is explained. However, similarly to the seventh embodiment, the comparison with the predetermined value preliminarily stored at the step S151 is carried out. If it becomes this predetermined value or less, the operational flow may proceed to the step S153.

In succession, the CPU 11a judges whether or not the mean square error is calculated for all of the dispersion formulas stored in the storage unit 11b (Step S154). For example, if there are 3 kinds of dispersion formulas, the respective three kinds of the dispersion formulas are used to judge whether or not the minimal value of the mean square errors is calculated. If the CPU 11a judges that the mean square error is not calculated for all of the dispersion formulas (Step S154: NO), the operational flow proceeds to the step S143, and the foregoing processes are repeated. If the CPU 11a judges that the mean square error is calculated for all of the dispersion formulas (Step S154: YES), when the minimal value of the mean square errors is calculated for each of the 3 kinds of the dispersion formulas in the foregoing example, at the step S153, the film thicknesses and the parameters of the dispersion formula which are obtained by the fitting corresponding to the minimal mean square error, from the minimal values of the plurality of mean square errors corresponding to the plurality of dispersion formulas stored in the RAM 11c, are read from the RAM 11c (Step S155). Finally, the CPU 11a refers to the film thicknesses of the respective film layers 52 to 55, the parameters of the dispersion formula and the voids and the like and consequently calculates the optical constants (the refractive indexes n and the extinction coefficients k) of the respective film layers 52 to 55 of the organic film 56 in the organic EL element panel 50 as the optimal value (Step S156). Since the plurality of dispersion formulas as proposed above are used, the film thickness of each layer and the optical constant can be calculated at the high precision. Note that the example of the respective individual applications, such as the manner of using the plurality of dispersion formulas, the manner of using the plurality of incident angles, the manner of using the combination of the plurality of models and the like have been explained. However, the combination of them is naturally allowable.

This eleventh embodiment has the foregoing configuration, and the other configurations and actions are similar to the seventh to tenth embodiments. Thus, the same reference numbers are assigned to the corresponding portions, and their detailed explanations are omitted.

As this invention may be embodied in several forms without departing from the spirit of essential characteristics thereof, present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A manufacturing method of an organic EL element in which film depositions of a plurality of layers are gradually executed in a plurality of film forming chambers, comprising:
    a step of measuring a film thickness of a film deposition product by using a spectroscopic ellipsometer installed outside a film forming chamber; and
    a step of feeding the film deposition product to the film forming chamber installed in a next stage, when the film thickness measured by the spectroscopic ellipsometer achieves a preset film thickness,
    wherein an incident light from the spectroscopic ellipsometer is inputted substantially vertically to a first transmission window obliquely installed in said film forming chamber and a reflected light from the film deposition product is inputted substantially vertically to a second transmission window obliquely installed in said film forming chamber.

2. The manufacturing method of claim 1 further including a step of automatically moving the spectroscopic ellipsometer, relative to a fixed film forming chamber with stationary first and second transmission windows, along a support member by a motor to align the incident light and the reflected light relative to the film forming chamber.

3. The manufacturing method of claim 1 wherein the step of measuring a film thickness includes a predetermined software reference model, including a gap distance between a top of the organic EL element and a cover member, implemented by a computer to determine a film thickness to be deposited.

4. The manufacturing method of claim 3 wherein a pair of predetermined software reference models are stored and enabled by the computer to measure respectively a first measurement of film thickness through a substrate supporting a bottom of the organic EL element and a second measurement of the film thickness through the cover member.

5. A manufacturing equipment of an organic EL element in which film depositions of a plurality of layers are gradually executed in a plurality of film forming chambers, comprising:
    a spectroscopic ellipsometer that is installed outside film forming chamber and measures a film thickness of a film deposition product;
    a first transmission window that is obliquely installed in said film forming chamber and transmits an incident light from said spectroscopic ellipsometer;
    a second transmission window that is obliquely installed in said film forming chamber and transmits a reflected light to the spectroscopic ellipsometer; and
    a feeding device for feeding the film deposition product to the film forming chamber installed in a next stage, when the film thickness measured by the spectroscopic ellipsometer achieves a preset film thickness.

6. The manufacturing equipment of the organic EL element according to claim 5, further comprising a film forming unit that is installed on a deposition direction side of the film deposition product and supplies a film deposition material,
    wherein said spectroscopic ellipsometer is installed on a side opposite to the deposition direction of the film deposition product.

7. The manufacturing equipment of the organic EL element according to claim 6, further comprising a controller for controlling said film forming unit.

8. The manufacturing equipment of the organic EL element according to claim 7, further comprising a processor of said spectroscopic ellipsometer that executes the following process of:
    a step of calculating a film thickness deposition rate of the film deposition product; and
    a step of outputting a deviation between the calculated film thickness deposition rate and a preset film thickness deposition rate to said controller,
    wherein said controller is configured so as to control said film forming unit so that the output deviation becomes approximately zero.

9. The manufacturing equipment of the organic EL element according to claim 7,
    wherein
    the processor of said spectroscopic ellipsometer further carries out the following process of:
        a step of calculating an optical constant of the film deposition product; and
        a step of outputting a deviation between the calculated optical constant and a preset optical constant to said controller,
        wherein said controller is configured so as to control said film forming unit so that the output deviation becomes approximately zero.

10. The manufacturing equipment of claim 5 further including means for automatically moving the spectroscopic ellipsometer, relative to a fixed film forming chamber with stationary first and second transmission windows, along a support member by a motor to align the incident light and the reflected light relative to the film forming chamber.

11. The manufacturing equipment of claim 10 wherein the support member is one of a rail system and a pulley system.

12. The manufacturing equipment of claim 5 wherein measuring a film thickness by the spectroscopic ellipsometer includes a predetermined software reference model, that provides a gap distance between a top of the organic EL element and a cover member, implemented by a computer to determine a film thickness to be deposited.

13. The manufacturing equipment of claim 12 wherein a pair of predetermined software reference models are stored and enabled by the computer to measure respectively a first measurement of film thickness through a substrate supporting a bottom of the organic EL element and a second measurement of the film thickness through the cover member.

14. A manufacturing equipment of an organic EL element in which film depositions of a plurality of layers are gradually executed in a plurality of film forming chambers, comprising:
 a spectroscopic ellipsometer that is installed outside film forming chamber and measures a film thickness of a film deposition product; and
 a first transmission window that is obliquely installed in said film forming chamber and transmits an incident light from said spectroscopic ellipsometer;
 a second transmission window that is obliquely installed in said film forming chamber and transmits a reflected light to the spectroscopic ellipsometer; and
 means for feeding the film deposition product to the film forming chamber installed in a next stage, when the film thickness measured by the spectroscopic ellipsometer achieves a preset film thickness.

15. The manufacturing equipment of the organic EL element according to claim 14, further comprising:
 a film forming unit that is installed on the deposition direction side of the film deposition product and supplies a film deposition material,
 wherein said spectroscopic ellipsometer is installed on the side opposite to the deposition direction of the film deposition product.

16. The manufacturing equipment of the organic EL element according to claim 15, further comprising control means for controlling said film forming unit.

17. The manufacturing equipment of the organic EL element according to claim 16,
 wherein said spectroscopic ellipsometer further comprises:
  means for calculating a film thickness deposition rate of the film deposition product; and
  means for outputting a deviation between the calculated film thickness deposition rate and a preset film thickness deposition rate to said controller, and
  wherein said control means is configured so as to control said film forming unit so that the output deviation becomes approximately zero.

18. The manufacturing equipment of the organic EL element according to claim 16,
 wherein
 said spectroscopic ellipsometer further comprises;
  means for calculating an optical constant of the film deposition product; and
  means for outputting a deviation between the calculated optical constant and a preset optical constant to said control means, and
  wherein said control means is configured so as to control said film forming unit so that the output deviation becomes approximately zero.

19. The manufacturing equipment of claim 14 further including means for automatically moving the spectroscopic ellipsometer, relative to a fixed film forming chamber with stationary first and second transmission windows, along a support member by a motor to align the incident light and the reflected light relative to the film forming chamber.

20. The manufacturing of claim 14 wherein measuring a film thickness includes a predetermined software reference model, including a gap distance between a top of the organic EL element and a cover member, implemented by a computer to determine a film thickness to be deposited.

* * * * *